(12) United States Patent
Blanck

(10) Patent No.: US 8,352,194 B1
(45) Date of Patent: Jan. 8, 2013

(54) METHOD TO IDENTIFY CANCER FUSION GENES

(75) Inventor: George Blanck, Tampa, FL (US)

(73) Assignee: University of South Florida, Tampa, FL (US)

( * ) Notice: Subject to any disclaimer, the term of this patent is extended or adjusted under 35 U.S.C. 154(b) by 385 days.

(21) Appl. No.: 12/486,545

(22) Filed: Jun. 17, 2009

Related U.S. Application Data

(60) Provisional application No. 61/073,211, filed on Jun. 17, 2008.

(51) Int. Cl.
*G06F 7/00* (2006.01)
(52) U.S. Cl. ............... 702/19; 702/20; 703/11; 707/700
(58) Field of Classification Search .................. None
See application file for complete search history.

(56) References Cited

U.S. PATENT DOCUMENTS

| | | |
|---|---|---|
| 6,174,674 B1 | 1/2001 | Morris et al. |
| 6,183,969 B1 | 2/2001 | Gabriel |
| 7,368,245 B2 | 5/2008 | Van Dongen et al. |
| 2004/0110227 A1 | 6/2004 | Levanon et al. |

OTHER PUBLICATIONS

Narsing, S., et al., Genes that Contribute to Cancer Fusion Genes are Large and Evolutionarily Conserved, Cancer Genetics and Cytogenetics, 2009, vol. 191, pp. 78-84.
Taub, R., et al, Translocation of the c-myc Gene into the Immunoglobulin Heavy Chain Locus in Human Burkitt Lymphoma and Murine Plasmacytoma Cells, Proc. Nat'l Acad. Sci. USA, 1982, vol. 79, pp. 7837-7841.
Dalla-Favera, R., et al., Human c-myc onc Gene is Located on the Region of Chromosome 8 that is Translocated in Burkitt Lymphoma Cells, Proc. Nat'l Acad. Sci. USA, 1982, vol. 79, pp. 7824-7827.
Neel, B., et al., Two Human c-onc Genes are Located on the Long Arm of Chromosome 8, Proc. Nat'l Acad. Sci. USA, 1982, vol. 79, pp. 7842-7846.
Heisterkamp, N., et al., Structural Organization of the bcr Gene and its Role in the Ph' Translocation, Nature, 1985, vol. 315, pp. 758-761.
Buchdunger, E., et al., Inhibition of the Abl Protein-Tyrosine Kinase in Vitro and in Vivo by a 2-Phenylaminopyrimidine Derivative, Cancer Research, 1996, vol. 56, pp. 100-104.
Druker, B., et al., Effects of a Selective Inhibitor of the Abl Tyrosine Kinase on the Growth of Bcr-Abl Positive Cells, Nature Medicine, 1996, vol. 2, No. 5, pp. 561-566.
Chiarle, R., et al., The Anaplastic Lymphoma Kinase is an Effective Oncoantigen for Lymphoma Vaccination, Nature Medicine, 2008 , vol. 14, pp. 676-680.
Raphael, B., et al., A Sequence-Based Survey of the Complex Structural Organization of Tumor Genomes, Genome Biology, 2008, vol. 9, pp. R59.1-R59.17.
Maher, C., et al., Transcriptome Sequencing to Detect Gene Fusions in Cancer, Nature, 2009, vol. 458, pp. 97-101.
Chen, S. et al., Ph1+bcr- Acute Leukemias: Implication of Alu Sequences in a Chromosomal Translocation Occurring in the New Cluster Region Within the BCR Gene, Oncogene, 1989, vol. 4, pp. 195-202.
Papadopoulos, P., et al., Characterization of the Translocation Breakpoint Sequences in Philadelphia-Positive Acute Lymphoblastic Leukemia, Genes Chromosomes Cancer, 1990, vol. 1, pp. 233-239.
Kurahashi, H., et al., Molecular Cloning of a Translocation Breakpoint Hotspot in 22q11, Genome Research, 2007, vol. 17, pp. 461-469.
Babcock, M., et al., AT-Rich Repeats Associated with Chromosome 22q11.2 Rearrangement Disorders Shape Human Genome Architecture on Yq12, Genome Research, 2007, vol. 17, pp. 451-460.
Volik, S., et al., Decoding the Fine-Scale Structure of a Breast Cancer Genome and Transcriptome, Genome Research, 2006, vol. 16, pp. 394-404.
Matsubara, K. et al., Identification of Chromosome Rearrangements Between the Laboratory Mouse (*Mus musculus*) and the Indian Spiny Mouse (*Mus platythrix*) by Comparative FISH Analysis, Chromosome Research, 2003, vol. 11, pp. 57-64, 2003.
Maslak, P., et al., A Pilot Vaccination Trial of Synthetic Analog Peptides Derived from the BCR-ABL Breakpoints in CML Patients with Minimal Disease, Leukemia, 2008, vol. 22, pp. 1613-1616.
Rabbitts, T., Chromosomal Translocation in Human Cancer, Nature, 1994, pp. 143-149.
Sanchez-Garcia, I., Consequences of Chromosomal Abnormalities in Tumor Development, Annual Reviews Genet. 1997, vol. 31, pp. 429-453.
De Klein, A, et al., A Cellular Oncogene is Translocated to the Philadelphia Chromosome in Chronic Myelocytic Leukaemia, Nature, 1982, vol. 300, pp. 765-767.
Altuvia, Y .et al., Clustering and Conservation Patterns of Human MicroRNAs, Nucleic Acids Research, 2005, vol. 33, No. 8, pp. 2697-2706.
Blanck, G., Cancer Karyotype Genomics: Data Mining the Common Characteristics of Cancer Fusion Genes, Department of Molecular Medicine, 2009.
Mitelman, F, et al., The Impact of Translocations and Gene Fusions on Cancer Causation, Nature Review, 2007, vol. 7, pp. 233-245.
Teixeira, M., Recurrent Fusion Oncogenes in Carcinomas, Critical Reviews in Oncogenesis, 2006, vol. 12, pp. 257-271.
Vega, F. et al., Chromosomal Translocations Involved in Non-Hodgkin Lymphomas, Archives of Pathology Laboratory Medicine, 2003, vol. 127, pp. 1148-1160.
Hahn, Y. et al., Finding Fusion Genes Resulting from Chromosome Rearrangement by Analyzing the Expressed Sequence Databases, PNAS, 2004, vol. 101, No. 36, pp. 13257-13261.

*Primary Examiner* — Mary Zeman
(74) *Attorney, Agent, or Firm* — Robert J. Varkonyi; Smith & Hopen, P.A.

(57) ABSTRACT

Numerous cancer fusion genes have been identified and studied, and in some cases therapy or diagnostic techniques have been designed that are specific to the fusion protein encoded by the fusion gene. However, there has been little progress in understanding the general features of cancer fusions genes in a way that could provide the foundation for an algorithm for predicting the occurrence of a fusion gene once the chromosomal translocation points have been identified by karyotype analyses. In this study, characterization of 59 cancer fusion genes indicated that all but a small percentage of the genes involved in fusion events are either relatively large, compared to neighboring genes, or are highly conserved in evolution. These results support a basis for designing algorithms that could have a high degree of predictive value in identifying fusion genes once conventional microscopic analyses have identified the chromosomal breakpoints.

18 Claims, 116 Drawing Sheets

Chromosome position represented
chr9:131,579,089-133,752,883
Total number of genes 28

Total units is always 42

| #name | txStart | txEnd | size | fusion gene name | Rank size order | Comparative genomics peak order | standard | actual | gene size |
|---|---|---|---|---|---|---|---|---|---|
| uc004byk.1 | 131605252 | 131613381 | 8129 | | | | | | |
| uc004byl.1 | 131615041 | 131626262 | 11221 | | | | | | |
| uc004bym.1 | 131615041 | 131626262 | 11221 | | | | | | |
| uc004byn.1 | 131623475 | 131626262 | 2787 | | | | | | |
| uc004byo.1 | 131629384 | 131635617 | 6233 | | | | | | |
| uc004byp.1 | 131629384 | 131637393 | 8009 | | | | | | |
| uc004byq.1 | 131630527 | 131636647 | 6120 | | | | | | |
| uc004byr.1 | 131637569 | 131683928 | 46359 | | | | | | |
| uc004bys.1 | 131637569 | 131683928 | 46359 | | | | | | |
| uc004byt.1 | 131637577 | 131683928 | 46351 | | | | | | |
| uc004byu.1 | 131681473 | 131683864 | 2391 | | | | | | |
| uc004byv.1 | 131689286 | 131695214 | 5928 | | | | | | |
| uc004byw.1 | 131689286 | 131845294 | 156008 | | | | | | |
| uc004byx.1 | 131697367 | 131797058 | 99691 | | | | | | |
| uc004byy.1 | 131697367 | 131797058 | 99691 | | | | | | |
| uc004byz.1 | 131697367 | 131845294 | 147927 | | | | | | |
| uc004bza.1 | 131710989 | 131845294 | 134305 | | | | | | |
| uc004bzb.1 | 131855856 | 131932124 | 76268 | | | | | | |
| uc004bzc.1 | 131855856 | 131940117 | 84261 | | | | | | |
| uc004bzd.1 | 131855856 | 131942264 | 86408 | | | | | | |
| uc004bze.1 | 131855856 | 131942264 | 86408 | | | | | | |
| uc004bzf.1 | 131909787 | 131910419 | 632 | | | | | | |
| uc004bzg.1 | 131931752 | 131939000 | 7248 | | | | | | |
| uc004bzh.1 | 131942709 | 131946319 | 3610 | | | | | | |
| uc004bzi.1 | 131974677 | 132038726 | 64049 | | | | | | |
| uc004bzj.1 | 132250948 | 132284790 | 33842 | | | | | | |
| uc004bzk.1 | 132263815 | 132272460 | 8645 | | | | | | |

Fig. 1a

| #name | txStart | txEnd | size | fusion gene name | Rank size order | Comparative genomics peak order | standard | actual | gene size |
|---|---|---|---|---|---|---|---|---|---|
| uc004bzl.1 | 132295489 | 132299331 | 3842 | | | | | | |
| uc004bzm.1 | 132309914 | 132366482 | 56568 | | | | | | |
| uc004bzn.1 | 132309914 | 132366482 | 56568 | | | | | | |
| uc004bzo.1 | 132309914 | 132366482 | 56568 | | | | | | |
| uc004bzp.1 | 132317388 | 132366482 | 49094 | | | | | | |
| uc004bzq.1 | 132444780 | 132446928 | 2148 | | | | | | |
| uc004bzr.1 | 132444780 | 132503560 | 58780 | | | | | | |
| uc004bzs.1 | 132444780 | 132503560 | 58780 | | | | | | |
| uc004bzt.1 | 132529801 | 132548205 | 18404 | | | | | | |
| uc004bzu.1 | 132558997 | 132570077 | 11080 | | | | | | |
| uc004bzv.1 | 132579088 | 132752883 uc004bzv.1 | 173795 | ABL | 2 | | | | |
| uc004bzw.1 | 132700651 | 132752883 | 52232 | | | | | | |
| uc004bzx.1 | 132728516 | 132730955 | 2439 | | | | | | |
| uc004bzy.1 | 132758635 | 132759046 | 411 | | | | | | |
| uc004bzz.1 | 132767721 | 132804058 | 36337 | | | | | | |
| uc004caa.1 | 132874324 | 132958267 | 83943 | | | | | | |
| uc004cab.1 | 132961732 | 132988360 | 26628 | | | | | | |
| uc004cac.1 | 132961732 | 132988360 | 26628 | | | | | | |
| uc004cad.1 | 132961732 | 132988360 | 26628 | | | | | | |
| uc004cae.1 | 132961732 | 132988360 | 26628 | | | | | | |
| uc004caf.1 | 132990801 | 133043618 | 52817 | | | | | | |
| uc004cag.1 | 132990801 | 133098912 | 108111 | | | | | | |
| uc004cah.1 | 132990801 | 133098912 | 108111 | | | | | | |
| uc004cai.1 | 133009487 | 133098912 | 89425 | | | | | | |
| uc004caj.1 | 133123285 | 133135701 | 12416 | | | | | | |
| uc004cak.1 | 133123285 | 133141727 | 18442 | | | | | | |
| uc004cal.1 | 133154944 | 133174468 | 19524 | | | | | | |
| uc004cam.1 | 133259420 | 133312414 | 52994 | | | | | | |
| uc004can.1 | 133312292 | 133363365 | 51073 | | | | | | |
| uc004cao.1 | 133335995 | 133363365 | 27370 | | | | | | |

| Rank order of peak size | Number of units covered by gene +/-3 | Distance from gene to peak | Gene size in units |
|---|---|---|---|
| 1 | 10 | 2 | 4 |

Fig. 1b

| #name | txStart | txEnd | size | fusion gene name | Rank size order | Comparative genomics peak order | standard | actual | gene size |
|---|---|---|---|---|---|---|---|---|---|
| uc004cap.1 | 1333350155 | 1333363365 | 13210 | | | | | | |
| uc004caq.1 | 1333350872 | 1333350958 | 86 | | | | | | |
| uc004car.1 | 1333355693 | 1333355779 | 86 | | | | | | |
| uc004cas.1 | 1333362686 | 1333365399 | 2713 | | | | | | |
| uc004cat.1 | 1333362914 | 1333365404 | 2490 | | | | | | |
| uc004cau.1 | 1333368109 | 1333389014 | 20905 | | | | | | |
| uc004cav.1 | 1333368109 | 1333389014 | 20905 | | | | | | |
| uc004caw.1 | 1333368109 | 1333389014 | 20905 | | | | | | |
| uc004cax.1 | 1333368164 | 1333389014 | 20850 | | | | | | |
| uc004cay.1 | 1333389011 | 1333396476 | 7465 | | | | | | |
| uc004caz.1 | 1333389011 | 1333396476 | 7465 | | | | | | |
| uc004cba.1 | 1333389011 | 1333396476 | 7465 | | | | | | |
| uc004cbb.1 | 1334441977 | 1335575050 | 133073 | | | | | | |
| uc004cbc.1 | 1334441977 | 1336602746 | 160769 | | | | | | |
| uc004cbd.1 | 1334457304 | 1336605053 | 147749 | | | | | | |
| uc004cbe.1 | 1337725319 | 1339945074 | 219755 | | | | | | |
| uc004cbf.1 | 1337725319 | 1339945074 | 219755 | | | | | | |

Fig. 1c

Chromosome position represented  
chr5:131,238,970-133,327,253  
Total number of genes 24

Total units is always 42

| #name | txStart | txEnd | size | fusion gene name | Rank size order | Comparative genomics peak order | standard | actual | gene size |
|---|---|---|---|---|---|---|---|---|---|
| uc003kvv.1 | 131170738 | 131357870 | 187132 | | | | | | |
| uc003kvw.1 | 131317050 | 131337627 | 20577 | | | | | | |
| uc003kvx.1 | 131317050 | 131375248 | 58198 | | | | | | |
| uc003kvy.1 | 131317050 | 131375248 | 58198 | | | | | | |
| uc003kvz.1 | 131317050 | 131375476 | 58426 | | | | | | |
| uc003kwa.1 | 131317050 | 131375553 | 58503 | | | | | | |
| uc003kwb.1 | 131336315 | 131357843 | 21528 | | | | | | |
| uc003kwc.1 | 131352998 | 131375769 | 22771 | | | | | | |
| uc003kwd.1 | 131352998 | 131375769 | 22771 | | | | | | |
| uc003kwe.1 | 131424245 | 131426795 | 2550 | | | | | | |
| uc003kwf.1 | 131437383 | 131439758 | 2375 | | | | | | |
| uc003kwg.1 | 131556202 | 131590834 | 34632 | | | | | | |
| uc003kwh.1 | 131556202 | 131590834 | 34632 | | | | | | |
| uc003kwi.1 | 131556202 | 131590853 | 34651 | | | | | | |
| uc003kwj.1 | 131556202 | 131591455 | 35253 | | | | | | |
| uc003kwk.1 | 131556202 | 131591455 | 35253 | | | | | | |
| uc003kwl.1 | 131556202 | 131591455 | 35253 | | | | | | |
| uc003kwm.1 | 131612499 | 131644520 | 32021 | | | | | | |
| uc003kwn.1 | 131621285 | 131637046 | 15761 | | | | | | |
| uc003kwo.1 | 131621285 | 131637046 | 15761 | | | | | | |
| uc003kwp.1 | 131621285 | 131637046 | 15761 | | | | | | |
| uc003kwq.1 | 131658043 | 131707798 | 49755 | | | | | | |
| uc003kwr.1 | 131674876 | 131723712 | 48836 | | | | | | |
| uc003kws.1 | 131708272 | 131712332 | 4060 | | | | | | |
| uc003kwt.1 | 131722665 | 131723712 | 1047 | | | | | | |
| uc003kwu.1 | 131729544 | 131733095 | 3551 | | | | | | |
| uc003kwv.1 | 131729544 | 131733507 | 3963 | | | | | | |

Fig. 2a

| #name | txStart | txEnd | size | fusion gene name | Rank size order | Comparative genomics peak order | standard | actual | gene size |
|---|---|---|---|---|---|---|---|---|---|
| uc003kww.1 | 131733342 | 131759202 | 25860 | | | | | | |
| uc003kwx.1 | 131733342 | 131759202 | 25860 | | | | | | |
| uc003kwy.1 | 131774571 | 131825958 | 51387 | | | | | | |
| uc003kwz.1 | 131774571 | 131839630 | 65059 | | | | | | |
| uc003kxa.1 | 131846683 | 131854326 | 7643 | | | | | | |
| uc003kxb.1 | 131846683 | 131859158 | 12475 | | | | | | |
| uc003kxc.1 | 131849221 | 131853074 | 3853 | | | | | | |
| uc003kxd.1 | 131850544 | 131854326 | 3782 | | | | | | |
| uc003kxe.1 | 131905034 | 131907113 | 2079 | | | | | | |
| uc003kxf.1 | 131905605 | 131920427 | 14822 | | | | | | |
| uc003kxg.1 | 131919609 | 131943657 | 24048 | | | | | | |
| uc003kxh.1 | 131920528 | 132007494 | 86966 | | | | | | |
| uc003kxi.1 | 131920528 | 132007494 | 86966 | | | | | | |
| uc003kxj.1 | 132021763 | 132024700 | 2937 | | | | | | |
| uc003kxk.1 | 132037271 | 132046267 | 8996 | | | | | | |
| uc003kxl.1 | 132037271 | 132046267 | 8996 | | | | | | |
| uc003kxm.1 | 132056221 | 132067220 | 10999 | | | | | | |
| uc003kxn.1 | 132056221 | 132098069 | 41848 | | | | | | |
| uc003kxo.1 | 132056221 | 132101164 | 44943 | | | | | | |
| uc003kxp.1 | 132056221 | 132101164 | 44943 | | | | | | |
| uc003kxq.1 | 132111035 | 132117755 | 6720 | | | | | | |
| uc003kxr.1 | 132114415 | 132140966 | 26551 | | | | | | |
| uc003kxs.1 | 132119595 | 132140966 | 21371 | | | | | | |
| uc003kxt.1 | 132119595 | 132141369 | 21774 | | | | | | |
| uc003kxu.1 | 132121734 | 132140966 | 19232 | | | | | | |
| uc003kxv.1 | 132121734 | 132140966 | 19232 | | | | | | |
| uc003kxw.1 | 132176931 | 132180388 | 3457 | | | | | | |
| uc003kxx.1 | 132185733 | 132194489 | 8756 | | | | | | |
| uc003kxy.1 | 132185910 | 132189901 | 3991 | | | | | | |
| uc003kxz.1 | 132224776 | 132228376 | 3600 | | | | | | |
| uc003kya.1 | 132230217 | 132232435 | 2218 | | | | | | |
| uc003kyb.1 | 132237256 | 132238286 | 1030 | | | | | | |
| uc003kyc.1 | 132237256 | 132238481 | 1225 | | | | | | |

Fig. 2b

| #name | txStart | txEnd | size | fusion gene name | Rank size order | Comparative genomics peak order Rank order of peak size | standard Number of units covered by gene +/-3 | actual Distance from gene to gene | gene size Gene size in units |
|---|---|---|---|---|---|---|---|---|---|
| uc003kyd.1 | 132238969 | 132327253 uc003kyd.1 | 88284 | AF4 | 3 | 1 | 8 | 0 | 2 |
| uc003kye.1 | 132255407 | 132327253 | 71846 | | | | | | |
| uc003kyf.1 | 132290315 | 132327253 | 36938 | | | | | | |
| uc003kyg.1 | 132360575 | 132390139 | 29564 | | | | | | |
| uc003kyh.1 | 132360575 | 132390139 | 29564 | | | | | | |
| uc003kyi.1 | 132382641 | 132390139 | 7498 | | | | | | |
| uc003kyj.1 | 132415560 | 132468608 | 53048 | | | | | | |
| uc003kyk.1 | 132415560 | 132468608 | 53048 | | | | | | |
| uc003kyl.1 | 132474658 | 132478066 | 3408 | | | | | | |
| uc003kym.1 | 132560050 | 132589516 | 29466 | | | | | | |
| uc003kyn.1 | 132560050 | 132976122 | 416072 | | | | | | |
| uc003kyo.1 | 133319099 | 133332377 | 13278 | | | | | | |

Fig. 2c

Chromosome position represented
chr2:28,269,144-30,997,936
Total number of genes    18
Total units is always 42

| #name | txStart | txEnd | size | fusion gene name | Rank size order | Comparative genomics peak order | standard | actual | gene size |
|---|---|---|---|---|---|---|---|---|---|
| uc002rlp.1 | 27966985 | 28415087 | 448102 | | | | | | |
| uc002rlq.1 | 27966985 | 28415271 | 448286 | | | | | | |
| uc002rlr.1 | 27966985 | 28415271 | 448286 | | | | | | |
| uc002rls.1 | 27966985 | 28415271 | 448286 | | | | | | |
| uc002rlt.1 | 27966985 | 28415271 | 448286 | | | | | | |
| uc002rlu.1 | 27966985 | 28415271 | 448286 | | | | | | |
| uc002rlv.1 | 28006193 | 28415271 | 409078 | | | | | | |
| uc002rlx.1 | 28374699 | 28415271 | 40572 | | | | | | |
| uc002rly.1 | 28384061 | 28386830 | 2769 | | | | | | |
| uc002rlz.1 | 28460779 | 28471043 | 10264 | | | | | | |
| uc002rma.1 | 28469282 | 28491020 | 21738 | | | | | | |
| uc002rmb.1 | 28572485 | 28720117 | 147632 | | | | | | |
| uc002rmc.1 | 28624870 | 28672430 | 47560 | | | | | | |
| uc002rmd.1 | 28643159 | 28669662 | 26503 | | | | | | |
| uc002rme.1 | 28678269 | 28720117 | 41848 | | | | | | |
| uc002rmf.1 | 28681025 | 28720117 | 39092 | | | | | | |
| uc002rmg.1 | 28828117 | 28879310 | 51193 | | | | | | |
| uc002rmh.1 | 28828129 | 28879310 | 51181 | | | | | | |
| uc002rmi.1 | 28858886 | 28917179 | 58293 | | | | | | |
| uc002rmj.1 | 28887220 | 28926979 | 39759 | | | | | | |
| uc002rmk.1 | 28887220 | 28926979 | 39759 | | | | | | |
| uc002rml.1 | 28892366 | 28917179 | 24813 | | | | | | |
| uc002rmm.1 | 28926191 | 28946669 | 20478 | | | | | | |
| uc002rmn.1 | 28926191 | 28946669 | 20478 | | | | | | |
| uc002rmo.1 | 28971039 | 29024584 | 53545 | | | | | | |
| uc002rmp.1 | 28990031 | 28990120 | 89 | | | | | | |
| uc002rmq.1 | 29003436 | 29003512 | 76 | | | | | | |

Fig. 3a

| #name | txStart | txEnd | size | fusion gene name | Rank size order | Comparative genomics peak order |
|---|---|---|---|---|---|---|
| uc002rmr.1 | 29090836 | 29128594 | 37758 | | | |
| uc002rms.1 | 29109800 | 29123917 | 14117 | | | |
| uc002rmt.1 | 29138061 | 29150631 | 12570 | | | |
| uc002rmu.1 | 29174074 | 29236837 | 62763 | | | |
| uc002rmv.1 | 29191821 | 29260178 | 68357 | | | |
| uc002rmw.1 | 29197743 | 29260178 | 62435 | | | |
| uc002rmx.1 | 29208521 | 29251083 | 42562 | | | |
| uc002rmy.1 | 29269143 | 29997936 | 728793 uc002rmy.1 | ALK | 1 | |
| uc002rmz.1 | 30223331 | 30236903 | 13572 | | | |
| uc002rna.1 | 30223331 | 30236903 | 13572 | | | |
| uc002rnb.1 | 30223331 | 30236903 | 13572 | | | |
| uc002rnc.1 | 30223331 | 30236903 | 13572 | | | |
| uc002rnd.1 | 30223885 | 30236903 | 13018 | | | |
| uc002rne.1 | 30307900 | 30336393 | 28493 | | | |
| uc002rnf.1 | 30423028 | 30426528 | 3500 | | | |
| uc002rng.1 | 30427287 | 30428801 | 1514 | | | |
| uc002rnh.1 | 30484539 | 30484615 | 76 | | | |
| uc002rni.1 | 30484615 | 30484716 | 101 | | | |
| uc002rnj.1 | 30523626 | 30720595 | 196969 | | | |
| uc002rnk.1 | 30523640 | 30684216 | 160576 | | | |
| uc002rnl.1 | 30523640 | 30720595 | 196955 | | | |
| uc002rnm.1 | 30799141 | 30819952 | 20811 | | | |
| uc002rnn.1 | 30799141 | 30883815 | 84674 | | | |
| uc002rno.1 | 30817743 | 30819952 | 2209 | | | |
| uc002rnp.1 | 30827472 | 30883815 | 56343 | | | |
| uc002rnq.1 | 30986836 | 31205994 | 219158 | | | |
| uc002rnr.1 | 30986836 | 31215075 | 228239 | | | |
| uc002rns.1 | 30986836 | 31215075 | 228239 | | | |

| Rank order of peak size | Number of units covered by gene +/-3 standard | actual | Distance from gene to peak | Gene size in units |
|---|---|---|---|---|
| 5 | 18 | | 0 | 12 |

Fig. 3b

Chromosome position represented
chr22:20,852,552-22,990,224
Total number of genes  32

Total units is always 42

| #name | txStart | txEnd | size | fusion gene name | Rank size order | Comparative genomics peak order | standard | actual | gene size |
|---|---|---|---|---|---|---|---|---|---|
| uc002zvw.1 | 20715571 | 21595078 | 879507 | | | | | | |
| uc002zvx.1 | 20929199 | 20929926 | 727 | | | | | | |
| uc002zvy.1 | 20982513 | 20991653 | 9140 | | | | | | |
| uc002zvz.1 | 20987588 | 20993088 | 5500 | | | | | | |
| uc002zwa.1 | 21011887 | 21042543 | 30656 | | | | | | |
| uc002zwb.1 | 21116692 | 21578968 | 462276 | | | | | | |
| uc002zwc.1 | 21168771 | 21193505 | 24734 | | | | | | |
| uc002zwd.1 | 21169218 | 21171803 | 2585 | | | | | | |
| uc002zwe.1 | 21198060 | 21204613 | 6553 | | | | | | |
| uc002zwf.1 | 21220122 | 21230022 | 9900 | | | | | | |
| uc002zwg.1 | 21220122 | 21231550 | 11428 | | | | | | |
| uc002zwh.1 | 21220122 | 21231550 | 11428 | | | | | | |
| uc002zwi.1 | 21220122 | 21231696 | 11574 | | | | | | |
| uc002zwj.1 | 21220122 | 21231696 | 11574 | | | | | | |
| uc002zwk.1 | 21220122 | 21231696 | 11574 | | | | | | |
| uc002zwl.1 | 21231749 | 21239004 | 7255 | | | | | | |
| uc002zwm.1 | 21309652 | 21311152 | 1500 | | | | | | |
| uc002zwn.1 | 21315767 | 21315805 | 38 | | | | | | |
| uc002zwo.1 | 21316172 | 21316202 | 30 | | | | | | |
| uc002zwp.1 | 21316618 | 21316650 | 32 | | | | | | |
| uc002zwq.1 | 21318779 | 21320368 | 1589 | | | | | | |
| uc002zwr.1 | 21559959 | 21568005 | 8046 | | | | | | |
| uc002zws.1 | 21559959 | 21578969 | 19010 | | | | | | |
| uc002zwt.1 | 21731592 | 21814241 | 82649 | | | | | | |
| uc002zwu.1 | 21742668 | 21797221 | 54553 | | | | | | |
| uc002zwv.1 | 21817512 | 21836531 | 19019 | | | | | | |
| uc002zww.1 | 21852551 | 21990224 | 137673 | | | | | | |

Fig. 4a

| #name | txStart | txEnd | size | fusion gene name | Rank size order | Comparative genomics peak order Rank order of peak size | standard Number of units covered by gene +/-3 | actual Distance from gene to peak | gene size Gene size in units |
|---|---|---|---|---|---|---|---|---|---|
| uc002zwx.1 | 218525551 | 21990224 uc002zwx.1 | 137673 | BCR | 4 | 4 | 8 | 2 | 2 |
| uc002zwy.1 | 219553955 | 219633318 | 7923 | | | | | | |
| uc002zwz.1 | 220627922 | 220747422 | 11950 | | | | | | |
| uc002zxa.1 | 220627922 | 220747422 | 11950 | | | | | | |
| uc002zxb.1 | 220627922 | 220747422 | 11950 | | | | | | |
| uc002zxc.1 | 221342722 | 221591672 | 24895 | | | | | | |
| uc002zxd.1 | 222453122 | 222524952 | 7183 | | | | | | |
| uc002zxe.1 | 222453122 | 222524952 | 7183 | | | | | | |
| uc002zxf.1 | 222806382 | 223044872 | 23849 | | | | | | |
| uc002zxg.1 | 222827772 | 222828032 | 26 | | | | | | |
| uc002zxh.1 | 223106742 | 223653382 | 54664 | | | | | | |
| uc002zxi.1 | 223106742 | 223653722 | 54698 | | | | | | |
| uc002zxj.1 | 223106742 | 223814282 | 70754 | | | | | | |
| uc002zxk.1 | 223106742 | 223814282 | 70754 | | | | | | |
| uc002zxl.1 | 223106742 | 223814282 | 70754 | | | | | | |
| uc002zxm.1 | 223253552 | 223814282 | 56073 | | | | | | |
| uc002zxn.1 | 223629602 | 223713632 | 8403 | | | | | | |
| uc002zxo.1 | 223629602 | 223713632 | 8403 | | | | | | |
| uc002zxp.1 | 223634922 | 223713542 | 7862 | | | | | | |
| uc002zxq.1 | 223634922 | 223713632 | 7871 | | | | | | |
| uc002zxr.1 | 224108692 | 224156942 | 4825 | | | | | | |
| uc002zxs.1 | 224137712 | 224232792 | 9508 | | | | | | |
| uc002zxt.1 | 224249312 | 224265922 | 1661 | | | | | | |
| uc002zxu.1 | 224352072 | 224380212 | 2814 | | | | | | |
| uc002zxv.1 | 224352072 | 224380472 | 2840 | | | | | | |
| uc002zxw.1 | 224380202 | 224401412 | 2121 | | | | | | |
| uc002zxx.1 | 224450352 | 224565032 | 11468 | | | | | | |
| uc002zxy.1 | 224450352 | 224565032 | 11468 | | | | | | |
| uc002zxz.1 | 224533792 | 224565032 | 3124 | | | | | | |
| uc002zya.1 | 224591492 | 225066952 | 47546 | | | | | | |

Fig. 4b

| #name | txStart | txEnd | size | Rank size order | Comparative genomics peak order | standard | actual | fusion gene name | gene size |
|---|---|---|---|---|---|---|---|---|---|
| uc002zyb.1 | 22459149 | 22506705 | 47556 | | | | | | |
| uc002zyc.1 | 22459149 | 22506705 | 47556 | | | | | | |
| uc002zyd.1 | 22459149 | 22506705 | 47556 | | | | | | |
| uc002zye.1 | 22463942 | 22475571 | 11629 | | | | | | |
| uc002zyf.1 | 22463942 | 22475571 | 11629 | | | | | | |
| uc002zyg.1 | 22465745 | 22473342 | 7597 | | | | | | |
| uc002zyh.1 | 22506689 | 22511201 | 4512 | | | | | | |
| uc002zyi.1 | 22506689 | 22511201 | 4512 | | | | | | |
| uc002zyj.1 | 22506689 | 22511315 | 4626 | | | | | | |
| uc002zyk.1 | 22506909 | 22511201 | 4292 | | | | | | |
| uc002zyl.1 | 22529058 | 22556211 | 27153 | | | | | | |
| uc002zym.1 | 22529058 | 22557389 | 28331 | | | | | | |
| uc002zyn.1 | 22529058 | 22557389 | 28331 | | | | | | |
| uc002zyo.1 | 22529058 | 22557389 | 28331 | | | | | | |
| uc002zyp.1 | 22530149 | 22557389 | 27240 | | | | | | |
| uc002zyq.1 | 22566564 | 22567405 | 841 | | | | | | |
| uc002zyr.1 | 22566564 | 22567409 | 845 | | | | | | |
| uc002zys.1 | 22566612 | 22571117 | 4505 | | | | | | |
| uc002zyt.1 | 22570051 | 22570096 | 45 | | | | | | |
| uc002zyu.1 | 22570104 | 22570147 | 43 | | | | | | |
| uc002zyv.1 | 22570744 | 22570774 | 30 | | | | | | |
| uc002zyw.1 | 22629608 | 22633383 | 3775 | | | | | | |
| uc002zyx.1 | 22629608 | 22633383 | 3775 | | | | | | |
| uc002zyy.1 | 22639088 | 22644721 | 5633 | | | | | | |
| uc002zyz.1 | 22643559 | 22646637 | 3078 | | | | | | |
| uc002zza.1 | 22643559 | 22652019 | 8460 | | | | | | |
| uc002zzb.1 | 22652323 | 22656098 | 3775 | | | | | | |
| uc002zzc.1 | 22652323 | 22656098 | 3775 | | | | | | |
| uc002zzd.1 | 22670594 | 22677258 | 6664 | | | | | | |
| uc002zze.1 | 22706140 | 22714231 | 8091 | | | | | | |
| uc002zzf.1 | 22706140 | 22714231 | 8091 | | | | | | |
| uc002zzg.1 | 22706140 | 22714231 | 8091 | | | | | | |
| uc002zzh.1 | 22715937 | 22731899 | 15962 | | | | | | |

Fig. 4c

| #name | txStart | txEnd | size | fusion gene name | Rank size order | Comparative genomics peak order | standard | actual | gene size |
|---|---|---|---|---|---|---|---|---|---|
| uc002zzi.1 | 22737764 | 22904596 | 166832 | | | | | | |
| uc002zzj.1 | 22737764 | 22904596 | 166832 | | | | | | |
| uc002zzk.1 | 22737867 | 22782823 | 44956 | | | | | | |
| uc002zzl.1 | 22737867 | 22904596 | 166729 | | | | | | |
| uc002zzm.1 | 22881971 | 22894518 | 12547 | | | | | | |
| uc002zzn.1 | 22907443 | 22915074 | 7631 | | | | | | |
| uc002zzo.1 | 22945638 | 22971028 | 25390 | | | | | | |
| uc002zzp.1 | 22945638 | 22971028 | 25390 | | | | | | |
| uc002zzq.1 | 22945638 | 22971028 | 25390 | | | | | | |
| uc002zzr.1 | 22945638 | 22971028 | 25390 | | | | | | |
| uc002zzs.1 | 22977795 | 22991062 | 13267 | | | | | | |
| uc002zzt.1 | 22978722 | 22978761 | 39 | | | | | | |
| uc002zzu.1 | 22979617 | 22979786 | 169 | | | | | | |

Fig. 4d

Chromosome position represented
chr11:100,693,404-102,713,675
Total number of genes: 20

Total units is always 42

| #name | txStart | txEnd | | size | fusion gene name | Rank size order | Comparative genomics peak order | standard | actual | gene size |
|---|---|---|---|---|---|---|---|---|---|---|
| uc001pgk.1 | 1000827582 | 1000959869 | | 132287 | | | | | | |
| uc001pgl.1 | 1012666614 | 1012292463 | | 25849 | | | | | | |
| uc001pgm.1 | 1012290955 | 1013770003 | | 86048 | | | | | | |
| uc001pgn.1 | 1012298553 | 1013770003 | | 78450 | | | | | | |
| uc001pgo.1 | 1014233383 | 1014152052 | | 28669 | | | | | | |
| uc001pgp.1 | 1014233383 | 1014159356 | | 35973 | | | | | | |
| uc001pgq.1 | 1014234408 | 1014159356 | | 35948 | | | | | | |
| uc001pgr.1 | 1014183826 | 1014185778 | | 1952 | | | | | | |
| uc001pgs.1 | 1014186540 | 1016109358 | | 122818 | | | | | | |
| uc001pgt.1 | 1014186540 | 1016109358 | | 122818 | | | | | | |
| uc001pgu.1 | 1014186540 | 1016109358 | | 122818 | | | | | | |
| uc001pgv.1 | 1014186540 | 1016109358 | | 122818 | | | | | | |
| uc001pgw.1 | 1014190084 | 1016109358 | | 119274 | | | | | | |

| | | | | | fusion gene name | Rank size order | Rank order of peak size | Number of units covered by gene +/-3 | Distance from gene to peak | Gene size in units |
|---|---|---|---|---|---|---|---|---|---|---|
| uc001pgx.1 | 1016693403 | 1017713675 | uc001pgx.1 | 20272 | BIRC3 | b5 | 1 | 8 | 0 | 2 |
| uc001pgy.1 | 1017723175 | 1017754611 | | 31436 | | | | | | |
| uc001pgz.1 | 1017723319 | 1017754611 | | 31292 | | | | | | |
| uc001pha.1 | 1017772265 | 1018828985 | | 56720 | | | | | | |
| uc001phb.1 | 1018964448 | 1019906688 | | 10240 | | | | | | |
| uc001phc.1 | 1019952775 | 1020001273 | | 48498 | | | | | | |
| uc001phd.1 | 1020067624 | 1020081678 | | 14054 | | | | | | |
| uc001phe.1 | 1020088539 | 1020100868 | | 12329 | | | | | | |
| uc001phf.1 | 1021128063 | 1021129393 | | 1330 | | | | | | |
| uc001phg.1 | 1021146443 | 1021156554 | | 10111 | | | | | | |
| uc001phh.1 | 1021159616 | 1022212707 | | 53091 | | | | | | |

Fig. 5a

| #name | txStart | txEnd | size | fusion gene name | Rank size order | Comparative genomics peak order | standard | actual | gene size |
|---|---|---|---|---|---|---|---|---|---|
| uc001phi.1 | 102165860 | 102174104 | 8244 | | | | | | |
| uc001phj.1 | 102211737 | 102219552 | 7815 | | | | | | |
| uc001phk.1 | 102238673 | 102250922 | 12249 | | | | | | |
| uc001phl.1 | 102318933 | 102331672 | 12739 | | | | | | |
| uc001phm.1 | 102438030 | 102468079 | 30049 | | | | | | |
| uc001phn.1 | 102485369 | 102855801 | 370432 | | | | | | |
| uc001pho.1 | 102575166 | 102855801 | 280635 | | | | | | |

Fig. 5b

Chromosome position represented
chr22:16,546,987-18,659,239
Total number of genes: 36

Total units is always 42

| #name | txStart | txEnd | size | fusion gene name | Rank size order | Comparative genomics peak order | standard | actual | gene size |
|---|---|---|---|---|---|---|---|---|---|
| uc002zmu.1 | 16491681 | 16566499 | 74818 | | | | | | |
| uc002zmv.1 | 16501484 | 16566499 | 65015 | | | | | | |
| uc002zmw.1 | 16501484 | 16591989 | 90505 | | | | | | |
| uc002zmx.1 | 16501484 | 16591989 | 90505 | | | | | | |
| uc002zmy.1 | 16501484 | 16591989 | 90505 | | | | | | |
| uc002zmz.1 | 16551751 | 16591989 | 40238 | | | | | | |
| uc002zna.1 | 16569550 | 16591989 | 22439 | | | | | | |
| uc002znb.1 | 16594960 | 16597982 | 3022 | | | | | | |
| uc002znc.1 | 16596905 | 16636779 | 39874 | | | | | | |
| uc002znd.1 | 16596905 | 16637258 | 40353 | | | | | | |
| uc002zne.1 | 16596905 | 16637258 | 40353 | | | | | | |
| uc002znf.1 | 16596905 | 16637258 | 40353 | | | | | | |
| uc002zng.1 | 16650415 | 16694635 | 44220 | | | | | | |
| uc002znh.1 | 16697100 | 16769652 | 72552 | | | | | | |
| uc002zni.1 | 16702716 | 16705248 | 2532 | | | | | | |
| uc002znj.1 | 16703024 | 16765513 | 62489 | | | | | | |
| uc002znk.1 | 16703024 | 16769652 | 66628 | | | | | | |
| uc002znl.1 | 16703024 | 16864267 | 161243 | | | | | | |
| uc002znm.1 | 16722982 | 16756670 | 33688 | | | | | | |
| uc002znn.1 | 16754250 | 16887325 | 133075 | | | | | | |
| uc002zno.1 | 16892150 | 16900734 | 8584 | | | | | | |
| uc002znp.1 | 16940704 | 16952207 | 11503 | | | | | | |
| uc002znq.1 | 16940773 | 16952207 | 11434 | | | | | | |
| uc002znr.1 | 16940773 | 16994498 | 53725 | | | | | | |
| uc002zns.1 | 16940821 | 16941541 | 720 | | | | | | |
| uc002znt.1 | 16941061 | 16952207 | 11146 | | | | | | |
| uc002znu.1 | 16973558 | 16989261 | 15703 | | | | | | |
| uc002znv.1 | 16973558 | 16994498 | 20940 | | | | | | |
| uc002znw.1 | 16983873 | 16994498 | 10625 | | | | | | |

Fig. 6a

| #name | txStart | txEnd | size | fusion gene name | Rank size order | Comparative genomics peak order | standard | actual | gene size |
|---|---|---|---|---|---|---|---|---|---|
| uc002znx.1 | 16989120 | 17009275 | 20155 | | | | | | |
| uc002zny.1 | 17012757 | 17040162 | 27405 | | | | | | |
| uc002znz.1 | 17040804 | 17065242 | 24438 | | | | | | |
| uc002zoa.1 | 17141201 | 17159474 | 18273 | | | | | | |
| uc002zob.1 | 17141201 | 17172992 | 31791 | | | | | | |
| uc002zoc.1 | 17214323 | 17219322 | 4999 | | | | | | |
| uc002zod.1 | 17217630 | 17227477 | 9847 | | | | | | |
| uc002zoe.1 | 17220391 | 17227477 | 7086 | | | | | | |
| uc002zof.1 | 17227155 | 17229294 | 2139 | | | | | | |
| uc002zog.1 | 17273540 | 17279601 | 6061 | | | | | | |
| uc002zoh.1 | 17273778 | 17279601 | 5823 | | | | | | |
| uc002zoi.1 | 17273778 | 17279601 | 5823 | | | | | | |
| uc002zoj.1 | 17280294 | 17303806 | 23512 | | | | | | |
| uc002zok.1 | 17280294 | 17304066 | 23772 | | | | | | |
| uc002zol.1 | 17280294 | 17304066 | 23772 | | | | | | |
| uc002zom.1 | 17338026 | 17362141 | 24115 | | | | | | |
| uc002zon.1 | 17338026 | 17398742 | 60716 | | | | | | |
| uc002zoo.1 | 17365786 | 17382299 | 16513 | | | | | | |
| uc002zop.1 | 17386062 | 17386616 | 554 | | | | | | |
| uc002zoq.1 | 17403794 | 17489967 | 86173 | | | | | | |
| uc002zor.1 | 17403794 | 17489967 | 86173 | | | | | | |
| uc002zos.1 | 17413674 | 17414909 | 1235 | | | | | | |
| uc002zot.1 | 17497791 | 17512146 | 14355 | | | | | | |
| uc002zou.1 | 17497791 | 17512190 | 14399 | | | | | | |
| uc002zov.1 | 17497791 | 17512190 | 14399 | | | | | | |
| uc002zow.1 | 17498789 | 17500136 | 1347 | | | | | | |
| uc002zox.1 | 17516503 | 17517796 | 1293 | | | | | | |
| uc002zoy.1 | 17543394 | 17546034 | 2640 | | | | | | |
| uc002zoz.1 | 17543394 | 17546285 | 2891 | | | | | | |
| uc002zpa.1 | 17543394 | 17546285 | 2891 | | | | | | |

Fig. 6b

| #name | txStart | txEnd | size | fusion gene name | Rank size order | Comparative genomics peak order / Rank order of peak size | standard Number of units covered by gene +/-3 | actual Distance from gene to peak | gene size / Gene size in units |
|---|---|---|---|---|---|---|---|---|---|
| uc002zpb.1 | 17546986 | 17659239 uc002zpb.1 | 112253 | CLTCL1 | 2 | 1 | 8 | 1 | 2 |
| uc002zpc.1 | 17546986 | 17659239 | 112253 | | | | | | |
| uc002zpd.1 | 17563776 | 17583344 | 19568 | | | | | | |
| uc002zpe.1 | 17563872 | 17583344 | 19472 | | | | | | |
| uc002zpf.1 | 17698223 | 17799219 | 100996 | | | | | | |
| uc002zpg.1 | 17800035 | 17803596 | 3561 | | | | | | |
| uc002zph.1 | 17800101 | 17803596 | 3495 | | | | | | |
| uc002zpi.1 | 17808409 | 17815220 | 6811 | | | | | | |
| uc002zpj.1 | 17809614 | 17811418 | 1804 | | | | | | |
| uc002zpk.1 | 17810894 | 17815220 | 4326 | | | | | | |
| uc002zpl.1 | 17815415 | 17817628 | 2213 | | | | | | |
| uc002zpm.1 | 17817700 | 17846726 | 29026 | | | | | | |
| uc002zpn.1 | 17817700 | 17846726 | 29026 | | | | | | |
| uc002zpo.1 | 17817700 | 17846726 | 29026 | | | | | | |
| uc002zpp.1 | 17818143 | 17846726 | 28583 | | | | | | |
| uc002zpq.1 | 17839917 | 17840033 | 116 | | | | | | |
| uc002zpr.1 | 17847415 | 17888135 | 40720 | | | | | | |
| uc002zps.1 | 17847415 | 17888135 | 40720 | | | | | | |
| uc002zpt.1 | 17847415 | 17888135 | 40720 | | | | | | |
| uc002zpu.1 | 17890549 | 17892860 | 2311 | | | | | | |
| uc002zpv.1 | 18081986 | 18092297 | 10311 | | | | | | |
| uc002zpw.1 | 18084742 | 18091102 | 6360 | | | | | | |
| uc002zpx.1 | 18084742 | 18092297 | 7555 | | | | | | |
| uc002zpy.1 | 18088290 | 18092297 | 4007 | | | | | | |
| uc002zpz.1 | 18089950 | 18092297 | 2347 | | | | | | |
| uc002zqa.1 | 18124225 | 18134855 | 10630 | | | | | | |
| uc002zqb.1 | 18124225 | 18147068 | 22843 | | | | | | |
| uc002zqc.1 | 18124225 | 18151112 | 26887 | | | | | | |
| uc002zqd.1 | 18155933 | 18222329 | 66396 | | | | | | |
| uc002zqe.1 | 18155933 | 18222339 | 66406 | | | | | | |

Fig. 6c

| #name | txStart | txEnd | size | fusion gene name | Rank size order | Comparative genomics peak order | standard | actual | gene size |
|---|---|---|---|---|---|---|---|---|---|
| uc002zqf.1 | 18155933 | 18222462 | 66529 | | | | | | |
| uc002zqg.1 | 18213660 | 18222339 | 8679 | | | | | | |
| uc002zqh.1 | 18213660 | 18222371 | 8711 | | | | | | |
| uc002zqi.1 | 18213660 | 18222462 | 8802 | | | | | | |
| uc002zqj.1 | 18243039 | 18300076 | 57037 | | | | | | |
| uc002zqk.1 | 18243039 | 18309359 | 66320 | | | | | | |
| uc002zql.1 | 18243039 | 18309359 | 66320 | | | | | | |
| uc002zqm.1 | 18243039 | 18309359 | 66320 | | | | | | |
| uc002zqn.1 | 18243039 | 18309359 | 66320 | | | | | | |
| uc002zqo.1 | 18243039 | 18309359 | 66320 | | | | | | |
| uc002zqp.1 | 18243039 | 18309359 | 66320 | | | | | | |
| uc002zqq.1 | 18243046 | 18248870 | 5824 | | | | | | |
| uc002zqr.1 | 18243046 | 18309359 | 66313 | | | | | | |
| uc002zqs.1 | 18261782 | 18301049 | 39267 | | | | | | |
| uc002zqt.1 | 18309308 | 18333168 | 23860 | | | | | | |
| uc002zqu.1 | 18309308 | 18336530 | 27222 | | | | | | |
| uc002zqv.1 | 18309308 | 18336530 | 27222 | | | | | | |
| uc002zqw.1 | 18309308 | 18336530 | 27222 | | | | | | |
| uc002zqx.1 | 18319053 | 18336530 | 17477 | | | | | | |
| uc002zqy.1 | 18337418 | 18346734 | 9316 | | | | | | |
| uc002zqz.1 | 18337418 | 18384309 | 46891 | | | | | | |
| uc002zra.1 | 18347519 | 18358335 | 10816 | | | | | | |
| uc002zrb.1 | 18384536 | 18433447 | 48911 | | | | | | |
| uc002zrc.1 | 18388630 | 18433447 | 44817 | | | | | | |
| uc002zrd.1 | 18388630 | 18433447 | 44817 | | | | | | |
| uc002zre.1 | 18388636 | 18423764 | 35128 | | | | | | |
| uc002zrf.1 | 18388636 | 18433447 | 44811 | | | | | | |
| uc002zrg.1 | 18404282 | 18429206 | 24924 | | | | | | |
| uc002zrh.1 | 18404282 | 18433447 | 29165 | | | | | | |
| uc002zri.1 | 18447833 | 18479400 | 31567 | | | | | | |
| uc002zrj.1 | 18454684 | 18479400 | 24716 | | | | | | |
| uc002zrk.1 | 18479397 | 18484768 | 5371 | | | | | | |
| uc002zrl.1 | 18479397 | 18484768 | 5371 | | | | | | |

Fig. 6d

| #name | txStart | txEnd | size | fusion gene name | Rank size order | Comparative genomics peak order | standard | actual | gene size |
|---|---|---|---|---|---|---|---|---|---|
| uc002zrm.1 | 18479397 | 18484768 | 5371 | | | | | | |
| uc002zrn.1 | 18479397 | 18484768 | 5371 | | | | | | |
| uc002zro.1 | 18485023 | 18494704 | 9681 | | | | | | |
| uc002zrp.1 | 18485023 | 18494706 | 9683 | | | | | | |
| uc002zrq.1 | 18499364 | 18513974 | 14610 | | | | | | |
| uc002zrr.1 | 18499364 | 18515529 | 16165 | | | | | | |
| uc002zrs.1 | 18566251 | 18572441 | 6190 | | | | | | |
| uc002zrt.1 | 18574099 | 18574706 | 607 | | | | | | |
| uc002zru.1 | 18608937 | 18611207 | 2270 | | | | | | |
| uc002zrv.1 | 18608937 | 18635816 | 26879 | | | | | | |

Fig. 6e

Chromosome position represented
chr16:2,715,057-4,870,122
Total number of genes 61

Total units is always 42

| #name | txStart | txEnd | size | fusion gene name | Rank size order | Comparative genomics peak order | standard | actual | gene size |
|---|---|---|---|---|---|---|---|---|---|
| uc002crh.1 | 2727077 | 2734799 | 7722 | | | | | | |
| uc002cri.1 | 2727077 | 2740812 | 13735 | | | | | | |
| uc002crj.1 | 2742330 | 2758263 | 15933 | | | | | | |
| uc002crk.1 | 2742330 | 2761414 | 19084 | | | | | | |
| uc002crl.1 | 2742627 | 2758263 | 15636 | | | | | | |
| uc002crm.1 | 2761415 | 2767298 | 5883 | | | | | | |
| uc002crn.1 | 2761415 | 2767298 | 5883 | | | | | | |
| uc002cro.1 | 2773954 | 2776709 | 2755 | | | | | | |
| uc002crp.1 | 2773954 | 2776709 | 2755 | | | | | | |
| uc002crq.1 | 2773954 | 2777950 | 3996 | | | | | | |
| uc002crr.1 | 2807164 | 2811719 | 4555 | | | | | | |
| uc002crs.1 | 2807164 | 2811719 | 4555 | | | | | | |
| uc002crt.1 | 2807164 | 2811719 | 4555 | | | | | | |
| uc002cru.1 | 2820173 | 2822286 | 2113 | | | | | | |
| uc002crv.1 | 2829576 | 2831850 | 2274 | | | | | | |
| uc002crw.1 | 2829576 | 2832474 | 2898 | | | | | | |
| uc002crx.1 | 2829576 | 2832712 | 3136 | | | | | | |
| uc002cry.1 | 2842728 | 2848172 | 5444 | | | | | | |
| uc002crz.1 | 2842728 | 2848172 | 5444 | | | | | | |
| uc002csa.1 | 2873318 | 2889357 | 16039 | | | | | | |
| uc002csb.1 | 2901980 | 2930159 | 28179 | | | | | | |
| uc002csc.1 | 2901980 | 2941210 | 39230 | | | | | | |
| uc002csd.1 | 2901980 | 2941210 | 39230 | | | | | | |
| uc002cse.1 | 2927075 | 2941210 | 14135 | | | | | | |
| uc002csf.1 | 2954217 | 2957703 | 3486 | | | | | | |
| uc002csg.1 | 2954217 | 2958382 | 4165 | | | | | | |
| uc002csh.1 | 2954217 | 2958382 | 4165 | | | | | | |
| uc002csi.1 | 2954217 | 2958382 | 4165 | | | | | | |
| uc002csj.1 | 2959598 | 2963486 | 3888 | | | | | | |

Fig. 7a

| | | |
|---|---|---|
| uc002csk.1 | 2955598 | 2963486 | 3888 |
| uc002csl.1 | 2955598 | 2963486 | 3888 |
| uc002csm.1 | 2962792 | 2970475 | 7683 |
| uc002csn.1 | 2962792 | 2970475 | 7683 |
| uc002cso.1 | 2962792 | 2970475 | 7683 |
| uc002csp.1 | 2962792 | 2970475 | 7683 |
| uc002csq.1 | 2962792 | 2970475 | 7683 |
| uc002csr.1 | 2979055 | 2983506 | 4451 |
| uc002css.1 | 2980195 | 2984511 | 4316 |
| uc002cst.1 | 3002206 | 3004507 | 2301 |
| uc002csu.1 | 3004713 | 3008163 | 3450 |
| uc002csv.1 | 3010360 | 3012384 | 2024 |
| uc002csw.1 | 3010360 | 3012384 | 2024 |
| uc002csx.1 | 3012626 | 3014288 | 1662 |
| uc002csy.1 | 3012626 | 3014288 | 1662 |
| uc002csz.1 | 3012626 | 3014288 | 1662 |
| uc002cta.1 | 3014042 | 3017752 | 3710 |
| uc002ctb.1 | 3014093 | 3017752 | 3659 |
| uc002ctc.1 | 3014093 | 3017752 | 3659 |
| uc002ctd.1 | 3014093 | 3017752 | 3659 |
| uc002cte.1 | 3017687 | 3023004 | 5317 |
| uc002ctf.1 | 3017687 | 3025543 | 7856 |
| uc002ctg.1 | 3027251 | 3027801 | 550 |
| uc002cth.1 | 3036682 | 3050725 | 14043 |
| uc002cti.1 | 3037416 | 3046164 | 8748 |
| uc002ctj.1 | 3041996 | 3049337 | 7341 |
| uc002ctk.1 | 3055313 | 3059669 | 4356 |
| uc002ctl.1 | 3055313 | 3059669 | 4356 |
| uc002ctm.1 | 3055313 | 3059669 | 4356 |
| uc002ctn.1 | 3055313 | 3059669 | 4356 |
| uc002cto.1 | 3055313 | 3059669 | 4356 |
| uc002ctp.1 | 3055612 | 3059669 | 4057 |
| uc002ctq.1 | 3055622 | 3059669 | 4047 |
| uc002ctr.1 | 3055622 | 3059669 | 4047 |
| uc002cts.1 | 3055662 | 3059669 | 4007 |
| uc002ctt.1 | 3055663 | 3059669 | 4006 |

Fig. 7b

| | | |
|---|---|---|
| uc002ctu.1 | 3055785 | 3884 |
| uc002ctv.1 | 3078895 | 3967 |
| uc002ctw.1 | 3078895 | 3967 |
| uc002ctx.1 | 3078895 | 4343 |
| uc002cty.1 | 3078895 | 10399 |
| uc002ctz.1 | 3100461 | 5139 |
| uc002cua.1 | 3102563 | 7956 |
| uc002cub.1 | 3102563 | 7956 |
| uc002cuc.1 | 3118835 | 3209 |
| uc002cud.1 | 3125139 | 7129 |
| uc002cue.1 | 3125139 | 7667 |
| uc002cuf.1 | 3134220 | 5745 |
| uc002cug.1 | 3194247 | 939 |
| uc002cuh.1 | 3205562 | 985 |
| uc002cui.1 | 3212342 | 13068 |
| uc002cuj.1 | 3212342 | 13068 |
| uc002cuk.1 | 3212342 | 13068 |
| uc002cul.1 | 3212342 | 13068 |
| uc002cum.1 | 3212342 | 13068 |
| uc002cun.1 | 3232028 | 14600 |
| uc002cuo.1 | 3253802 | 3570 |
| uc002cup.1 | 3273487 | 3402 |
| uc002cuq.1 | 3273487 | 7973 |
| uc002cur.1 | 3280212 | 11189 |
| uc002cus.1 | 3288832 | 2569 |
| uc002cut.1 | 3295486 | 13089 |
| uc002cuu.1 | 3298332 | 1122 |
| uc002cuv.1 | 3298360 | 10215 |
| uc002cuw.1 | 3345889 | 1036 |
| uc002cux.1 | 3372085 | 18911 |
| uc002cuy.1 | 3372085 | 18911 |
| uc002cuz.1 | 3372085 | 18941 |
| uc002cva.1 | 3391244 | 3751 |
| uc002cvb.1 | 3391244 | 3800 |
| uc002cvc.1 | 3391244 | 8121 |
| uc002cvd.1 | 3426110 | 7381 |

Fig. 7c

| | | | Rank order of peak size | Number of units covered by gene +/-3 | Distance from gene to peak | Gene size in units |
|---|---|---|---|---|---|---|
| uc002cve.1 | 3433735 | 3473598 | | | | |
| uc002cvf.1 | 3448078 | 3476953 | | | | |
| uc002cvg.1 | 3466176 | 3473598 | | | | |
| uc002cvh.1 | 3474699 | 3476953 | | | | |
| uc002cvi.1 | 3483484 | 3485422 | | | | |
| uc002cvj.1 | 3490963 | 3526826 | | | | |
| uc002cvk.1 | 3490963 | 3527670 | | | | |
| uc002cvl.1 | 3490963 | 3527670 | | | | |
| uc002cvm.1 | 3499894 | 3527670 | | | | |
| uc002cvn.1 | 3523437 | 3524256 | | | | |
| uc002cvo.1 | 3529036 | 3567393 | | | | |
| uc002cvp.1 | 3571183 | 3601586 | | | | |
| uc002cvq.1 | 3590622 | 3601586 | | | | |
| uc002cvr.1 | 3642940 | 3648097 | | | | |
| uc002cvs.1 | 3648038 | 3668306 | | | | |
| uc002cvt.1 | 3648038 | 3707514 | | | | |
| uc002cvu.1 | 3650743 | 3655459 | | | | |
| uc002cvv.1 | 3715056 | 3870122 | | | | |
| uc002cvw.1 | 3715056 | 3870122 | uc002cvw.1 CREBBP | 1 | 2 | 10 | 1 | 4 |
| uc002cvx.1 | 3952652 | 4106187 | | | | |
| uc002cvy.1 | 4179376 | 4232077 | | | | |
| uc002cvz.1 | 4179376 | 4232077 | | | | |
| uc002cwa.1 | 4235826 | 4243791 | | | | |
| uc002cwb.1 | 4247187 | 4263011 | | | | |
| uc002cwc.1 | 4322216 | 4329599 | | | | |
| uc002cwd.1 | 4330252 | 4341301 | | | | |
| uc002cwe.1 | 4330252 | 4397686 | | | | |
| uc002cwf.1 | 4330252 | 4406963 | | | | |
| uc002cwg.1 | 4344545 | 4405899 | | | | |
| uc002cwh.1 | 4344545 | 4406963 | | | | |
| uc002cwi.1 | 4347376 | 4397686 | | | | |
| uc002cwj.1 | 4361849 | 4373530 | | | | |
| uc002cwk.1 | 4415882 | 4446776 | | | | |

Fig. 7d

| | | |
|---|---|---|
| uc002cwl.1 | 4415882 | 4446776 | 30894 |
| uc002cwm.1 | 4451695 | 4464533 | 12838 |
| uc002cwn.1 | 4451695 | 4464626 | 12931 |
| uc002cwo.1 | 4451695 | 4464897 | 13202 |
| uc002cwp.1 | 4451695 | 4466308 | 14613 |
| uc002cwq.1 | 4466446 | 4500349 | 33903 |
| uc002cwr.1 | 4466446 | 4500349 | 33903 |
| uc002cws.1 | 4466446 | 4500349 | 33903 |
| uc002cwt.1 | 4485859 | 4500349 | 14490 |
| uc002cwu.1 | 4500677 | 4504857 | 4180 |
| uc002cwv.1 | 4500677 | 4528472 | 27795 |
| uc002cww.1 | 4500677 | 4528817 | 28140 |
| uc002cwx.1 | 4598885 | 4604871 | 5986 |
| uc002cwy.1 | 4602083 | 4604870 | 2787 |
| uc002cwz.1 | 4614853 | 4677579 | 62726 |
| uc002cxa.1 | 4614853 | 4680974 | 66121 |
| uc002cxb.1 | 4614853 | 4680974 | 66121 |
| uc002cxc.1 | 4624330 | 4630625 | 6295 |
| uc002cxd.1 | 4677580 | 4680975 | 3395 |
| uc002cxe.1 | 4683716 | 4685846 | 2130 |
| uc002cxf.1 | 4683716 | 4685857 | 2141 |
| uc002cxg.1 | 4686513 | 4690167 | 3654 |
| uc002cxh.1 | 4686513 | 4690305 | 3792 |
| uc002cxi.1 | 4686513 | 4718080 | 31567 |
| uc002cxj.1 | 4686513 | 4724164 | 37651 |
| uc002cxk.1 | 4686513 | 4724221 | 37708 |
| uc002cxl.1 | 4686513 | 4724221 | 37708 |
| uc002cxm.1 | 4689755 | 4724221 | 34466 |
| uc002cxn.1 | 4724289 | 4739398 | 15109 |
| uc002cxo.1 | 4740815 | 4756078 | 15263 |
| uc002cxp.1 | 4740815 | 4757167 | 16352 |
| uc002cxq.1 | 4767674 | 4778348 | 10674 |
| uc002cxr.1 | 4767674 | 4778348 | 10674 |
| uc002cxs.1 | 4778398 | 4786283 | 7885 |
| uc002cxt.1 | 4778457 | 4786283 | 7826 |
| uc002cxu.1 | 4786969 | 4792164 | 5195 |

Fig. 7e

| | | |
|---|---|---|
| uc002cxv.1 | 4786969 | 4792675 |
| uc002cxw.1 | 4786969 | 4792675 |
| uc002cxx.1 | 4793204 | 4837285 |
| uc002cxy.1 | 4793204 | 4837285 |
| uc002cxz.1 | 4794523 | 4836212 |
| uc002cya.1 | 4794523 | 4837285 |
| uc002cyb.1 | 4837912 | 4872364 |
| uc002cyc.1 | 4842077 | 4872364 |

| |
|---|
| 5706 |
| 5706 |
| 44081 |
| 44081 |
| 41689 |
| 42762 |
| 34452 |
| 30287 |

Fig. 7f

Chromosome position represented
chr12:55,196,638-57,200,567
Total number of genes  45

Total units is always 42

| #name | txStart | txEnd | size | fusion gene name | Rank size order | Comparative genomics peak order | standard | actual | gene size |
|---|---|---|---|---|---|---|---|---|---|
| uc001slm.1 | 55201992 | 55269875 | 67883 | | | | | | |
| uc001sln.1 | 55272080 | 55276158 | 4078 | | | | | | |
| uc001slo.1 | 55275646 | 55282243 | 6597 | | | | | | |
| uc001slp.1 | 55275646 | 55310262 | 34616 | | | | | | |
| uc001slq.1 | 55275646 | 55316430 | 40784 | | | | | | |
| uc001slr.1 | 55318225 | 55326119 | 7894 | | | | | | |
| uc001sls.1 | 55323730 | 55323805 | 75 | | | | | | |
| uc001slt.1 | 55325077 | 55325152 | 75 | | | | | | |
| uc001slu.1 | 55343648 | 55368156 | 24508 | | | | | | |
| uc001slv.1 | 55343648 | 55368156 | 24508 | | | | | | |
| uc001slw.1 | 55343648 | 55368314 | 24666 | | | | | | |
| uc001slx.1 | 55366439 | 55368314 | 1875 | | | | | | |
| uc001sly.1 | 55392485 | 55405318 | 12833 | | | | | | |
| uc001slz.1 | 55392485 | 55405318 | 12833 | | | | | | |
| uc001sma.1 | 55392485 | 55405350 | 12865 | | | | | | |
| uc001smb.1 | 55392485 | 55405350 | 12865 | | | | | | |
| uc001smc.1 | 55392485 | 55405350 | 12865 | | | | | | |
| uc001smd.1 | 55411630 | 55432413 | 20783 | | | | | | |
| uc001sme.1 | 55423037 | 55432413 | 9376 | | | | | | |
| uc001smf.1 | 55423565 | 55432413 | 8848 | | | | | | |
| uc001smg.1 | 55443374 | 55467841 | 24467 | | | | | | |
| uc001smh.1 | 55603883 | 55614312 | 10429 | | | | | | |
| uc001smi.1 | 55631485 | 55638370 | 6885 | | | | | | |
| uc001smj.1 | 55631485 | 55638370 | 6885 | | | | | | |
| uc001smk.1 | 55674621 | 55676736 | 2115 | | | | | | |
| uc001sml.1 | 55678884 | 55686497 | 7613 | | | | | | |
| uc001smm.1 | 55690050 | 55695860 | 5810 | | | | | | |
| uc001smn.1 | 55690050 | 55696592 | 6542 | | | | | | |
| uc001smo.1 | 55690050 | 55696592 | 6542 | | | | | | |

Fig. 8a

| #name | txStart | txEnd | size | fusion gene name | Rank size order | Comparative genomics peak order | standard | actual | gene size |
|---|---|---|---|---|---|---|---|---|---|
| uc001smp.1 | 55690050 | 55696592 | 6542 | | | | | | |
| uc001smq.1 | 55690050 | 55696592 | 6542 | | | | | | |
| uc001smr.1 | 55690050 | 55696592 | 6542 | | | | | | |
| uc001sms.1 | 55690050 | 55696592 | 6542 | | | | | | |
| uc001smt.1 | 55690050 | 55696592 | 6542 | | | | | | |
| uc001smu.1 | 55690050 | 55696592 | 6542 | | | | | | |
| uc001smv.1 | 55690050 | 55696592 | 6542 | | | | | | |
| uc001smw.1 | 55708567 | 55730160 | 21593 | | | | | | |
| uc001smx.1 | 55735692 | 55758810 | 23118 | | | | | | |
| uc001smy.1 | 55735692 | 55758810 | 23118 | | | | | | |
| uc001smz.1 | 55768943 | 55775526 | 6583 | | | | | | |
| uc001sna.1 | 55775459 | 55791428 | 15969 | | | | | | |
| uc001snb.1 | 55808548 | 55830109 | 21561 | | | | | | |
| uc001snc.1 | 55808548 | 55835625 | 27077 | | | | | | |
| uc001snd.1 | 55808548 | 55893392 | 84844 | | | | | | |
| uc001sne.1 | 55896844 | 55906493 | 9649 | | | | | | |
| uc001snf.1 | 55909818 | 55914981 | 5163 | | | | | | |
| uc001sng.1 | 55909818 | 55914981 | 5163 | | | | | | |
| uc001snh.1 | 55909818 | 55914981 | 5163 | | | | | | |
| uc001sni.1 | 55910135 | 55914981 | 4846 | | | | | | |
| uc001snj.1 | 55910412 | 55914981 | 4569 | | | | | | |
| uc001snk.1 | 55910415 | 55914981 | 4566 | | | | | | |
| uc001snl.1 | 55910433 | 55914981 | 4548 | | | | | | |
| uc001snm.1 | 55914952 | 55917202 | 2250 | | | | | | |
| uc001snn.1 | 55914952 | 55918409 | 3457 | | | | | | |
| uc001sno.1 | 55914952 | 55920742 | 5790 | | | | | | |
| uc001snp.1 | 55923508 | 55931236 | 7728 | | | | | | |
| uc001snq.1 | 55923508 | 55931236 | 7728 | | | | | | |
| uc001snr.1 | 55933813 | 55977083 | 43270 | | | | | | |
| uc001sns.1 | 55933813 | 56111055 | 177242 | | | | | | |
| uc001snt.1 | 55933813 | 56111055 | 177242 | | | | | | |
| uc001snu.1 | 55952586 | 55960580 | 7994 | | | | | | |
| uc001snv.1 | 56114809 | 56130876 | 16067 | | | | | | |

Fig. 8b

| #name | txStart | txEnd | | size | fusion gene name | Rank size order | Comparative genomics peak order | standard | actual | gene size |
|---|---|---|---|---|---|---|---|---|---|---|
| uc001snw.1 | 56135362 | 56138058 | | 2696 | | | | | | |
| uc001snx.1 | 56140200 | 56152312 | | 12112 | | | | | | |
| uc001sny.1 | 56152304 | 56155023 | | 2719 | | | | | | |
| uc001snz.1 | 56152304 | 56157995 | | 5691 | | | | | | |
| uc001soa.1 | 56152304 | 56157995 | | 5691 | | | | | | |
| uc001sob.1 | 56152304 | 56159691 | | 7387 | | | | | | |
| uc001soc.1 | 56152304 | 56159900 | | 7596 | | | | | | |
| uc001sod.1 | 56152304 | 56168864 | | 16560 | | | | | | |
| uc001soe.1 | 56154091 | 56168864 | | 14773 | | | | | | |
| uc001sof.1 | 56167343 | 56197601 | | 30258 | | | | | | |
| uc001sog.1 | 56167986 | 56196700 | | 28714 | | | | | | |
| uc001soh.1 | 56192800 | 56196697 | | 3897 | | | | | | |
| uc001soi.1 | 56196637 | 56200567 | uc001sol.1 | 3930 | DDIT3 | b5 | 1 | | | |
| uc001soj.1 | 56202925 | 56210198 | | 7273 | | | | | | |
| uc001sok.1 | 56205397 | 56209379 | | 3982 | | | | | | |
| uc001sol.1 | 56206615 | 56210198 | | 3583 | | | | | | |
| uc001som.1 | 56210360 | 56227245 | | 16885 | | | | | | |
| uc001son.1 | 56210360 | 56227245 | | 16885 | | | | | | |
| uc001soo.1 | 56210360 | 56227245 | | 16885 | | | | | | |
| uc001sop.1 | 56210360 | 56227245 | | 16885 | | | | | | |
| uc001soq.1 | 56230113 | 56264821 | | 34708 | | | | | | |
| uc001sor.1 | 56264955 | 56266678 | | 1723 | | | | | | |
| uc001sos.1 | 56271323 | 56283298 | | 11975 | | | | | | |
| uc001sot.1 | 56271323 | 56283465 | | 12142 | | | | | | |
| uc001sou.1 | 56284870 | 56287663 | | 2793 | | | | | | |
| uc001sov.1 | 56284870 | 56289850 | | 4980 | | | | | | |
| uc001sow.1 | 56284870 | 56289850 | | 4980 | | | | | | |
| uc001sox.1 | 56284873 | 56289850 | | 4977 | | | | | | |
| uc001soy.1 | 56290367 | 56295762 | | 5395 | | | | | | |
| uc001soz.1 | | | | | | | | | | |

| Rank order of peak size | Number of units covered by gene +/-3 | Distance from gene to peak | Gene size in units |
|---|---|---|---|
| 1 | 7 | 1 | 1 |

Fig. 8c

| #name | txStart | txEnd | size | fusion gene name | Rank size order | Comparative genomics peak order | standard | actual | gene size |
|---|---|---|---|---|---|---|---|---|---|
| uc001spa.1 | 56291484 | 56297293 | 5809 | | | | | | |
| uc001spb.1 | 56291484 | 56297293 | 5809 | | | | | | |
| uc001spc.1 | 56292388 | 56298095 | 5707 | | | | | | |
| uc001spd.1 | 56294043 | 56297293 | 3250 | | | | | | |
| uc001spe.1 | 56299959 | 56306201 | 6242 | | | | | | |
| uc001spf.1 | 56299959 | 56306201 | 6242 | | | | | | |
| uc001spg.1 | 56305817 | 56313252 | 7435 | | | | | | |
| uc001sph.1 | 56309380 | 56312718 | 3338 | | | | | | |
| uc001spi.1 | 56309380 | 56313252 | 3872 | | | | | | |
| uc001spj.1 | 56374152 | 56401607 | 27455 | | | | | | |
| uc001spk.1 | 56374152 | 56401607 | 27455 | | | | | | |
| uc001spl.1 | 56374152 | 56401607 | 27455 | | | | | | |
| uc001spm.1 | 56374152 | 56401607 | 27455 | | | | | | |
| uc001spn.1 | 56374152 | 56401607 | 27455 | | | | | | |
| uc001spo.1 | 56403839 | 56405715 | 1876 | | | | | | |
| uc001spp.1 | 56405260 | 56418296 | 13036 | | | | | | |
| uc001spq.1 | 56405260 | 56418296 | 13036 | | | | | | |
| uc001spr.1 | 56405260 | 56422207 | 16947 | | | | | | |
| uc001sps.1 | 56406326 | 56408397 | 2071 | | | | | | |
| uc001spt.1 | 56425050 | 56428293 | 3243 | | | | | | |
| uc001spu.1 | 56428016 | 56428264 | 248 | | | | | | |
| uc001spv.1 | 56428269 | 56432431 | 4162 | | | | | | |
| uc001spw.1 | 56428269 | 56432431 | 4162 | | | | | | |
| uc001spx.1 | 56435166 | 56439956 | 4790 | | | | | | |
| uc001spy.1 | 56437733 | 56439956 | 2223 | | | | | | |
| uc001spz.1 | 56442383 | 56447243 | 4860 | | | | | | |
| uc001sqa.1 | 56442383 | 56447243 | 4860 | | | | | | |
| uc001sqb.1 | 56444427 | 56445735 | 1308 | | | | | | |
| uc001sqc.1 | 56444427 | 56445735 | 1308 | | | | | | |
| uc001sqd.1 | 56448520 | 56452602 | 4082 | | | | | | |
| uc001sqe.1 | 56448520 | 56452602 | 4082 | | | | | | |
| uc001sqf.1 | 56452649 | 56462591 | 9942 | | | | | | |
| uc001sqg.1 | 56452649 | 56462591 | 9942 | | | | | | |

Fig. 8d

| #name | txStart | txEnd | size | fusion gene name | Rank size order | Comparative genomics peak order | standard | actual | gene size |
|---|---|---|---|---|---|---|---|---|---|
| uc001sqh.1 | 56462825 | 56476784 | 13959 | | | | | | |
| uc001sqj.1 | 56462825 | 56476784 | 13959 | | | | | | |
| uc001sqj.1 | 56477709 | 56496119 | 18410 | | | | | | |
| uc001sqk.1 | 56482209 | 56488742 | 6533 | | | | | | |
| uc001sql.1 | 56486204 | 56494276 | 8072 | | | | | | |
| uc001sqm.1 | 56499976 | 56527014 | 27038 | | | | | | |
| uc001sqn.1 | 56504707 | 56504729 | 22 | | | | | | |
| uc001sqo.1 | 56611573 | 56616114 | 4541 | | | | | | |
| uc001sqp.1 | 56621711 | 56637319 | 15608 | | | | | | |

Fig. 8e

Chromosome position represented
chr11:107,041,026-109,316,858
Total number of genes    14                    Total units is always 42

| #name | txStart | txEnd | size | fusion gene name | Rank size order | Comparative genomics peak order | standard | gene size |
|---|---|---|---|---|---|---|---|---|
| uc001pjm.1 | 106967286 | 107041900 | 74614 | | | | | |
| uc001pjn.1 | 106967286 | 107042715 | 75429 | | | | | |
| uc001pjp.1 | 107083310 | 107087997 | 4687 | | | | | |
| uc001pjq.1 | 107166926 | 107234890 | 67964 | | | | | |
| uc001pjr.1 | 107166927 | 107304229 | 137302 | | | | | |
| uc001pjs.1 | 107179943 | 107234890 | 54947 | | | | | |
| uc001pjt.1 | 107304486 | 107339418 | 34932 | | | | | |
| uc001pju.1 | 107384617 | 107482775 | 98158 | | | | | |
| uc001pjv.1 | 107384617 | 107483698 | 99081 | | | | | |
| uc001pjw.1 | 107497467 | 107512876 | 15409 | | | | | |
| uc001pjx.1 | 107497467 | 107519874 | 22407 | | | | | |
| uc001pjy.1 | 107497467 | 107523485 | 26018 | | | | | |
| uc001pjz.1 | 107533327 | 107598507 | 65180 | | | | | |
| uc001pka.1 | 107547082 | 107565274 | 18192 | | | | | |
| uc001pkb.1 | 107598768 | 107745036 | 146268 | | | | | |
| uc001pkc.1 | 107599465 | 107605301 | 5836 | | | | | |
| uc001pkd.1 | 107663328 | 107666577 | 3249 | | | | | |
| uc001pke.1 | 107663328 | 107745036 | 81708 | | | | | |
| uc001pkf.1 | 107663536 | 107671931 | 8395 | | | | | |
| uc001pkg.1 | 107672910 | 107709905 | 36995 | | | | | |
| uc001pkh.1 | 107758936 | 107843468 | 84532 | | | | | |
| uc001pki.1 | 107848055 | 107867441 | 19386 | | | | | |
| uc001pkj.1 | 107848055 | 107874321 | 26266 | | | | | |
| uc001pkk.1 | 107884885 | 107969570 | 84685 | | | | | |
| uc001pkl.1 | 108041025 | 108298180 | 257155 | | | | | |
| uc001pkm.1 | 108041025 | 108316858 uc001pkm.1 | 275833 | DDX10 | 1 | b7 | 12 | NA | NA |

| | | | | | Rank order of peak size | Number of units covered by gene +/-3 | Distance from gene to peak | Gene size in units |

Fig. 9a

| #name | txStart | txEnd | size | fusion gene name | Rank size order | Comparative genomics peak order | standard | gene size |
|---|---|---|---|---|---|---|---|---|
| uc001pkn.1 | 108798084 | 108801533 | 3449 | | | | | |
| uc001pko.1 | 108800067 | 108805048 | 4981 | | | | | |
| uc001pkp.1 | 109281864 | 109283809 | 1945 | | | | | |

Fig. 9b

Chromosome position represented
chr11:107,041,026-109,316,858
Total number of genes: 14

Total units is always 42

| #name | txStart | txEnd | size | fusion gene name | Rank size order | Comparative genomics peak order standard | gene size |
|---|---|---|---|---|---|---|---|
| uc001pjm.1 | 106967286 | 107041900 | 74614 | | | | |
| uc001pjn.1 | 106967286 | 107042715 | 75429 | | | | |
| uc001pjp.1 | 107083310 | 107087997 | 4687 | | | | |
| uc001pjq.1 | 107166926 | 107234890 | 67964 | | | | |
| uc001pjr.1 | 107166927 | 107304229 | 137302 | | | | |
| uc001pjs.1 | 107179943 | 107234890 | 54947 | | | | |
| uc001pjt.1 | 107304486 | 107339418 | 34932 | | | | |
| uc001pju.1 | 107384617 | 107482775 | 98158 | | | | |
| uc001pjv.1 | 107384617 | 107483698 | 99081 | | | | |
| uc001pjw.1 | 107497467 | 107512876 | 15409 | | | | |
| uc001pjx.1 | 107497467 | 107519874 | 22407 | | | | |
| uc001pjy.1 | 107497467 | 107523485 | 26018 | | | | |
| uc001pjz.1 | 107533327 | 107598507 | 65180 | | | | |
| uc001pka.1 | 107547082 | 107565274 | 18192 | | | | |
| uc001pkb.1 | 107598768 | 107745036 | 146268 | | | | |
| uc001pkc.1 | 107599465 | 107605301 | 5836 | | | | |
| uc001pkd.1 | 107663328 | 107666577 | 3249 | | | | |
| uc001pke.1 | 107663328 | 107745036 | 81708 | | | | |
| uc001pkf.1 | 107663536 | 107671931 | 8395 | | | | |
| uc001pkg.1 | 107672910 | 107709905 | 36995 | | | | |
| uc001pkh.1 | 107758936 | 107843468 | 84532 | | | | |
| uc001pki.1 | 107848055 | 107867441 | 19386 | | | | |
| uc001pkj.1 | 107848055 | 107874321 | 26266 | | | | |
| uc001pkk.1 | 107884885 | 107969570 | 84685 | | | | |
| uc001pkl.1 | 108041025 | 108298180 | 257155 | | | | |

| | | | | | Rank order of peak size | Number of units covered by gene +/-3 | Distance from gene to peak | Gene size in units |
|---|---|---|---|---|---|---|---|---|
| | | | | | b7 | 12 | NA | NA |
| uc001pkm.1 | 108041025 | 108316858 | uc001pkm.1 | 275833 | DDX10 | 1 | | |

Fig. 10a

| #name | txStart | txEnd | size | fusion gene name | Rank size order | Comparative genomics peak order | standard | gene size |
|---|---|---|---|---|---|---|---|---|
| uc001pkn.1 | 108798084 | 108801533 | 3449 | | | | | |
| uc001pko.1 | 108800067 | 108805048 | 4981 | | | | | |
| uc001pkp.1 | 109281864 | 109283809 | 1945 | | | | | |

Fig. 10b

Chromosome position represented
chr21:37693867-39955488
Total number of genes 18

| #name | txStart | txEnd | | fusion gene name | Rank size order | Comparative genomics peak order | standard | actual | gene size |
|---|---|---|---|---|---|---|---|---|---|
| uc002ywg.1 | 37661728 | 37767052 | 105324 | | | | | | |
| uc002ywh.1 | 37661728 | 37780786 | 119058 | | | | | | |
| uc002ywi.1 | 37661728 | 37809549 | 147821 | | | | | | |
| uc002ywj.1 | 37713076 | 37809549 | 96473 | | | | | | |
| uc002ywk.1 | 37714470 | 37809549 | 95079 | | | | | | |
| uc002ywl.1 | 37714470 | 37809549 | 95079 | | | | | | |
| uc002ywm.1 | 37714470 | 37809549 | 95079 | | | | | | |
| uc002ywn.1 | 37901635 | 37904535 | 2900 | | | | | | |
| uc002ywo.1 | 37918656 | 38210566 | 291910 | | | | | | |
| uc002ywp.1 | 38348182 | 38415324 | 67142 | | | | | | |
| uc002ywq.1 | 38415436 | 38450475 | 35039 | | | | | | |
| uc002ywr.1 | 38415436 | 38450475 | 35039 | | | | | | |
| uc002yws.1 | 38415436 | 38450475 | 35039 | | | | | | |
| uc002ywt.1 | 38415436 | 38450475 | 35039 | | | | | | |
| uc002ywu.1 | 38500119 | 38502608 | 2489 | | | | | | |
| uc002ywv.1 | 38550533 | 38595616 | 45083 | | | | | | |
| uc002yww.1 | 38550739 | 38595616 | 44877 | | | | | | |
| uc002ywx.1 | 38566298 | 38595616 | 29318 | | | | | | |
| uc002ywy.1 | 38567267 | 38569313 | 2046 | | | | | | |
| uc002ywz.1 | 38661052 | 38955488 | 294436 | ERG | 1 | 3 | 11 | 2 | 5 |
| uc002yxa.1 | 38675670 | 38792267 | 116597 | | | | | | |
| uc002yxb.1 | 38675670 | 38955488 | 279818 | | | | | | |
| uc002yxc.1 | 38693866 | 38955488 | 261622 | | | | | | |
| uc002yxd.1 | 39032818 | 39067271 | 34453 | | | | | | |
| uc002yxe.1 | 39043036 | 39046601 | 3565 | | | | | | |
| uc002yxf.1 | 39099100 | 39118748 | 19648 | | | | | | |
| uc002yxg.1 | 39099718 | 39118748 | 19030 | | | | | | |
| uc002yxh.1 | 39171084 | 39232223 | 61139 | | | | | | |
| uc002yxi.1 | 39469253 | 39477310 | 8057 | | | | | | |

Fig. 11a

| #name | txStart | txEnd | | Rank size order | Comparative genomics peak order | fusion gene name | standard | actual | gene size |
|---|---|---|---|---|---|---|---|---|---|
| uc002yxj.1 | 39469253 | 39477310 | 8057 | | | | | | |
| uc002yxk.1 | 39479273 | 39607426 | 128153 | | | | | | |
| uc002yxl.1 | 39484017 | 39607426 | 123409 | | | | | | |
| uc002yxm.1 | 39590234 | 39607426 | 17192 | | | | | | |
| uc002yxn.1 | 39607756 | 39608756 | 1000 | | | | | | |
| uc002yxo.1 | 39636110 | 39642917 | 6807 | | | | | | |
| uc002yxp.1 | 39636110 | 39642917 | 6807 | | | | | | |
| uc002yxq.1 | 39636110 | 39642917 | 6807 | | | | | | |
| uc002yxr.1 | 39636110 | 39643140 | 7030 | | | | | | |
| uc002yxs.1 | 39674139 | 39691486 | 17347 | | | | | | |
| uc002yxt.1 | 39681566 | 39691486 | 9920 | | | | | | |
| uc002yxu.1 | 39699639 | 39737997 | 38358 | | | | | | |
| uc002yxv.1 | 39699639 | 39739529 | 39890 | | | | | | |
| uc002yxw.1 | 39715354 | 39739601 | 24247 | | | | | | |
| uc002yxx.1 | 39715354 | 39739601 | 24247 | | | | | | |
| uc002yxy.1 | 39715867 | 39732732 | 16865 | | | | | | |
| uc002yxz.1 | 39739666 | 39809303 | 69637 | | | | | | |
| uc002yya.1 | 39745649 | 39809303 | 63654 | | | | | | |
| uc002yyb.1 | 39850238 | 39956685 | 106447 | | | | | | |
| uc002yyc.1 | 39890944 | 39906238 | 15294 | | | | | | |
| uc002yyd.1 | 39899403 | 39906238 | 6835 | | | | | | |
| uc002yye.1 | 39906841 | 39953709 | 46868 | | | | | | |
| uc002yyf.1 | 39906841 | 39953709 | 46868 | | | | | | |
| uc002yyg.1 | 39924087 | 39953709 | 29622 | | | | | | |
| uc002yyh.1 | 39936181 | 39953709 | 17528 | | | | | | |
| uc002yyi.1 | 39951123 | 39956685 | 5562 | | | | | | |
| uc002yyj.1 | 39951123 | 39956685 | 5562 | | | | | | |
| uc002yyk.1 | 39951123 | 39956685 | 5562 | | | | | | |
| uc002yyl.1 | 39951123 | 39956685 | 5562 | | | | | | |
| uc002yym.1 | 39951123 | 39956685 | 5562 | | | | | | |

Fig. 11b

Chromosome position represented
chr12:10,913,625-13,159,528
Total number of genes: 32

| #name | txStart | txEnd | size | fusion gene name | Rank size order | Comparative genomics peak order | standard | actual | gene size |
|---|---|---|---|---|---|---|---|---|---|
| uc001qzb.1 | 10889748 | 11215465 | 325717 | | | | | | |
| uc001qzc.1 | 10924826 | 10928141 | 3315 | | | | | | |
| uc001qzd.1 | 10924826 | 10928156 | 3330 | | | | | | |
| uc001qze.1 | 10924826 | 11215465 | 290639 | | | | | | |
| uc001qzf.1 | 10924826 | 11354633 | 429807 | | | | | | |
| uc001qzg.1 | 10951791 | 10953428 | 1637 | | | | | | |
| uc001qzh.1 | 10973100 | 10977661 | 4561 | | | | | | |
| uc001qzi.1 | 10973100 | 10977665 | 4565 | | | | | | |
| uc001qzj.1 | 10981273 | 11215465 | 234192 | | | | | | |
| uc001qzk.1 | 10982119 | 10983073 | 954 | | | | | | |
| uc001qzl.1 | 11029826 | 11030726 | 900 | | | | | | |
| uc001qzm.1 | 11040811 | 11041741 | 930 | | | | | | |
| uc001qzn.1 | 11065537 | 11066437 | 900 | | | | | | |
| uc001qzo.1 | 11074252 | 11075273 | 1021 | | | | | | |
| uc001qzp.1 | 11105230 | 11106160 | 930 | | | | | | |
| uc001qzq.1 | 11135152 | 11136179 | 1027 | | | | | | |
| uc001qzr.1 | 11229865 | 11230810 | 945 | | | | | | |
| uc001qzs.1 | 11310123 | 11313908 | 3785 | | | | | | |
| uc001qzt.1 | 11351281 | 11354633 | 3352 | | | | | | |
| uc001qzu.1 | 11396023 | 11399791 | 3768 | | | | | | |
| uc001qzv.1 | 11396023 | 11399791 | 3768 | | | | | | |
| uc001qzw.1 | 11396023 | 11399791 | 3768 | | | | | | |
| uc001qzx.1 | 11435740 | 11439768 | 4028 | | | | | | |
| uc001qzy.1 | 11592230 | 11608602 | 16372 | | | | | | |
| uc001qzz.1 | 11694054 | 11939592 | 245538 | | | | | | |
| uc001raa.1 | 11913624 | 12159528 | 245904 | uc001raa.1 ETV6 | 3 | 1 | 14 | 0 | 8 |
| uc001rab.1 | 12094064 | 12099970 | 5906 | | | | | | |
| uc001rac.1 | 12115144 | 12143894 | 28750 | | | | | | |
| uc001rad.1 | 12115668 | 12143894 | 28226 | | | | | | |

Fig. 12a

| #name | txStart | txEnd | size | fusion gene name | Rank size order | Comparative genomics peak order | standard | actual | gene size |
|---|---|---|---|---|---|---|---|---|---|
| uc001rae.1 | 12115668 | 12143894 | 28226 | | | | | | |
| uc001raf.1 | 12123499 | 12255214 | 131715 | | | | | | |
| uc001rag.1 | 12160229 | 12288856 | 128627 | | | | | | |
| uc001rah.1 | 12164955 | 12311013 | 146058 | | | | | | |
| uc001rai.1 | 12373484 | 12394436 | 20952 | | | | | | |
| uc001raj.1 | 12373484 | 12394436 | 20952 | | | | | | |
| uc001rak.1 | 12399833 | 12401268 | 1435 | | | | | | |
| uc001ral.1 | 12401321 | 12511105 | 109784 | | | | | | |
| uc001ram.1 | 12518423 | 12520998 | 2575 | | | | | | |
| uc001ran.1 | 12520097 | 12565664 | 45567 | | | | | | |
| uc001rao.1 | 12520097 | 12606584 | 86487 | | | | | | |
| uc001rap.1 | 12656097 | 12689308 | 33211 | | | | | | |
| uc001raq.1 | 12705262 | 12706671 | 1409 | | | | | | |
| uc001rar.1 | 12705262 | 12728722 | 23460 | | | | | | |
| uc001ras.1 | 12731468 | 12740388 | 8920 | | | | | | |
| uc001rat.1 | 12761575 | 12766570 | 4995 | | | | | | |
| uc001rau.1 | 12770129 | 12835664 | 65535 | | | | | | |
| uc001rav.1 | 12770129 | 12874182 | 104053 | | | | | | |
| uc001raw.1 | 12829881 | 12835664 | 5783 | | | | | | |
| uc001rax.1 | 12857407 | 12874182 | 16775 | | | | | | |
| uc001ray.1 | 12857407 | 12874182 | 16775 | | | | | | |
| uc001raz.1 | 12935222 | 12954077 | 18855 | | | | | | |
| uc001rba.1 | 12935222 | 12957867 | 22645 | | | | | | |
| uc001rbb.1 | 12959717 | 12962138 | 2421 | | | | | | |
| uc001rbc.1 | 12984975 | 12994585 | 9610 | | | | | | |
| uc001rbd.1 | 13019065 | 13044488 | 25423 | | | | | | |
| uc001rbe.1 | 13024037 | 13028843 | 4806 | | | | | | |
| uc001rbf.1 | 13029845 | 13044488 | 14643 | | | | | | |
| uc001rbg.1 | 13044647 | 13047556 | 2909 | | | | | | |
| uc001rbh.1 | 13052295 | 13083871 | 31576 | | | | | | |
| uc001rbi.1 | 13088581 | 13127650 | 39069 | | | | | | |
| uc001rbj.1 | 13128308 | 13139976 | 11668 | | | | | | |
| uc001rbk.1 | 13128308 | 13139976 | 11668 | | | | | | |

Fig. 12b

| #name | txStart | txEnd | size | fusion gene name | Rank size order | Comparative genomics peak order | standard | actual | gene size |
|---|---|---|---|---|---|---|---|---|---|
| uc001rbl.1 | 13128308 | 13139976 | 11668 | | | | | | |
| uc001rbm.1 | 13128308 | 13139976 | 11668 | | | | | | |
| uc001rbn.1 | 13128308 | 13147886 | 19578 | | | | | | |
| uc001rbo.1 | 13128308 | 13147886 | 19578 | | | | | | |
| uc001rbp.1 | 13128308 | 13147886 | 19578 | | | | | | |
| uc001rbq.1 | 13129027 | 13147886 | 18859 | | | | | | |

Fig. 12c

Chromosome position represented
chr22:26,994,017-29,026,515
Total number of genes  25

| #name | txStart | txEnd | size | fusion gene name | Rank size order | Comparative genomics peak order | standard | actual | gene size |
|---|---|---|---|---|---|---|---|---|---|
| uc003adr.1 | 27413730 | 27460715 | 46985 | | | | | | |
| uc003ads.1 | 27413730 | 27460715 | 46985 | | | | | | |
| uc003adt.1 | 27413730 | 27467822 | 54092 | | | | | | |
| uc003adu.1 | 27413730 | 27467822 | 54092 | | | | | | |
| uc003adv.1 | 27413730 | 27467822 | 54092 | | | | | | |
| uc003adw.1 | 27413730 | 27467822 | 54092 | | | | | | |
| uc003adx.1 | 27413730 | 27467822 | 54092 | | | | | | |
| uc003ady.1 | 27413730 | 27467822 | 54092 | | | | | | |
| uc003adz.1 | 27413730 | 27467822 | 54092 | | | | | | |
| uc003aea.1 | 27468042 | 27483496 | 15454 | | | | | | |
| uc003aeb.1 | 27498706 | 27515278 | 16572 | | | | | | |
| uc003aec.1 | 27520547 | 27523033 | 2486 | | | | | | |
| uc003aed.1 | 27520547 | 27526121 | 5574 | | | | | | |
| uc003aee.1 | 27520547 | 27526560 | 6013 | | | | | | |
| uc003aef.1 | 27520547 | 27526560 | 6013 | | | | | | |
| uc003aeg.1 | 27609889 | 27779821 | 169932 | | | | | | |
| uc003aeh.1 | 27713039 | 27776936 | 63897 | | | | | | |
| uc003aei.1 | 27779911 | 27783476 | 3565 | | | | | | |
| uc003aej.1 | 27784659 | 27787907 | 3248 | | | | | | |
| uc003aek.1 | 27799105 | 27872808 | 73703 | | | | | | |
| uc003ael.1 | 27799105 | 27872808 | 73703 | | | | | | |
| uc003aem.1 | 27931952 | 27985586 | 53634 | | | | | | |
| uc003aen.1 | 27931952 | 27985586 | 53634 | | | | | | |
| uc003aeo.1 | 27931952 | 27985586 | 53634 | | | | | | |
| uc003aep.1 | 27931952 | 27985586 | 53634 | | | | | | |
| uc003aeq.1 | 27985843 | 27993914 | 8071 | | | | | | |
| uc003aer.1 | 27985843 | 27993914 | 8071 | | | | | | |
| uc003aes.1 | 27994016 | 28016672 | 22656 | | | | | | |
| uc003aet.1 | 27994016 | 28026515 uc003aet.1 | 32499 | EWSR1 | b5 | 1 | 7 | 0 | 1 |

Fig. 13a

| #name | txStart | txEnd | size | fusion gene name | Rank size order | Comparative genomics peak order | standard | actual | gene size |
|---|---|---|---|---|---|---|---|---|---|
| uc003aeu.1 | 27994016 | 280026515 | 32499 | | | | | | |
| uc003aev.1 | 27994016 | 280026515 | 32499 | | | | | | |
| uc003aew.1 | 27994016 | 280026515 | 32499 | | | | | | |
| uc003aex.1 | 27994016 | 280026515 | 32499 | | | | | | |
| uc003aey.1 | 28004018 | 280026515 | 22497 | | | | | | |
| uc003aez.1 | 28015501 | 280026515 | 11014 | | | | | | |
| uc003afa.1 | 28032996 | 280038774 | 5778 | | | | | | |
| uc003afb.1 | 28032996 | 280038774 | 5778 | | | | | | |
| uc003afc.1 | 28032996 | 280038774 | 5778 | | | | | | |
| uc003afd.1 | 28032996 | 280038774 | 5778 | | | | | | |
| uc003afe.1 | 28033047 | 280038774 | 5727 | | | | | | |
| uc003aff.1 | 28038921 | 280041748 | 2827 | | | | | | |
| uc003afg.1 | 28038921 | 280041748 | 2827 | | | | | | |
| uc003afh.1 | 28053668 | 280058310 | 4642 | | | | | | |
| uc003afi.1 | 28053668 | 28093259 | 39591 | | | | | | |
| uc003afj.1 | 28053668 | 28114569 | 60901 | | | | | | |
| uc003afk.1 | 28053668 | 28114569 | 60901 | | | | | | |
| uc003afl.1 | 28053668 | 28114569 | 60901 | | | | | | |
| uc003afm.1 | 28163005 | 28168118 | 5113 | | | | | | |
| uc003afn.1 | 28164571 | 28168444 | 3873 | | | | | | |
| uc003afo.1 | 28206218 | 28217277 | 11059 | | | | | | |
| uc003afp.1 | 28215264 | 28217277 | 2013 | | | | | | |
| uc003afq.1 | 28234155 | 28254455 | 20300 | | | | | | |
| uc003afr.1 | 28234155 | 28279644 | 45489 | | | | | | |
| uc003afs.1 | 28234155 | 28279644 | 45489 | | | | | | |
| uc003aft.1 | 28234155 | 28279736 | 45581 | | | | | | |
| uc003afu.1 | 28234155 | 28279736 | 45581 | | | | | | |
| uc003afv.1 | 28255150 | 28279736 | 24586 | | | | | | |
| uc003afw.1 | 28262612 | 28269531 | 6919 | | | | | | |
| uc003afx.1 | 28280799 | 28307326 | 26527 | | | | | | |
| uc003afy.1 | 28329564 | 28409904 | 80340 | | | | | | |
| uc003afz.1 | 28329564 | 28409904 | 80340 | | | | | | |
| uc003aga.1 | 28329564 | 28424585 | 95021 | | | | | | |

Fig. 13b

| #name | txStart | txEnd | size | fusion gene name | Rank size order | Comparative genomics peak order | standard | actual | gene size |
|---|---|---|---|---|---|---|---|---|---|
| uc003agb.1 | 28329564 | 28424585 | 95021 | | | | | | |
| uc003agc.1 | 28329564 | 28424585 | 95021 | | | | | | |
| uc003agd.1 | 28329564 | 28424585 | 95021 | | | | | | |
| uc003age.1 | 28329564 | 28424585 | 95021 | | | | | | |
| uc003agf.1 | 28329564 | 28424585 | 95021 | | | | | | |
| uc003agg.1 | 28329564 | 28424585 | 95021 | | | | | | |
| uc003agh.1 | 28329564 | 28424585 | 95021 | | | | | | |
| uc003agi.1 | 28329564 | 28424585 | 95021 | | | | | | |
| uc003agj.1 | 28329564 | 28424585 | 95021 | | | | | | |
| uc003agk.1 | 28362732 | 28424585 | 61853 | | | | | | |
| uc003agl.1 | 28446343 | 28457820 | 11477 | | | | | | |
| uc003agm.1 | 28456944 | 28492969 | 36025 | | | | | | |
| uc003agn.1 | 28456944 | 28492969 | 36025 | | | | | | |
| uc003ago.1 | 28472155 | 28493000 | 20845 | | | | | | |
| uc003agp.1 | 28493357 | 28496402 | 3045 | | | | | | |
| uc003agq.1 | 28493357 | 28496402 | 3045 | | | | | | |
| uc003agr.1 | 28514600 | 28564254 | 49654 | | | | | | |
| uc003ags.1 | 28514600 | 28564254 | 49654 | | | | | | |
| uc003agt.1 | 28514600 | 28564254 | 49654 | | | | | | |
| uc003agu.1 | 28609198 | 28753869 | 144671 | | | | | | |
| uc003agv.1 | 28609198 | 28753869 | 144671 | | | | | | |
| uc003agw.1 | 28609198 | 28753869 | 144671 | | | | | | |
| uc003agx.1 | 28754222 | 28756494 | 2272 | | | | | | |
| uc003agy.1 | 28806452 | 28903062 | 96610 | | | | | | |
| uc003agz.1 | 28966442 | 28972748 | 6306 | | | | | | |
| uc003aha.1 | 28972198 | 28972982 | 784 | | | | | | |
| uc003ahb.1 | 28988818 | 28992840 | 4022 | | | | | | |
| uc003ahc.1 | 29011106 | 29015502 | 4396 | | | | | | |
| uc003ahd.1 | 29011106 | 29015502 | 4396 | | | | | | |
| uc003ahe.1 | 29011106 | 29015502 | 4396 | | | | | | |
| uc003ahf.1 | 29011106 | 29021832 | 10726 | | | | | | |
| uc003ahg.1 | 29011106 | 29025540 | 14434 | | | | | | |
| uc003ahh.1 | 29011106 | 29025540 | 14434 | | | | | | |

Fig. 13c

| #name | txStart | txEnd | size | fusion gene name | Rank size order | Comparative genomics peak order | standard | actual | gene size |
|---|---|---|---|---|---|---|---|---|---|
| uc003ahi.1 | 29011106 | 29025540 | 14434 | | | | | | |
| uc003ahj.1 | 29017978 | 29033879 | 15901 | | | | | | |
| uc003ahk.1 | 29017978 | 29052894 | 34916 | | | | | | |

Fig. 13d

Chromosome position represented
chr6:107,987,719-110,108,649
Total number of genes 24

| #name | txStart | txEnd | size | fusion gene name | Rank size order | Comparative genomics peak order | standard | actual | gene size |
|---|---|---|---|---|---|---|---|---|---|
| uc003prw.1 | 107918009 | 108016833 | 98824 | | | | | | |
| uc003prx.1 | 107918009 | 108089206 | 171197 | | | | | | |
| uc003pry.1 | 108132105 | 108160292 | 28187 | | | | | | |
| uc003prz.1 | 108132105 | 108252214 | 120109 | | | | | | |
| uc003psa.1 | 108146341 | 108200148 | 53807 | | | | | | |
| uc003psb.1 | 108298214 | 108349806 | 51592 | | | | | | |
| uc003psc.1 | 108298214 | 108386086 | 87872 | | | | | | |
| uc003psd.1 | 108469305 | 108502634 | 33329 | | | | | | |
| uc003pse.1 | 108469368 | 108472132 | 2764 | | | | | | |
| uc003psf.1 | 108551532 | 108585915 | 34383 | | | | | | |
| uc003psg.1 | 108593954 | 108616706 | 22752 | | | | | | |
| uc003psh.1 | 108639409 | 108689156 | 49747 | | | | | | |
| uc003psi.1 | 108639409 | 108689156 | 49747 | | | | | | |
| uc003psj.1 | 108722790 | 108950944 | 228154 | | | | | | |
| uc003psk.1 | 108987718 | 109108649 | 120931 | | | | | | |
| uc003psl.1 | 108987718 | 109108649 uc003psl.1 | 120931 | FKHRL1 | 4 | 7 | 9 | 0 | 3 |
| uc003psm.1 | 108988761 | 109108649 | 119888 | | | | | | |
| uc003psn.1 | 109109179 | 109111584 | 2405 | | | | | | |
| uc003pso.1 | 109179549 | 109197466 | 17917 | | | | | | |
| uc003psp.1 | 109179549 | 109197838 | 18289 | | | | | | |
| uc003psq.1 | 109187056 | 109197014 | 9958 | | | | | | |
| uc003psr.1 | 109187056 | 109197466 | 10410 | | | | | | |
| uc003pss.1 | 109276317 | 109401877 | 125560 | | | | | | |
| uc003pst.1 | 109414337 | 109437444 | 23107 | | | | | | |
| uc003psu.1 | 109414337 | 109521970 | 107633 | | | | | | |
| uc003psv.1 | 109523415 | 109586384 | 62969 | | | | | | |
| uc003psw.1 | 109523415 | 109586384 | 62969 | | | | | | |
| uc003psx.1 | 109523415 | 109591796 | 68381 | | | | | | |
| uc003psy.1 | 109557199 | 109591796 | 34597 | | | | | | |

Fig. 14a

| #name | txStart | txEnd | size | fusion gene name | Rank size order | Comparative genomics peak order | standard | actual | gene size |
|---|---|---|---|---|---|---|---|---|---|
| uc003psz.1 | 109573114 | 109591796 | 18682 | | | | | | |
| uc003pta.1 | 109664509 | 109698413 | 33904 | | | | | | |
| uc003ptb.1 | 109722198 | 109736116 | 13918 | | | | | | |
| uc003ptc.1 | 109766370 | 109782844 | 16474 | | | | | | |
| uc003ptd.1 | 109794409 | 109810340 | 15931 | | | | | | |
| uc003pte.1 | 109794413 | 109810340 | 15927 | | | | | | |
| uc003ptf.1 | 109794413 | 109810340 | 15927 | | | | | | |
| uc003ptg.1 | 109820624 | 109868522 | 47898 | | | | | | |
| uc003pth.1 | 109866852 | 109868683 | 1831 | | | | | | |
| uc003pti.1 | 109868623 | 109871815 | 3192 | | | | | | |
| uc003ptj.1 | 109871958 | 109882346 | 10388 | | | | | | |
| uc003ptk.1 | 109871958 | 109883883 | 11925 | | | | | | |
| uc003ptl.1 | 109890411 | 109911133 | 20722 | | | | | | |
| uc003ptm.1 | 109908844 | 109911133 | 2289 | | | | | | |
| uc003ptn.1 | 109920756 | 109934386 | 13630 | | | | | | |
| uc003pto.1 | 109955523 | 109974023 | 18500 | | | | | | |
| uc003ptp.1 | 109955524 | 109978433 | 22909 | | | | | | |
| uc003ptq.1 | 109977579 | 110047097 | 69518 | | | | | | |
| uc003ptr.1 | 110059591 | 110119113 | 59522 | | | | | | |
| uc003pts.1 | 110072509 | 110119062 | 46553 | | | | | | |

Fig. 14b

Chromosome position represented
chr13:26,773,790-28,967,232
Total number of genes 15

| #name | txStart | txEnd | size | fusion gene name | Rank size order | Comparative genomics peak order | standard | actual | gene size |
|---|---|---|---|---|---|---|---|---|---|
| uc001ure.1 | 26896751 | 26907826 | 11075 | | | | | | |
| uc001urf.1 | 26896751 | 26907826 | 11075 | | | | | | |
| uc001urg.1 | 26897547 | 26907826 | 10279 | | | | | | |
| uc001urh.1 | 26907780 | 26913809 | 6029 | | | | | | |
| uc001uri.1 | 26907780 | 26922325 | 14545 | | | | | | |
| uc001urj.1 | 26907780 | 26922711 | 14931 | | | | | | |
| uc001urk.1 | 26907780 | 26922711 | 14931 | | | | | | |
| uc001url.1 | 27018049 | 27092539 | 74490 | | | | | | |
| uc001urm.1 | 27025344 | 27093244 | 67900 | | | | | | |
| uc001urn.1 | 27092894 | 27095585 | 2691 | | | | | | |
| uc001uro.1 | 27093899 | 27095585 | 1686 | | | | | | |
| uc001urp.1 | 27093899 | 27139548 | 45649 | | | | | | |
| uc001urq.1 | 27093899 | 27139548 | 45649 | | | | | | |
| uc001urr.1 | 27264779 | 27266089 | 1310 | | | | | | |
| uc001urs.1 | 27301905 | 27393541 | 91636 | | | | | | |
| uc001urt.1 | 27392156 | 27397394 | 5238 | | | | | | |
| uc001uru.1 | 27417342 | 27417710 | 368 | | | | | | |
| uc001urv.1 | 27434277 | 27441317 | 7040 | | | | | | |
| uc001urw.1 | 27475410 | 27572729 | 97319 | | | | | | |
| uc001urx.1 | 27646416 | 27767471 | 121055 | | | | | | |
| uc001ury.1 | 27646416 | 27767471 | 121055 | | | | | | |
| uc001urz.1 | 27646416 | 27767471 | 121055 | | | | | | |
| uc001usa.1 | 27773789 | 27818426 | 44637 | | | | | | |
| uc001usb.1 | 27773789 | 27967232 | 193443 uc001usb.1 | FLT1 | 2 | 4 | 10 | 0 | 4 |
| uc001usc.1 | 27861818 | 27967232 | 105414 | | | | | | |
| uc001usd.1 | 27938587 | 27967232 | 28645 | | | | | | |
| uc001use.1 | 27965434 | 27967254 | 1820 | | | | | | |
| uc001usf.1 | 28131250 | 28151059 | 19809 | | | | | | |
| uc001usg.1 | 28172217 | 28187110 | 14893 | | | | | | |

Fig. 15a

| #name | txStart | txEnd | size | fusion gene name | Rank size order | Comparative genomics peak order | standard | actual | gene size |
|---|---|---|---|---|---|---|---|---|---|
| uc001ush.1 | 28172217 | 28190962 | 18745 | | | | | | |
| uc001usi.1 | 28172217 | 28191105 | 18888 | | | | | | |
| uc001usj.1 | 28172220 | 28190962 | 18742 | | | | | | |
| uc001usk.1 | 28181090 | 28187675 | 6585 | | | | | | |
| uc001usl.1 | 28496747 | 28975879 | 479132 | | | | | | |
| uc001usm.1 | 28900776 | 28975879 | 75103 | | | | | | |
| uc001usn.1 | 28948651 | 28959887 | 11236 | | | | | | |

Fig. 15b

Chromosome position represented
chr16:30,098,954-32,110,600
Total number of genes 55

| #name | txStart | txEnd | size | fusion gene name | Rank size order | Comparative genomics peak order | standard | actual | gene size |
|---|---|---|---|---|---|---|---|---|---|
| uc002dtk.1 | 29463832 | 30113128 | 649296 | | | | | | |
| uc002dww.1 | 30102426 | 30107898 | 5472 | | | | | | |
| uc002dwx.1 | 30102426 | 30107898 | 5472 | | | | | | |
| uc002dwy.1 | 30105503 | 30107897 | 2394 | | | | | | |
| uc002dwz.1 | 30107505 | 30108076 | 571 | | | | | | |
| uc002dxa.1 | 30111756 | 30113128 | 1372 | | | | | | |
| uc002dxb.1 | 30111756 | 30113128 | 1372 | | | | | | |
| uc002dxc.1 | 30112708 | 30116383 | 3675 | | | | | | |
| uc002dxd.1 | 30112708 | 30123151 | 10443 | | | | | | |
| uc002dxe.1 | 30112713 | 30123151 | 10438 | | | | | | |
| uc002dxf.1 | 30112713 | 30123151 | 10438 | | | | | | |
| uc002dxg.1 | 30112717 | 30116383 | 3666 | | | | | | |
| uc002dxh.1 | 30112717 | 30116383 | 3666 | | | | | | |
| uc002dxi.1 | 30113707 | 30123151 | 9444 | | | | | | |
| uc002dxj.1 | 30114611 | 30123151 | 8540 | | | | | | |
| uc002dxk.1 | 30118036 | 30123151 | 5115 | | | | | | |
| uc002dxl.1 | 30123137 | 30125749 | 2612 | | | | | | |
| uc002dxm.1 | 30141791 | 30143314 | 1523 | | | | | | |
| uc002dxn.1 | 30141850 | 30164433 | 22583 | | | | | | |
| uc002dxo.1 | 30183408 | 30189699 | 6291 | | | | | | |
| uc002dxp.1 | 30186414 | 30254196 | 67782 | | | | | | |
| uc002dxq.1 | 30203890 | 30206481 | 2591 | | | | | | |
| uc002dxr.1 | 30271668 | 30273756 | 2088 | | | | | | |
| uc002dxs.1 | 30271668 | 30274128 | 2460 | | | | | | |
| uc002dxt.1 | 30275923 | 30278496 | 2573 | | | | | | |
| uc002dxu.1 | 30275923 | 30288402 | 12479 | | | | | | |
| uc002dxv.1 | 30293623 | 30296811 | 3188 | | | | | | |
| uc002dxw.1 | 30296956 | 30297563 | 607 | | | | | | |
| uc002dxx.1 | 30296956 | 30301420 | 4464 | | | | | | |

Fig. 16a

| #name | txStart | txEnd | size | fusion gene name | Rank size order | Comparative genomics peak order | standard | actual | gene size |
|---|---|---|---|---|---|---|---|---|---|
| uc002dxy.1 | 30296956 | 30301672 | 4716 | | | | | | |
| uc002dxz.1 | 30314277 | 30318216 | 3939 | | | | | | |
| uc002dya.1 | 30314557 | 30318216 | 3659 | | | | | | |
| uc002dyb.1 | 30316929 | 30318930 | 2001 | | | | | | |
| uc002dyc.1 | 30326436 | 30333431 | 6995 | | | | | | |
| uc002dyd.1 | 30326436 | 30338231 | 11795 | | | | | | |
| uc002dye.1 | 30326866 | 30338231 | 11365 | | | | | | |
| uc002dyf.1 | 30342519 | 30348874 | 6355 | | | | | | |
| uc002dyg.1 | 30362452 | 30364725 | 2273 | | | | | | |
| uc002dyh.1 | 30362453 | 30364725 | 2272 | | | | | | |
| uc002dyi.1 | 30391571 | 30442007 | 50436 | | | | | | |
| uc002dyj.1 | 30391571 | 30442007 | 50436 | | | | | | |
| uc002dyk.1 | 30442826 | 30445411 | 2585 | | | | | | |
| uc002dyl.1 | 30445739 | 30449478 | 3739 | | | | | | |
| uc002dym.1 | 30450215 | 30451828 | 1613 | | | | | | |
| uc002dyn.1 | 30450279 | 30453695 | 3416 | | | | | | |
| uc002dyo.1 | 30450286 | 30453695 | 3409 | | | | | | |
| uc002dyp.1 | 30453894 | 30455966 | 2072 | | | | | | |
| uc002dyq.1 | 30472585 | 30477085 | 4500 | | | | | | |
| uc002dyr.1 | 30473007 | 30477085 | 4078 | | | | | | |
| uc002dys.1 | 30488523 | 30491229 | 2706 | | | | | | |
| uc002dyt.1 | 30488523 | 30491229 | 2706 | | | | | | |
| uc002dyu.1 | 30491076 | 30502669 | 11593 | | | | | | |
| uc002dyv.1 | 30497794 | 30504511 | 6717 | | | | | | |
| uc002dyw.1 | 30499494 | 30504511 | 5017 | | | | | | |
| uc002dyx.1 | 30522200 | 30529183 | 6983 | | | | | | |
| uc002dyy.1 | 30569741 | 30575235 | 5494 | | | | | | |
| uc002dyz.1 | 30569741 | 30575235 | 5494 | | | | | | |
| uc002dza.1 | 30570204 | 30575235 | 5031 | | | | | | |
| uc002dzb.1 | 30572930 | 30574036 | 1106 | | | | | | |
| uc002dzc.1 | 30578743 | 30589629 | 10886 | | | | | | |
| uc002dzd.1 | 30584127 | 30589629 | 5502 | | | | | | |
| uc002dze.1 | 30617962 | 30659529 | 41567 | | | | | | |

Fig. 16b

| #name | txStart | txEnd | size | fusion gene name | Rank size order | Comparative genomics peak order | standard | actual | gene size |
|---|---|---|---|---|---|---|---|---|---|
| uc002dzf.1 | 30622885 | 30663102 | 40217 | | | | | | |
| uc002dzg.1 | 30626004 | 30659529 | 33525 | | | | | | |
| uc002dzh.1 | 30629358 | 30629487 | 129 | | | | | | |
| uc002dzi.1 | 30667237 | 30675998 | 8761 | | | | | | |
| uc002dzj.1 | 30667237 | 30675998 | 8761 | | | | | | |
| uc002dzk.1 | 30667237 | 30676183 | 8946 | | | | | | |
| uc002dzl.1 | 30667624 | 30670735 | 3111 | | | | | | |
| uc002dzm.1 | 30676252 | 30680901 | 4649 | | | | | | |
| uc002dzn.1 | 30676252 | 30680901 | 4649 | | | | | | |
| uc002dzo.1 | 30676252 | 30681043 | 4791 | | | | | | |
| uc002dzp.1 | 30678858 | 30680901 | 2043 | | | | | | |
| uc002dzq.1 | 30681130 | 30694039 | 12909 | | | | | | |
| uc002dzr.1 | 30681143 | 30694039 | 12896 | | | | | | |
| uc002dzs.1 | 30697270 | 30706024 | 8754 | | | | | | |
| uc002dzt.1 | 30752873 | 30812900 | 60027 | | | | | | |
| uc002dzu.1 | 30794733 | 30814040 | 19307 | | | | | | |
| uc002dzv.1 | 30806616 | 30812900 | 6284 | | | | | | |
| uc002dzw.1 | 30815428 | 30822382 | 6954 | | | | | | |
| uc002dzx.1 | 30815428 | 30822382 | 6954 | | | | | | |
| uc002dzy.1 | 30838730 | 30842091 | 3361 | | | | | | |
| uc002dzz.1 | 30841892 | 30867605 | 25713 | | | | | | |
| uc002eaa.1 | 30844590 | 30867605 | 23015 | | | | | | |
| uc002eab.1 | 30846129 | 30867605 | 21476 | | | | | | |
| uc002eac.1 | 30867915 | 30873760 | 5845 | | | | | | |
| uc002ead.1 | 30876115 | 30903482 | 27367 | | | | | | |
| uc002eae.1 | 30876586 | 30883145 | 6559 | | | | | | |
| uc002eaf.1 | 30904032 | 30907972 | 3940 | | | | | | |
| uc002eag.1 | 30904032 | 30907972 | 3940 | | | | | | |
| uc002eah.1 | 30904281 | 30907972 | 3691 | | | | | | |
| uc002eai.1 | 30910868 | 30929276 | 18408 | | | | | | |
| uc002eaj.1 | 30911903 | 30929276 | 17373 | | | | | | |
| uc002eak.1 | 30951916 | 30958986 | 7070 | | | | | | |
| uc002eal.1 | 30952403 | 30958986 | 6583 | | | | | | |

Fig. 16c

| #name | txStart | txEnd | size | fusion gene name | Rank size order | Comparative genomics peak order | standard | actual | gene size |
|---|---|---|---|---|---|---|---|---|---|
| uc002eam.1 | 30952403 | 30958986 | 6583 | | | | | | |
| uc002ean.1 | 30960532 | 30961777 | 1245 | | | | | | |
| uc002eao.1 | 30979671 | 30993005 | 13334 | | | | | | |
| uc002eap.1 | 30993268 | 31002334 | 9066 | | | | | | |
| uc002eaq.1 | 31002245 | 31007631 | 5386 | | | | | | |
| uc002ear.1 | 31002245 | 31013777 | 11532 | | | | | | |
| uc002eas.1 | 31009675 | 31013777 | 4102 | | | | | | |
| uc002eat.1 | 31009675 | 31013777 | 4102 | | | | | | |
| uc002eau.1 | 31009675 | 31013777 | 4102 | | | | | | |
| uc002eav.1 | 31027248 | 31031378 | 4130 | | | | | | |
| uc002eaw.1 | 31027248 | 31031422 | 4174 | | | | | | |
| uc002eax.1 | 31036487 | 31050181 | 13694 | | | | | | |
| uc002eay.1 | 31036487 | 31050206 | 13719 | | | | | | |
| uc002eaz.1 | 31044455 | 31050206 | 5751 | | | | | | |
| uc002eba.1 | 31046010 | 31050213 | 4203 | | | | | | |
| uc002ebb.1 | 31048831 | 31050206 | 1375 | | | | | | |
| uc002ebc.1 | 31050256 | 31054652 | 4396 | | | | | | |
| uc002ebd.1 | 31057749 | 31068888 | 11139 | | | | | | |
| uc002ebe.1 | 31098953 | 31104001 | 5048 | | | | | | |
| uc002ebf.1 | 31098953 | 31110600 | 11647 | FUS | b5 | 2 | 6 | 0 | 1 |
| uc002ebf.1 uc002ebf.1 | 31098953 | 31110600 | 11647 | | | | | | |
| uc002ebg.1 | 31098953 | 31110600 | 11647 | | | | | | |
| uc002ebh.1 | 31098953 | 31110600 | 11647 | | | | | | |
| uc002ebi.1 | 31098953 | 31110600 | 11647 | | | | | | |
| uc002ebj.1 | 31105579 | 31105658 | 79 | | | | | | |
| uc002ebk.1 | 31120307 | 31121752 | 1445 | | | | | | |
| uc002ebl.1 | 31120307 | 31121752 | 1445 | | | | | | |
| uc002ebm.1 | 31132915 | 31144011 | 11096 | | | | | | |
| uc002ebn.1 | 31134783 | 31135896 | 1113 | | | | | | |
| uc002ebo.1 | 31144693 | 31145331 | 638 | | | | | | |
| uc002ebp.1 | 31178788 | 31251714 | 72926 | | | | | | |
| uc002ebq.1 | 31178788 | 31251714 | 72926 | | | | | | |
| uc002ebr.1 | 31240062 | 31246245 | 6183 | | | | | | |

Fig. 16d

| #name | txStart | txEnd | size | fusion gene name | Rank size order | Comparative genomics peak order | standard | actual | gene size |
|---|---|---|---|---|---|---|---|---|---|
| uc002ebt.1 | 31274009 | 31301765 | 27756 | | | | | | |
| uc002ebu.1 | 31274009 | 31301819 | 27810 | | | | | | |
| uc002ebv.1 | 31312133 | 31345327 | 33194 | | | | | | |
| uc002ebw.1 | 31316417 | 31328139 | 11722 | | | | | | |
| uc002ebx.1 | 31346555 | 31347222 | 667 | | | | | | |
| uc002eby.1 | 31354259 | 31361847 | 7588 | | | | | | |
| uc002ebz.1 | 31354259 | 31361982 | 7723 | | | | | | |
| uc002eca.1 | 31377817 | 31385988 | 8171 | | | | | | |
| uc002ecb.1 | 31377817 | 31385988 | 8171 | | | | | | |
| uc002ecc.1 | 31377817 | 31385989 | 8172 | | | | | | |
| uc002ecd.1 | 31390984 | 31396781 | 5797 | | | | | | |
| uc002ece.1 | 31392026 | 31396781 | 4755 | | | | | | |
| uc002ecf.1 | 31401939 | 31409590 | 7651 | | | | | | |
| uc002ecg.1 | 31406017 | 31408565 | 2548 | | | | | | |
| uc002ech.1 | 31408315 | 31412560 | 4245 | | | | | | |
| uc002eci.1 | 31408315 | 31427207 | 18892 | | | | | | |
| uc002ecj.1 | 31446703 | 31447625 | 922 | | | | | | |
| uc002eck.1 | 31619416 | 31626246 | 6830 | | | | | | |
| uc002ecl.1 | 31619416 | 31626246 | 6830 | | | | | | |
| uc002ecm.1 | 31619416 | 31626246 | 6830 | | | | | | |
| uc002ecn.1 | 31632054 | 31680387 | 48333 | | | | | | |
| uc002eco.1 | 31632054 | 31713691 | 81637 | | | | | | |
| uc002ecp.1 | 31632066 | 31673744 | 41678 | | | | | | |
| uc002ecq.1 | 31632066 | 31678708 | 46642 | | | | | | |
| uc002ecr.1 | 31726668 | 31727675 | 1007 | | | | | | |
| uc002ecs.1 | 31792660 | 31836128 | 43468 | | | | | | |
| uc002ect.1 | 31880823 | 31881055 | 232 | | | | | | |
| uc002ecu.1 | 31970983 | 31971143 | 160 | | | | | | |
| uc002ecv.1 | 31978048 | 31978136 | 88 | | | | | | |
| uc002ecw.1 | 31984749 | 31984975 | 226 | | | | | | |
| uc002ecx.1 | 32070109 | 32071375 | 1266 | | | | | | |

Fig. 16e

Chromosome position represented
chr7:26,836,718-29,186,962
Total number of genes 22

| #name | txStart | txEnd | size | fusion gene name | Rank size order | Comparative genomics peak order | standard | actual | gene size |
|---|---|---|---|---|---|---|---|---|---|
| uc003syc.1 | 26673212 | 26870866 | 197654 | | | | | | |
| uc003syd.1 | 27099138 | 27102150 | 3012 | | | | | | |
| uc003sye.1 | 27099138 | 27102150 | 3012 | | | | | | |
| uc003syf.1 | 27099456 | 27102050 | 2594 | | | | | | |
| uc003syg.1 | 27102267 | 27106110 | 3843 | | | | | | |
| uc003syh.1 | 27106497 | 27108919 | 2422 | | | | | | |
| uc003syi.1 | 27112333 | 27120141 | 7808 | | | | | | |
| uc003syj.1 | 27112333 | 27125739 | 13406 | | | | | | |
| uc003syk.1 | 27112333 | 27133164 | 20831 | | | | | | |
| uc003syl.1 | 27128062 | 27134904 | 6842 | | | | | | |
| uc003sym.1 | 27134534 | 27136924 | 2390 | | | | | | |
| uc003syn.1 | 27147520 | 27149812 | 2292 | | | | | | |
| uc003syo.1 | 27151640 | 27153893 | 2253 | | | | | | |
| uc003syp.1 | 27153306 | 27158870 | 5564 | | | | | | |
| uc003syq.1 | 27153509 | 27158742 | 5233 | | | | | | |
| uc003syr.1 | 27158614 | 27162067 | 3453 | | | | | | |
| uc003sys.1 | 27159862 | 27162821 | 2959 | | | | | | |
| uc003syt.1 | 27168581 | 27171674 | 3093 | | | | | | |
| uc003syu.1 | 27168581 | 27181327 | 12746 | | | | | | |
| uc003syv.1 | 27176734 | 27180480 | 3746 | | | | | | |
| uc003syw.1 | 27176734 | 27186368 | 9634 | | | | | | |
| uc003syx.1 | 27187300 | 27191360 | 4060 | | | | | | |
| uc003syy.1 | 27187300 | 27191367 | 4067 | | | | | | |
| uc003syz.1 | 27191551 | 27195437 | 3886 | | | | | | |
| uc003sza.1 | 27194217 | 27195437 | 1220 | | | | | | |
| uc003szb.1 | 27203023 | 27206250 | 3227 | | | | | | |
| uc003szc.1 | 27206580 | 27208966 | 2386 | | | | | | |
| uc003szd.1 | 27248688 | 27252717 | 4029 | | | | | | |
| uc003sze.1 | 27418307 | 27419035 | 728 | | | | | | |

Fig. 17a

| #name | txStart | txEnd | size | fusion gene name | Rank size order | Comparative genomics peak order | standard | actual | gene size |
|---|---|---|---|---|---|---|---|---|---|
| uc003szf.1 | 27531585 | 27669127 | 137542 | | | | | | |
| uc003szg.1 | 27531585 | 27669127 | 137542 | | | | | | |
| uc003szh.1 | 27531585 | 27669127 | 137542 | | | | | | |
| uc003szi.1 | 27546024 | 27655767 | 109743 | | | | | | |
| uc003szj.1 | 27622117 | 27633636 | 11519 | | | | | | |
| uc003szk.1 | 27746262 | 27835911 | 89649 | | | | | | |
| uc003szl.1 | 27746262 | 27835911 | 89649 | | | | | | |
| uc003szm.1 | 27836717 | 27998200 | 161483 | | | | | | |
| uc003szn.1 | 27836717 | 28186962 uc003szn.1 | 350245 | JAZF1 | 2 | 4 | 12 | 0 | 6 |
| uc003szo.1 | 28305464 | 28832036 | 526572 | | | | | | |
| uc003szp.1 | 28415519 | 28416897 | 1378 | | | | | | |
| uc003szq.1 | 28418668 | 28832036 | 413368 | | | | | | |
| uc003szr.1 | 28441758 | 28832036 | 390278 | | | | | | |
| uc003szs.1 | 28692245 | 28832036 | 139791 | | | | | | |
| uc003szt.1 | 28959498 | 28964554 | 5056 | | | | | | |
| uc003szu.1 | 28965271 | 28965301 | 30 | | | | | | |
| uc003szv.1 | 29001771 | 29152678 | 150907 | | | | | | |
| uc003szw.1 | 29001771 | 29152678 | 150907 | | | | | | |
| uc003szx.1 | 29001771 | 29201417 | 199646 | | | | | | |
| uc003szy.1 | 29007180 | 29019508 | 12328 | | | | | | |

Fig. 17b

Chromosome position represented
chr18:53,489,598-55,568,350
Total number of genes   11

| #name | txStart | txEnd | size | fusion gene name | Rank size order | Comparative genomics peak order | standard | actual | gene size |
|---|---|---|---|---|---|---|---|---|---|
| uc002lgv.1 | 53457684 | 53556274 | 98590 | | | | | | |
| uc002lgw.1 | 53464656 | 53550037 | 85381 | | | | | | |
| uc002lgx.1 | 53862777 | 54216369 | 353592 | | | | | | |
| uc002lgy.1 | 53862777 | 54216369 | 353592 | | | | | | |
| uc002lgz.1 | 53862777 | 54216369 | 353592 | | | | | | |
| uc002lha.1 | 53863926 | 53984091 | 120165 | | | | | | |
| uc002lhb.1 | 53967562 | 54216369 | 248807 | | | | | | |
| uc002lhc.1 | 53967562 | 54216369 | 248807 | | | | | | |
| uc002lhd.1 | 53967562 | 54216369 | 248807 | | | | | | |
| uc002lhe.1 | 53967562 | 54216369 | 248807 | | | | | | |
| uc002lhf.1 | 54013679 | 54216369 | 202690 | | | | | | |
| uc002lhg.1 | 54039746 | 54216369 | 176623 | | | | | | |
| uc002lhh.1 | 54063638 | 54216369 | 152731 | | | | | | |
| uc002lhi.1 | 54216410 | 54219711 | 3301 | | | | | | |
| uc002lhj.1 | 54299461 | 54398760 | 99299 | | | | | | |
| uc002lhk.1 | 54346963 | 54356436 | 9473 | | | | | | |
| uc002lhl.1 | 54353045 | 54447169 | 94124 | | | | | | |
| uc002lhm.1 | 54489597 | 54568350 | 78753 | | | | | | |
| uc002lhn.1 | 54489597 | 54568350 uc002lhn.1 | 78753 | MALT1 | b5 | 1 | 8 | 3 | 2 |
| uc002lho.1 | 54681040 | 54804689 | 123649 | | | | | | |
| uc002lhp.1 | 54681040 | 54804689 | 123649 | | | | | | |
| uc002lhq.1 | 54681828 | 54804689 | 122861 | | | | | | |
| uc002lhr.1 | 54682397 | 54804689 | 122292 | | | | | | |
| uc002lhs.1 | 54682835 | 54804689 | 121854 | | | | | | |
| uc002lht.1 | 54958104 | 54977043 | 18939 | | | | | | |
| uc002lhu.1 | 55038379 | 55048982 | 10603 | | | | | | |
| uc002lhv.1 | 55038379 | 55048982 | 10603 | | | | | | |
| uc002lhw.1 | 55038379 | 55048982 | 10603 | | | | | | |
| uc002lhx.1 | 55085246 | 55091605 | 6359 | | | | | | |

Fig. 18a

| #name | txStart | txEnd | size | fusion gene name | Rank size order | Comparative genomics peak order | standard | actual | gene size |
|---|---|---|---|---|---|---|---|---|---|
| uc002lhy.1 | 55113633 | 55136861 | 23228 | | | | | | |
| uc002lhz.1 | 55148087 | 55177461 | 29374 | | | | | | |
| uc002lia.1 | 55252126 | 55273421 | 21295 | | | | | | |
| uc002lib.1 | 55252126 | 55515570 | 263444 | | | | | | |

Fig. 18b

Chromosome position represented chr19:5,161,392-7,230,959
Total number of genes 55

| #name | txStart | txEnd | size | fusion gene name | Rank size order | Comparative genomics peak order | standard | actual | gene size |
|---|---|---|---|---|---|---|---|---|---|
| uc002mbu.1 | 5109505 | 5291814 | 182309 | | | | | | |
| uc002mbv.1 | 5156518 | 5291814 | 135296 | | | | | | |
| uc002mbw.1 | 5156518 | 5291814 | 135296 | | | | | | |
| uc002mbx.1 | 5156518 | 5291814 | 135296 | | | | | | |
| uc002mby.1 | 5156518 | 5291814 | 135296 | | | | | | |
| uc002mbz.1 | 5224074 | 5237399 | 13325 | | | | | | |
| uc002mca.1 | 5406441 | 5407867 | 1426 | | | | | | |
| uc002mcb.1 | 5509177 | 5510391 | 1214 | | | | | | |
| uc002mcc.1 | 5510363 | 5518965 | 8602 | | | | | | |
| uc002mcd.1 | 5538009 | 5573938 | 35929 | | | | | | |
| uc002mce.1 | 5574163 | 5615170 | 41007 | | | | | | |
| uc002mcf.1 | 5574163 | 5619489 | 45326 | | | | | | |
| uc002mcg.1 | 5574163 | 5619489 | 45326 | | | | | | |
| uc002mch.1 | 5629432 | 5631911 | 2479 | | | | | | |
| uc002mci.1 | 5629937 | 5631911 | 1974 | | | | | | |
| uc002mcj.1 | 5632034 | 5636596 | 4562 | | | | | | |
| uc002mck.1 | 5632034 | 5639533 | 7499 | | | | | | |
| uc002mcl.1 | 5632034 | 5639533 | 7499 | | | | | | |
| uc002mcm.1 | 5632034 | 5639533 | 7499 | | | | | | |
| uc002mcn.1 | 5632034 | 5639533 | 7499 | | | | | | |
| uc002mco.1 | 5632034 | 5639533 | 7499 | | | | | | |
| uc002mcp.1 | 5632034 | 5639533 | 7499 | | | | | | |
| uc002mcq.1 | 5632034 | 5639533 | 7499 | | | | | | |
| uc002mcr.1 | 5632034 | 5639533 | 7499 | | | | | | |
| uc002mcs.1 | 5632034 | 5639533 | 7499 | | | | | | |
| uc002mct.1 | 5632034 | 5639533 | 7499 | | | | | | |
| uc002mcu.1 | 5632034 | 5639533 | 7499 | | | | | | |
| uc002mcv.1 | 5641271 | 5642678 | 1407 | | | | | | |
| uc002mcw.1 | 5641345 | 5642678 | 1333 | | | | | | |

Fig. 19a

| #name | txStart | txEnd | size | fusion gene name | Rank size order | Comparative genomics peak order | standard | actual | gene size |
|---|---|---|---|---|---|---|---|---|---|
| uc002mcx.1 | 5642844 | 5671176 | 28332 | | | | | | |
| uc002mcy.1 | 5642844 | 5671176 | 28332 | | | | | | |
| uc002mcz.1 | 5642844 | 5671463 | 28619 | | | | | | |
| uc002mda.1 | 5671687 | 5729742 | 58055 | | | | | | |
| uc002mdb.1 | 5733970 | 5735610 | 1640 | | | | | | |
| uc002mdc.1 | 5736152 | 5742190 | 6038 | | | | | | |
| uc002mdd.1 | 5736152 | 5742190 | 6038 | | | | | | |
| uc002mde.1 | 5774817 | 5779335 | 4518 | | | | | | |
| uc002mdf.1 | 5781636 | 5790028 | 8392 | | | | | | |
| uc002mdg.1 | 5781636 | 5790742 | 9106 | | | | | | |
| uc002mdh.1 | 5781636 | 5790742 | 9106 | | | | | | |
| uc002mdi.1 | 5782388 | 5783578 | 1190 | | | | | | |
| uc002mdj.1 | 5793901 | 5802482 | 8581 | | | | | | |
| uc002mdk.1 | 5793901 | 5802482 | 8581 | | | | | | |
| uc002mdl.1 | 5793901 | 5802482 | 8581 | | | | | | |
| uc002mdm.1 | 5793901 | 5802482 | 8581 | | | | | | |
| uc002mdn.1 | 5798477 | 5809250 | 10773 | | | | | | |
| uc002mdo.1 | 5816836 | 5821551 | 4715 | | | | | | |
| uc002mdp.1 | 5842286 | 5855025 | 12739 | | | | | | |
| uc002mdq.1 | 5845685 | 5855025 | 9340 | | | | | | |
| uc002mdr.1 | 5845685 | 5855025 | 9340 | | | | | | |
| uc002mds.1 | 5855896 | 5861263 | 5367 | | | | | | |
| uc002mdt.1 | 5865218 | 5866886 | 1668 | | | | | | |
| uc002mdu.1 | 5865218 | 5866886 | 1668 | | | | | | |
| uc002mdv.1 | 5867151 | 5885473 | 18322 | | | | | | |
| uc002mdw.1 | 5867151 | 5929113 | 61962 | | | | | | |
| uc002mdx.1 | 5867151 | 5929113 | 61962 | | | | | | |
| uc002mdy.1 | 5867151 | 5929113 | 61962 | | | | | | |
| uc002mdz.1 | 5867151 | 5929113 | 61962 | | | | | | |
| uc002mea.1 | 5867151 | 5929113 | 61962 | | | | | | |
| uc002meb.1 | 5944512 | 6061554 | 117042 | | | | | | |
| uc002mec.1 | 5944512 | 6061554 | 117042 | | | | | | |
| uc002med.1 | 5957493 | 5959625 | 2132 | | | | | | |

Fig. 19b

| #name | txStart | txEnd | | size | fusion gene name | Rank size order | Comparative genomics peak order | standard | actual | gene size |
|---|---|---|---|---|---|---|---|---|---|---|
| uc002mee.1 | 6086650 | 6144112 | | 57462 | | | | | | |
| uc002mef.1 | 6086679 | 6144112 | | 57433 | | | | | | |
| uc002meg.1 | 6086684 | 6144112 | | 57428 | | | | | | |
| uc002meh.1 | 6086709 | 6144112 | | 57403 | | | | | | |
| uc002mei.1 | 6086709 | 6144112 | | 57403 | | | | | | |
| uc002mej.1 | 6140738 | 6150540 | | 9802 | | | | | | |
| uc002mek.1 | 6161391 | 6230959 | uc002mek.1 | 69568 | mll1 (enl) | 5 | 1 | 8 | 3 | 2 |
| uc002mel.1 | 6257724 | 6284562 | | 26838 | | | | | | |
| uc002mem.1 | 6312462 | 6319915 | | 7453 | | | | | | |
| uc002men.1 | 6317250 | 6319915 | | 2665 | | | | | | |
| uc002meo.1 | 6323443 | 6326040 | | 2597 | | | | | | |
| uc002mep.1 | 6326304 | 6326860 | | 556 | | | | | | |
| uc002meq.1 | 6330580 | 6344184 | | 13604 | | | | | | |
| uc002mer.1 | 6364358 | 6375805 | | 11447 | | | | | | |
| uc002mes.1 | 6377047 | 6384773 | | 7726 | | | | | | |
| uc002met.1 | 6377049 | 6384773 | | 7724 | | | | | | |
| uc002meu.1 | 6387091 | 6395312 | | 8221 | | | | | | |
| uc002mev.1 | 6387091 | 6410781 | | 23690 | | | | | | |
| uc002mew.1 | 6387431 | 6395312 | | 7881 | | | | | | |
| uc002mex.1 | 6391074 | 6410781 | | 19707 | | | | | | |
| uc002mey.1 | 6414787 | 6418230 | | 3443 | | | | | | |
| uc002mez.1 | 6415259 | 6418230 | | 2971 | | | | | | |
| uc002mfa.1 | 6415259 | 6418230 | | 2971 | | | | | | |
| uc002mfb.1 | 6418217 | 6427257 | | 9040 | | | | | | |
| uc002mfc.1 | 6418217 | 6427257 | | 9040 | | | | | | |
| uc002mfd.1 | 6418217 | 6431300 | | 13083 | | | | | | |
| uc002mfe.1 | 6418217 | 6432798 | | 14581 | | | | | | |
| uc002mff.1 | 6445329 | 6453320 | | 7991 | | | | | | |
| uc002mfg.1 | 6445329 | 6453330 | | 8001 | | | | | | |
| uc002mfh.1 | 6482036 | 6486933 | | 4897 | | | | | | |
| uc002mfi.1 | 6536849 | 6542163 | | 5314 | | | | | | |
| uc002mfj.1 | 6615565 | 6621599 | | 6034 | | | | | | |
| uc002mfk.1 | 6615565 | 6621599 | | 6034 | | | | | | |

Fig. 19c

| #name | txStart | txEnd | size | fusion gene name | Rank size order | Comparative genomics peak order | standard | actual | gene size |
|---|---|---|---|---|---|---|---|---|---|
| uc002mfl.1 | 6628845 | 6644094 | 15249 | | | | | | |
| uc002mfm.1 | 6628845 | 6671662 | 42817 | | | | | | |
| uc002mfn.1 | 6680924 | 6687722 | 6798 | | | | | | |
| uc002mfo.1 | 6680924 | 6688271 | 7347 | | | | | | |
| uc002mfp.1 | 6680924 | 6688633 | 7709 | | | | | | |
| uc002mfq.1 | 6690706 | 6702337 | 11631 | | | | | | |
| uc002mfr.1 | 6690706 | 6702529 | 11823 | | | | | | |
| uc002mfs.1 | 6690706 | 6702529 | 11823 | | | | | | |
| uc002mft.1 | 6703172 | 6718480 | 15308 | | | | | | |
| uc002mfu.1 | 6723721 | 6808371 | 84650 | | | | | | |
| uc002mfv.1 | 6735128 | 6808371 | 73243 | | | | | | |
| uc002mfw.1 | 6838581 | 6891464 | 52883 | | | | | | |
| uc002mfx.1 | 6908003 | 6946250 | 38247 | | | | | | |
| uc002mfy.1 | 6955970 | 6957394 | 1424 | | | | | | |
| uc002mfz.1 | 7000349 | 7002748 | 2399 | | | | | | |
| uc002mga.1 | 7020470 | 7038978 | 18508 | | | | | | |
| uc002mgb.1 | 7020470 | 7038978 | 18508 | | | | | | |
| uc002mgc.1 | 7020470 | 7038978 | 18508 | | | | | | |
| uc002mgd.1 | 7063265 | 7245011 | 181746 | | | | | | |
| uc002mge.1 | 7063265 | 7245011 | 181746 | | | | | | |
| uc002mgf.1 | 7102994 | 7245011 | 142017 | | | | | | |

Fig. 19d

Chromosome position represented
chr11:116,812,415-118,901,146
Total number of genes 50

| #name | txStart | txEnd | size | fusion gene name | Rank size order | Comparative genomics peak order | standard | actual | gene size |
|---|---|---|---|---|---|---|---|---|---|
| uc001prh.1 | 116803698 | 117173186 | 369488 | | | | | | |
| uc001pri.1 | 116894299 | 117193450 | 299151 | | | | | | |
| uc001prj.1 | 117195999 | 117200644 | 4645 | | | | | | |
| uc001prk.1 | 117195999 | 117204017 | 8018 | | | | | | |
| uc001prl.1 | 117197164 | 117200644 | 3480 | | | | | | |
| uc001prm.1 | 117212902 | 117215446 | 2544 | | | | | | |
| uc001prn.1 | 117212902 | 117218716 | 5814 | | | | | | |
| uc001pro.1 | 117212902 | 117252577 | 39675 | | | | | | |
| uc001prp.1 | 117212902 | 117252577 | 39675 | | | | | | |
| uc001prq.1 | 117212902 | 117252577 | 39675 | | | | | | |
| uc001prr.1 | 117212902 | 117252577 | 39675 | | | | | | |
| uc001prs.1 | 117276569 | 117305325 | 28756 | | | | | | |
| uc001prt.1 | 117278969 | 117294763 | 15794 | | | | | | |
| uc001pru.1 | 117283719 | 117305325 | 21606 | | | | | | |
| uc001prv.1 | 117362318 | 117377404 | 15086 | | | | | | |
| uc001prw.1 | 117362661 | 117377404 | 14743 | | | | | | |
| uc001prx.1 | 117391696 | 117462718 | 71022 | | | | | | |
| uc001pry.1 | 117391696 | 117462718 | 71022 | | | | | | |
| uc001prz.1 | 117391696 | 117462718 | 71022 | | | | | | |
| uc001psa.1 | 117391696 | 117462718 | 71022 | | | | | | |
| uc001psb.1 | 117452975 | 117494380 | 41405 | | | | | | |
| uc001psc.1 | 117452975 | 117494380 | 41405 | | | | | | |
| uc001psd.1 | 117470746 | 117494380 | 23634 | | | | | | |
| uc001pse.1 | 117509301 | 117528745 | 19444 | | | | | | |
| uc001psf.1 | 117538728 | 117552546 | 13818 | | | | | | |
| uc001psg.1 | 117569887 | 117580161 | 10274 | | | | | | |
| uc001psh.1 | 117569887 | 117588983 | 19096 | | | | | | |
| uc001psi.1 | 117569887 | 117589284 | 19397 | | | | | | |
| uc001psj.1 | 117569887 | 117590811 | 20924 | | | | | | |

Fig. 20a

| #name | txStart | txEnd | size | fusion gene name | Rank size order | Comparative genomics peak order | standard | actual | gene size |
|---|---|---|---|---|---|---|---|---|---|
| uc001psk.1 | 117569887 | 117600932 | 31045 | | | | | | |
| uc001psl.1 | 117573922 | 117588983 | 15061 | | | | | | |
| uc001psm.1 | 117605545 | 117628221 | 22676 | | | | | | |
| uc001psn.1 | 117629343 | 117640219 | 10876 | | | | | | |
| uc001pso.1 | 117632837 | 117640219 | 7382 | | | | | | |
| uc001psp.1 | 117635161 | 117640219 | 5058 | | | | | | |
| uc001psq.1 | 117680661 | 117692100 | 11439 | | | | | | |
| uc001psr.1 | 117688520 | 117692100 | 3580 | | | | | | |
| uc001pss.1 | 117714998 | 117718669 | 3671 | | | | | | |
| uc001pst.1 | 117714998 | 117718669 | 3671 | | | | | | |
| uc001psu.1 | 117720310 | 117729261 | 8951 | | | | | | |
| uc001psv.1 | 117735511 | 117775136 | 39625 | | | | | | |
| uc001psw.1 | 117735511 | 117775136 | 39625 | | | | | | |
| uc001psx.1 | 117777313 | 117785772 | 8459 | | | | | | |
| uc001psy.1 | 117809065 | 117811130 | 2065 | | | | | | |
| uc001psz.1 | 117812414 | 117850240 | 37826 | | | | | | |
| uc001pta.1 | 117812414 | 117901146 | 88732 | | | | | | |
| uc001ptb.1 | 117812414 | 117901146 uc001ptb.1 | 88732 | mll | 4 | 1 | 8 | 0 | 2 |
| uc001ptc.1 | 117813153 | 117815083 | 1930 | | | | | | |
| uc001ptd.1 | 117844699 | 117852907 | 8208 | | | | | | |
| uc001pte.1 | 117857639 | 117867853 | 10214 | | | | | | |
| uc001ptf.1 | 117900882 | 117902749 | 1867 | | | | | | |
| uc001ptg.1 | 117903419 | 117906950 | 3531 | | | | | | |
| uc001pth.1 | 117907133 | 117911539 | 4406 | | | | | | |
| uc001pti.1 | 117907133 | 117911539 | 4406 | | | | | | |
| uc001ptj.1 | 117907133 | 117911758 | 4625 | | | | | | |
| uc001ptk.1 | 117907133 | 117911758 | 4625 | | | | | | |
| uc001ptl.1 | 117907133 | 117923209 | 16076 | | | | | | |
| uc001ptm.1 | 117907133 | 117923209 | 16076 | | | | | | |
| uc001ptn.1 | 117907699 | 117923209 | 15510 | | | | | | |
| uc001pto.1 | 117920468 | 117941960 | 21492 | | | | | | |
| uc001ptp.1 | 117920468 | 117941960 | 21492 | | | | | | |
| uc001ptq.1 | 117948320 | 117978855 | 30535 | | | | | | |

Fig. 20b

| #name | txStart | txEnd | size | fusion gene name | Rank size order | Comparative genomics peak order | standard | actual | gene size |
|---|---|---|---|---|---|---|---|---|---|
| uc001ptr.1 | 117982422 | 118033951 | 51529 | | | | | | |
| uc001pts.1 | 117983540 | 118033951 | 50411 | | | | | | |
| uc001ptt.1 | 117983540 | 118033951 | 50411 | | | | | | |
| uc001ptu.1 | 117983660 | 118033951 | 50291 | | | | | | |
| uc001ptv.1 | 118003230 | 118033951 | 30721 | | | | | | |
| uc001ptw.1 | 118005904 | 118033951 | 28047 | | | | | | |
| uc001ptx.1 | 118007839 | 118033951 | 26112 | | | | | | |
| uc001pty.1 | 118034151 | 118055591 | 21440 | | | | | | |
| uc001ptz.1 | 118034151 | 118055591 | 21440 | | | | | | |
| uc001pua.1 | 118125622 | 118135288 | 9666 | | | | | | |
| uc001pub.1 | 118125622 | 118166798 | 41176 | | | | | | |
| uc001puc.1 | 118125622 | 118167082 | 41460 | | | | | | |
| uc001pud.1 | 118143567 | 118167082 | 23515 | | | | | | |
| uc001pue.1 | 118259776 | 118272181 | 12405 | | | | | | |
| uc001puf.1 | 118269310 | 118272181 | 2871 | | | | | | |
| uc001pug.1 | 118272060 | 118286823 | 14763 | | | | | | |
| uc001puh.1 | 118332235 | 118334479 | 2244 | | | | | | |
| uc001pui.1 | 118347626 | 118357205 | 9579 | | | | | | |
| uc001puj.1 | 118347626 | 118357205 | 9579 | | | | | | |
| uc001puk.1 | 118354701 | 118357205 | 2504 | | | | | | |
| uc001pul.1 | 118374061 | 118391665 | 17604 | | | | | | |
| uc001pum.1 | 118378880 | 118379513 | 633 | | | | | | |
| uc001pun.1 | 118391632 | 118394267 | 2635 | | | | | | |
| uc001puo.1 | 118394450 | 118399592 | 5142 | | | | | | |
| uc001pup.1 | 118394676 | 118399592 | 4916 | | | | | | |
| uc001puq.1 | 118400273 | 118405484 | 5211 | | | | | | |
| uc001pur.1 | 118400273 | 118406629 | 6356 | | | | | | |
| uc001pus.1 | 118400273 | 118406800 | 6527 | | | | | | |
| uc001put.1 | 118420109 | 118431765 | 11656 | | | | | | |
| uc001puu.1 | 118420109 | 118433055 | 12946 | | | | | | |
| uc001puv.1 | 118420109 | 118433122 | 13013 | | | | | | |
| uc001puw.1 | 118424939 | 118432992 | 8053 | | | | | | |
| uc001pux.1 | 118431106 | 118433122 | 2016 | | | | | | |

Fig. 20c

| #name | txStart | txEnd | size | fusion gene name | Rank size order | Comparative genomics peak order | standard | actual | gene size |
|---|---|---|---|---|---|---|---|---|---|
| uc001puy.1 | 118443702 | 118457898 | 14196 | | | | | | |
| uc001puz.1 | 118460796 | 118469469 | 8673 | | | | | | |
| uc001pva.1 | 118460796 | 118469469 | 8673 | | | | | | |
| uc001pvb.1 | 118460796 | 118469469 | 8673 | | | | | | |
| uc001pvc.1 | 118460796 | 118469469 | 8673 | | | | | | |
| uc001pvd.1 | 118460804 | 118469469 | 8665 | | | | | | |
| uc001pve.1 | 118460804 | 118469469 | 8665 | | | | | | |
| uc001pvf.1 | 118463906 | 118469469 | 5563 | | | | | | |
| uc001pvg.1 | 118469794 | 118471387 | 1593 | | | | | | |
| uc001pvh.1 | 118469798 | 118471369 | 1571 | | | | | | |
| uc001pvi.1 | 118472422 | 118477995 | 5573 | | | | | | |
| uc001pvj.1 | 118472422 | 118477995 | 5573 | | | | | | |
| uc001pvk.1 | 118472422 | 118478062 | 5640 | | | | | | |
| uc001pvl.1 | 118472422 | 118484251 | 11829 | | | | | | |
| uc001pvm.1 | 118472430 | 118476763 | 4333 | | | | | | |
| uc001pvn.1 | 118483302 | 118493037 | 9735 | | | | | | |
| uc001pvo.1 | 118483302 | 118493037 | 9735 | | | | | | |
| uc001pvp.1 | 118497497 | 118510975 | 13478 | | | | | | |
| uc001pvq.1 | 118497497 | 118510975 | 13478 | | | | | | |
| uc001pvr.1 | 118507358 | 118510975 | 3617 | | | | | | |
| uc001pvs.1 | 118524959 | 118538584 | 13625 | | | | | | |
| uc001pvt.1 | 118529937 | 118530063 | 126 | | | | | | |
| uc001pvu.1 | 118544646 | 118559936 | 15290 | | | | | | |
| uc001pvv.1 | 118544649 | 118559936 | 15287 | | | | | | |
| uc001pvw.1 | 118544649 | 118559936 | 15287 | | | | | | |
| uc001pvx.1 | 118544689 | 118559936 | 15247 | | | | | | |
| uc001pvy.1 | 118561404 | 118566130 | 4726 | | | | | | |
| uc001pvz.1 | 118561404 | 118566130 | 4726 | | | | | | |
| uc001pwa.1 | 118561404 | 118566130 | 4726 | | | | | | |
| uc001pwb.1 | 118561418 | 118566130 | 4712 | | | | | | |
| uc001pwc.1 | 118566188 | 118569805 | 3617 | | | | | | |
| uc001pwd.1 | 118566188 | 118582119 | 15931 | | | | | | |
| uc001pwe.1 | 118582199 | 118684069 | 101870 | | | | | | |

Fig. 20d

| #name | txStart | txEnd | size | fusion gene name | Rank size order | Comparative genomics peak order | standard | actual | gene size |
|---|---|---|---|---|---|---|---|---|---|
| uc001pwf.1 | 118684443 | 186693050 | 8607 | | | | | | |
| uc001pwg.1 | 118685542 | 118686823 | 1281 | | | | | | |
| uc001pwh.1 | 118710446 | 118713232 | 2786 | | | | | | |
| uc001pwi.1 | 118714861 | 118717692 | 2831 | | | | | | |
| uc001pwj.1 | 118714861 | 118722580 | 7719 | | | | | | |
| uc001pwk.1 | 118716614 | 118722580 | 5966 | | | | | | |
| uc001pwl.1 | 118732162 | 118740102 | 7940 | | | | | | |
| uc001pwm.1 | 118732162 | 118757575 | 25413 | | | | | | |
| uc001pwn.1 | 118732162 | 118757575 | 25413 | | | | | | |
| uc001pwo.1 | 118757729 | 118876516 | 118787 | | | | | | |
| uc001pwp.1 | 118757729 | 118902584 | 144855 | | | | | | |
| uc001pwq.1 | 118794097 | 118796859 | 2762 | | | | | | |
| uc001pwr.1 | 118794097 | 118799064 | 4967 | | | | | | |
| uc001pws.1 | 118794097 | 118799064 | 4967 | | | | | | |

Fig. 20e

Chromosome position represented
chr9:19,334,968-21,612,450
Total number of genes: 31

| #name | txStart | txEnd | | size | fusion gene name | Rank size order | Comparative genomics peak order | standard | actual | gene size |
|---|---|---|---|---|---|---|---|---|---|---|
| uc003znq.1 | 19280701 | 19364139 | | 83438 | | | | | | |
| uc003znr.1 | 19330963 | 19364137 | | 33174 | | | | | | |
| uc003zns.1 | 19332630 | 19364139 | | 31509 | | | | | | |
| uc003znt.1 | 19335918 | 19347693 | | 11775 | | | | | | |
| uc003znu.1 | 19366253 | 19370215 | | 3962 | | | | | | |
| uc003znv.1 | 19366253 | 19370235 | | 3982 | | | | | | |
| uc003znw.1 | 19368358 | 19369616 | | 1258 | | | | | | |
| uc003znx.1 | 19387806 | 19441790 | | 53984 | | | | | | |
| uc003zny.1 | 19398924 | 19442500 | | 43576 | | | | | | |
| uc003znz.1 | 19398924 | 19442500 | | 43576 | | | | | | |
| uc003zoa.1 | 19505977 | 19776926 | | 270949 | | | | | | |
| uc003zob.1 | 19505977 | 19776926 | | 270949 | | | | | | |
| uc003zoc.1 | 19776909 | 19778103 | | 1194 | | | | | | |
| uc003zod.1 | 19776909 | 19778808 | | 1899 | | | | | | |
| uc003zoe.1 | 20334967 | 20612450 | uc003zoe.1 | 277483 | mllt3 | 1 | 1 | 11 | 0 | 5 |
| uc003zof.1 | 20352724 | 20612450 | | 259726 | | | | | | |
| uc003zog.1 | 20648308 | 20985954 | | 337646 | | | | | | |
| uc003zoh.1 | 20810292 | 20985954 | | 175662 | | | | | | |
| uc003zoi.1 | 20993622 | 21021635 | | 28013 | | | | | | |
| uc003zoj.1 | 20996364 | 21021567 | | 25203 | | | | | | |
| uc003zok.1 | 21067103 | 21067943 | | 840 | | | | | | |
| uc003zol.1 | 21130630 | 21132144 | | 1514 | | | | | | |
| uc003zom.1 | 21155635 | 21156619 | | 984 | | | | | | |
| uc003zon.1 | 21176692 | 21177670 | | 978 | | | | | | |
| uc003zoo.1 | 21191233 | 21229990 | | 38757 | | | | | | |
| uc003zop.1 | 21191467 | 21192204 | | 737 | | | | | | |
| uc003zoq.1 | 21196179 | 21197142 | | 963 | | | | | | |
| uc003zor.1 | 21206371 | 21207310 | | 939 | | | | | | |
| uc003zos.1 | 21217241 | 21218221 | | 980 | | | | | | |

Fig. 21a

| #name | txStart | txEnd | size | fusion gene name | Rank size order | Comparative genomics peak order | standard | actual | gene size |
|---|---|---|---|---|---|---|---|---|---|
| uc003zot.1 | 21229200 | 21230046 | 846 | | | | | | |
| uc003zou.1 | 21267686 | 21268562 | 876 | | | | | | |
| uc003zov.1 | 21294685 | 21295255 | 570 | | | | | | |
| uc003zow.1 | 21314051 | 21325352 | 11301 | | | | | | |
| uc003zox.1 | 21314051 | 21325388 | 11337 | | | | | | |
| uc003zoy.1 | 21321017 | 21325429 | 4412 | | | | | | |
| uc003zoz.1 | 21340316 | 21340886 | 570 | | | | | | |
| uc003zpa.1 | 21357422 | 21358075 | 653 | | | | | | |
| uc003zpb.1 | 21374253 | 21375396 | 1143 | | | | | | |
| uc003zpc.1 | 21399145 | 21400184 | 1039 | | | | | | |
| uc003zpd.1 | 21430439 | 21431315 | 876 | | | | | | |
| uc003zpe.1 | 21444269 | 21549697 | 105428 | | | | | | |
| uc003zpf.1 | 21444269 | 21549832 | 105563 | | | | | | |
| uc003zpg.1 | 21470838 | 21472312 | 1474 | | | | | | |

Fig. 21b

Chromosome position represented
chr8:40,907,427-43,028,635
Total number of genes: 19

| #name | txStart | txEnd | size | fusion gene name | Rank size order | Comparative genomics peak order | standard | actual | gene size |
|---|---|---|---|---|---|---|---|---|---|
| uc003xnt.1 | 41238634 | 41286137 | 47503 | | | | | | |
| uc003xnu.1 | 41467237 | 41487656 | 20419 | | | | | | |
| uc003xnv.1 | 41467237 | 41487656 | 20419 | | | | | | |
| uc003xnw.1 | 41467329 | 41487656 | 20327 | | | | | | |
| uc003xnx.1 | 41505902 | 41519059 | 13157 | | | | | | |
| uc003xny.1 | 41505912 | 41521399 | 15487 | | | | | | |
| uc003xnz.1 | 41554875 | 41597971 | 43096 | | | | | | |
| uc003xoa.1 | 41622985 | 41624035 | 1050 | | | | | | |
| uc003xob.1 | 41629900 | 41642241 | 12341 | | | | | | |
| uc003xoc.1 | 41629900 | 41642241 | 12341 | | | | | | |
| uc003xod.1 | 41629900 | 41642241 | 12341 | | | | | | |
| uc003xoe.1 | 41629900 | 41642241 | 12341 | | | | | | |
| uc003xof.1 | 41629900 | 41642241 | 12341 | | | | | | |
| uc003xog.1 | 41629900 | 41642241 | 12341 | | | | | | |
| uc003xoh.1 | 41629900 | 41682916 | 53016 | | | | | | |
| uc003xoi.1 | 41629900 | 41774297 | 144397 | | | | | | |
| uc003xoj.1 | 41629900 | 41774297 | 144397 | | | | | | |
| uc003xok.1 | 41629900 | 41774297 | 144397 | | | | | | |
| uc003xol.1 | 41629900 | 41774297 | 144397 | | | | | | |
| uc003xom.1 | 41629900 | 41873437 | 243537 | | | | | | |
| uc003xon.1 | 41907426 | 42028635 uc003xon.1 | 121209 | MYST3 | 4 | 1 | 9 | 0 | 3 |
| uc003xoo.1 | 42129760 | 42147858 | 18098 | | | | | | |
| uc003xop.1 | 42129760 | 42147858 | 18098 | | | | | | |
| uc003xoq.1 | 42131290 | 42143037 | 11747 | | | | | | |
| uc003xor.1 | 42131290 | 42143037 | 11747 | | | | | | |
| uc003xos.1 | 42151909 | 42184351 | 32442 | | | | | | |
| uc003xot.1 | 42151909 | 42184351 | 32442 | | | | | | |
| uc003xou.1 | 42151909 | 42184351 | 32442 | | | | | | |
| uc003xov.1 | 42247985 | 42293886 | 45901 | | | | | | |

Fig. 22a

| #name | txStart | txEnd | size | fusion gene name | Rank size order | Comparative genomics peak order | standard | actual | gene size |
|---|---|---|---|---|---|---|---|---|---|
| uc003xow.1 | 42247985 | 42309122 | 61137 | | | | | | |
| uc003xox.1 | 42247985 | 42309122 | 61137 | | | | | | |
| uc003xoy.1 | 42306710 | 42309122 | 2412 | | | | | | |
| uc003xoz.1 | 42315186 | 42348470 | 33284 | | | | | | |
| uc003xpa.1 | 42315186 | 42348470 | 33284 | | | | | | |
| uc003xpb.1 | 42350742 | 42353831 | 3089 | | | | | | |
| uc003xpc.1 | 42368546 | 42382572 | 14026 | | | | | | |
| uc003xpd.1 | 42368546 | 42382572 | 14026 | | | | | | |
| uc003xpe.1 | 42393149 | 42516225 | 123076 | | | | | | |
| uc003xpf.1 | 42509238 | 42515803 | 6565 | | | | | | |
| uc003xpg.1 | 42515907 | 42527280 | 11373 | | | | | | |
| uc003xph.1 | 42515912 | 42527280 | 11368 | | | | | | |
| uc003xpi.1 | 42671718 | 42711366 | 39648 | | | | | | |
| uc003xpj.1 | 42726936 | 42742776 | 15840 | | | | | | |
| uc003xpk.1 | 42810973 | 42817631 | 6658 | | | | | | |
| uc003xpl.1 | 42810973 | 42817631 | 6658 | | | | | | |
| uc003xpm.1 | 42829547 | 42870939 | 41392 | | | | | | |
| uc003xpn.1 | 42829547 | 42870939 | 41392 | | | | | | |
| uc003xpo.1 | 42829547 | 42870955 | 41408 | | | | | | |
| uc003xpp.1 | 42829547 | 42870955 | 41408 | | | | | | |
| uc003xpq.1 | 42835643 | 42870939 | 35296 | | | | | | |
| uc003xpr.1 | 42871189 | 42994084 | 122895 | | | | | | |

Fig. 22b

Chromosome position represented
chr5:169,746,725-171,770,493
Total number of genes  13

| #name | txStart | txEnd | size | fusion gene name | Rank size order | Comparative genomics peak order | standard | actual | gene size |
|---|---|---|---|---|---|---|---|---|---|
| uc003map.1 | 169713458 | 170096214 | 382756 | | | | | | |
| uc003maq.1 | 169737744 | 169749216 | 11472 | | | | | | |
| uc003mar.1 | 169742255 | 169749216 | 6961 | | | | | | |
| uc003mas.1 | 169863625 | 170096214 | 232589 | | | | | | |
| uc003mat.1 | 169863625 | 170096214 | 232589 | | | | | | |
| uc003mau.1 | 170143342 | 170173628 | 30286 | | | | | | |
| uc003mav.1 | 170154789 | 170173628 | 18839 | | | | | | |
| uc003maw.1 | 170221599 | 170270920 | 49321 | | | | | | |
| uc003max.1 | 170221599 | 170530895 | 309296 | | | | | | |
| uc003may.1 | 170221599 | 170530895 | 309296 | | | | | | |
| uc003maz.1 | 170221599 | 170530895 | 309296 | | | | | | |
| uc003mba.1 | 170502875 | 170659624 | 438025 | | | | | | |
| uc003mbb.1 | 170542775 | 170659624 | 156749 | | | | | | |
| uc003mbc.1 | 170542775 | 170567512 | 24737 | | | | | | |
| uc003mbd.1 | 170542775 | 170602673 | 59898 | | | | | | |
| uc003mbe.1 | 170665589 | 170668364 | 2775 | | | | | | |
| uc003mbf.1 | 170668892 | 170671743 | 2851 | | | | | | |
| uc003mbg.1 | 170746724 | 170770493 | 23769 | | | | | | |
| uc003mbh.1 | 170747402 | 170770493 | 18936 uc003mbh.1 | NPM1 | b5 | 2 | 6 | 1 | 1 |
| uc003mbi.1 | 170747402 | 170770493 | 23091 | | | | | | |
| uc003mbj.1 | 170747402 | 170770493 | 23091 | | | | | | |
| uc003mbk.1 | 170779271 | 170816769 | 37498 | | | | | | |
| uc003mbl.1 | 171221160 | 171366482 | 145322 | | | | | | |
| uc003mbm.1 | 171221160 | 171366482 | 145322 | | | | | | |
| uc003mbn.1 | 171221160 | 171366482 | 145322 | | | | | | |
| uc003mbo.1 | 171401678 | 171547951 | 146273 | | | | | | |
| uc003mbp.1 | 171569254 | 171643400 | 74146 | | | | | | |
| uc003mbq.1 | 171645281 | 171657985 | 12704 | | | | | | |
| uc003mbr.1 | 171693107 | 171814132 | 121025 | | | | | | |
| uc003mbs.1 | 171740669 | 171814132 | 73463 | | | | | | |

Fig. 23

Chromosome position represented
chr15:85,220,992-87,600,665
Total number of genes  16

| #name | txStart | txEnd | | size | fusion gene name | Rank size order | Comparative genomics peak order | standard | actual | gene size |
|---|---|---|---|---|---|---|---|---|---|---|
| uc002blz.1 | 84486245 | 85373287 | | 887042 | | | | | | |
| uc002bmc.1 | 85921163 | 85923921 | | 2758 | | | | | | |
| uc002bmd.1 | 86203985 | 86206591 | | 2606 | | | | | | |
| uc002bme.1 | 86220991 | 86600665 | uc002bme.1 | 379674 | NTRK3 | 1 | 1 | 13 | 0 | 7 |
| uc002bmf.1 | 86220991 | 86600665 | | 379674 | | | | | | |
| uc002bmg.1 | 86321598 | 86600665 | | 279067 | | | | | | |
| uc002bmh.1 | 86471396 | 86479632 | | 8236 | | | | | | |
| uc002bmi.1 | 86803711 | 86810008 | | 6297 | | | | | | |
| uc002bmj.1 | 86803713 | 86811623 | | 7910 | | | | | | |
| uc002bmk.1 | 86803713 | 86811623 | | 7910 | | | | | | |
| uc002bml.1 | 86811687 | 86822499 | | 10812 | | | | | | |
| uc002bmm.1 | 86811687 | 86822499 | | 10812 | | | | | | |
| uc002bmn.1 | 86811687 | 86822499 | | 10812 | | | | | | |
| uc002bmo.1 | 86846152 | 86849568 | | 3416 | | | | | | |
| uc002bmp.1 | 86855789 | 86890888 | | 35099 | | | | | | |
| uc002bmq.1 | 86856585 | 86890888 | | 34303 | | | | | | |
| uc002bmr.1 | 86856585 | 86890888 | | 34303 | | | | | | |
| uc002bms.1 | 86929805 | 86948838 | | 19033 | | | | | | |
| uc002bmt.1 | 86965592 | 86976516 | | 10924 | | | | | | |
| uc002bmu.1 | 86979907 | 86999883 | | 19976 | | | | | | |
| uc002bmv.1 | 86983042 | 86999883 | | 16841 | | | | | | |
| uc002bmw.1 | 86983042 | 86999883 | | 16841 | | | | | | |
| uc002bmx.1 | 87147677 | 87195759 | | 48082 | | | | | | |
| uc002bmy.1 | 87147677 | 87219589 | | 71912 | | | | | | |
| uc002bmz.1 | 87147677 | 87219589 | | 71912 | | | | | | |
| uc002bna.1 | 87200759 | 87219589 | | 18830 | | | | | | |
| uc002bnb.1 | 87212450 | 87212564 | | 114 | | | | | | |
| uc002bnc.1 | 87221522 | 87239774 | | 18252 | | | | | | |
| uc002bnd.1 | 87221522 | 87239774 | | 18252 | | | | | | |

Fig. 24a

| #name | txStart | txEnd | size | fusion gene name | Rank size order | Comparative genomics peak order | standard | actual | gene size |
|---|---|---|---|---|---|---|---|---|---|
| uc002bne.1 | 87221522 | 87239774 | 18252 | | | | | | |
| uc002bnf.1 | 87242919 | 87256759 | 13840 | | | | | | |
| uc002bng.1 | 87242919 | 87257614 | 14695 | | | | | | |
| uc002bnh.1 | 87242919 | 87257614 | 14695 | | | | | | |
| uc002bni.1 | 87242949 | 87257614 | 14665 | | | | | | |
| uc002bnj.1 | 87432428 | 87546591 | 114163 | | | | | | |
| uc002bnk.1 | 87432428 | 87546591 | 114163 | | | | | | |
| uc002bnl.1 | 87554101 | 87565926 | 11825 | | | | | | |
| uc002bnm.1 | 87588197 | 87661366 | 73169 | | | | | | |
| uc002bnn.1 | 87588197 | 87661366 | 73169 | | | | | | |
| uc002bno.1 | 87588251 | 87608881 | 20630 | | | | | | |

Fig. 24b

Chromosome position represented
chr11:2,652,816-4,775,468
Total number of genes 36

| #name | txStart | txEnd | size | fusion gene name | Rank size order | Comparative genomics peak order | standard | actual | gene size |
|---|---|---|---|---|---|---|---|---|---|
| uc001lwn.1 | 2422796 | 2826916 | 404120 | | | | | | |
| uc001lwo.1 | 2439259 | 2826916 | 387657 | | | | | | |
| uc001lwp.1 | 2674976 | 2675568 | 592 | | | | | | |
| uc001lwq.1 | 2847838 | 2849911 | 2073 | | | | | | |
| uc001lwr.1 | 2861387 | 2863537 | 2150 | | | | | | |
| uc001lws.1 | 2861440 | 2863537 | 2097 | | | | | | |
| uc001lwt.1 | 2861440 | 2863571 | 2131 | | | | | | |
| uc001lwu.1 | 2862533 | 2863571 | 1038 | | | | | | |
| uc001lwv.1 | 2865903 | 2881546 | 15643 | | | | | | |
| uc001lww.1 | 2865903 | 2881546 | 15643 | | | | | | |
| uc001lwx.1 | 2877526 | 2903052 | 25526 | | | | | | |
| uc001lwy.1 | 2880099 | 2903052 | 22953 | | | | | | |
| uc001lwz.1 | 2880099 | 2903052 | 22953 | | | | | | |
| uc001lxa.1 | 2906078 | 2907226 | 1148 | | | | | | |
| uc001lxb.1 | 2922235 | 2930575 | 8340 | | | | | | |
| uc001lxc.1 | 2922235 | 2970183 | 47948 | | | | | | |
| uc001lxd.1 | 2941576 | 2941699 | 123 | | | | | | |
| uc001lxe.1 | 2978734 | 3035247 | 56513 | | | | | | |
| uc001lxf.1 | 2978734 | 3035247 | 56513 | | | | | | |
| uc001lxg.1 | 2978734 | 3035247 | 56513 | | | | | | |
| uc001lxh.1 | 2978734 | 3035247 | 56513 | | | | | | |
| uc001lxi.1 | 3007199 | 3019066 | 11867 | | | | | | |
| uc001lxj.1 | 3065606 | 3072685 | 7079 | | | | | | |
| uc001lxk.1 | 3065606 | 3143116 | 77510 | | | | | | |
| uc001lxl.1 | 3065606 | 3143116 | 77510 | | | | | | |
| uc001lxm.1 | 3104278 | 3107066 | 2788 | | | | | | |
| uc001lxn.1 | 3196193 | 3200932 | 4739 | | | | | | |
| uc001lxo.1 | 3196193 | 3200932 | 4739 | | | | | | |
| uc001lxp.1 | 3196457 | 3196619 | 162 | | | | | | |

Fig. 25a

| #name | txStart | txEnd | size | fusion gene name | Rank size order | Comparative genomics peak order | standard | actual | gene size |
|---|---|---|---|---|---|---|---|---|---|
| uc001lxq.1 | 3205616 | 3206636 | 1020 | | | | | | |
| uc001lxr.1 | 3335731 | 3336576 | 845 | | | | | | |
| uc001lxs.1 | 3336574 | 3356991 | 20417 | | | | | | |
| uc001lxt.1 | 3336574 | 3356991 | 20417 | | | | | | |
| uc001lxu.1 | 3336574 | 3356991 | 20417 | | | | | | |
| uc001lxv.1 | 3336574 | 3356991 | 20417 | | | | | | |
| uc001lxw.1 | 3358776 | 3375878 | 17102 | | | | | | |
| uc001lxx.1 | 3358776 | 3386784 | 28008 | | | | | | |
| uc001lxy.1 | 3358776 | 3386784 | 28008 | | | | | | |
| uc001lxz.1 | 3595037 | 3604325 | 9288 | | | | | | |
| uc001lya.1 | 3604289 | 3615365 | 11076 | | | | | | |
| uc001lyb.1 | 3616311 | 3620061 | 3750 | | | | | | |
| uc001lyc.1 | 3616311 | 3620122 | 3811 | | | | | | |
| uc001lyd.1 | 3616317 | 3620061 | 3744 | | | | | | |
| uc001lye.1 | 3622936 | 3642222 | 19286 | | | | | | |
| uc001lyf.1 | 3643392 | 3649190 | 5798 | | | | | | |
| uc001lyg.1 | 3652815 | 3684433 | 31618 | | | | | | |
| uc001lyh.1 | 3652815 | 3775468 | 122653 | | | | | | |
| uc001lyi.1 | 3652815 | 3775468 uc001lyi.1 | 122653 | NUP98 | 3 | 1 | 8 | 1 | 2 |
| uc001lyj.1 | 3689634 | 3775468 | 85834 | | | | | | |
| uc001lyk.1 | 3689634 | 3775468 | 85834 | | | | | | |
| uc001lyl.1 | 3775529 | 3804160 | 28631 | | | | | | |
| uc001lym.1 | 3775718 | 3804160 | 28442 | | | | | | |
| uc001lyn.1 | 3775718 | 3804160 | 28442 | | | | | | |
| uc001lyo.1 | 3775718 | 3804160 | 28442 | | | | | | |
| uc001lyp.1 | 3775718 | 3804160 | 28442 | | | | | | |
| uc001lyq.1 | 3775718 | 3804160 | 28442 | | | | | | |
| uc001lyr.1 | 3785847 | 3804160 | 18313 | | | | | | |
| uc001lys.1 | 3786359 | 3804160 | 17801 | | | | | | |
| uc001lyt.1 | 3786359 | 3804160 | 17801 | | | | | | |
| uc001lyu.1 | 3804787 | 3818760 | 13973 | | | | | | |
| uc001lyv.1 | 3833508 | 4071015 | 237507 | | | | | | |
| uc001lyw.1 | 4072586 | 4116682 | 44096 | | | | | | |

Fig. 25b

| #name | txStart | txEnd | size | fusion gene name | Rank size order | Comparative genomics peak order | standard | actual | gene size |
|---|---|---|---|---|---|---|---|---|---|
| uc001lyx.1 | 4345156 | 4346101 | 945 | | | | | | |
| uc001lyy.1 | 4362702 | 4371502 | 8800 | | | | | | |
| uc001lyz.1 | 4427145 | 4428090 | 945 | | | | | | |
| uc001lza.1 | 4466706 | 4467651 | 945 | | | | | | |
| uc001lzb.1 | 4522996 | 4523950 | 954 | | | | | | |
| uc001lzc.1 | 4549228 | 4555626 | 6398 | | | | | | |
| uc001lzd.1 | 4564618 | 4565671 | 1053 | | | | | | |
| uc001lze.1 | 4571844 | 4572819 | 975 | | | | | | |
| uc001lzf.1 | 4576477 | 4586013 | 9536 | | | | | | |
| uc001lzg.1 | 4576477 | 4586013 | 9536 | | | | | | |
| uc001lzh.1 | 4617596 | 4618571 | 975 | | | | | | |
| uc001lzi.1 | 4621731 | 4633288 | 11557 | | | | | | |
| uc001lzj.1 | 4630135 | 4631485 | 1350 | | | | | | |
| uc001lzk.1 | 4657976 | 4675645 | 17669 | | | | | | |
| uc001lzl.1 | 4746784 | 4747723 | 939 | | | | | | |

Fig. 25c

Chromosome position represented
chr2:221,772,851-223,871,944
Total number of genes 8

| #name | txStart | txEnd | size | fusion gene name | Rank size order | Comparative genomics peak order | standard | actual | gene size |
|---|---|---|---|---|---|---|---|---|---|
| uc002vmq.1 | 221990990 | 222145254 | 154264 | | | | | | |
| uc002vmr.1 | 221998172 | 222145254 | 147082 | | | | | | |
| uc002vms.1 | 222145469 | 222147418 | 1949 | | | | | | |
| uc002vmt.1 | 222772850 | 222871944 | 99094 | | | | | | |
| uc002vmu.1 | 222772850 | 222871944 | 99094 | | | | | | |
| uc002vmv.1 | 222772850 | 222871944 | 99094 | | | | | | |
| uc002vmw.1 | 222772850 | 222871944 | 99094 | | | | | | |
| uc002vmx.1 | 222772850 | 222871944 | 99094 | | | | | | |
| uc002vmy.1 | 222772850 | 222871944 uc002vmy.1 | 99094 | PAX3 | 3 | 3 | 8 | 0 | 2 |
| uc002vmz.1 | 222866592 | 222871944 | 5352 | | | | | | |
| uc002vna.1 | 222866592 | 222871944 | 5352 | | | | | | |
| uc002vnb.1 | 222871109 | 222878180 | 7071 | | | | | | |
| uc002vnc.1 | 222893656 | 222894685 | 1029 | | | | | | |
| uc002vnd.1 | 222997565 | 223131861 | 134296 | | | | | | |
| uc002vne.1 | 223144405 | 223229071 | 84666 | | | | | | |
| uc002vnf.1 | 223144405 | 223229071 | 84666 | | | | | | |
| uc002vng.1 | 223218591 | 223229071 | 10480 | | | | | | |
| uc002vnh.1 | 223244700 | 223282893 | 38193 | | | | | | |
| uc002vni.1 | 223433975 | 223516363 | 82388 | | | | | | |
| uc002vnj.1 | 223433975 | 223516363 | 82388 | | | | | | |
| uc002vnk.1 | 223515903 | 223517600 | 1697 | | | | | | |
| uc002vnl.1 | 223625170 | 223626873 | 1703 | | | | | | |

Fig. 26

Chromosome position represented
chr1:17,830,087-19,935,219
Total number of genes 20

| #name | txStart | txEnd | size | | fusion gene name | Rank size order | Comparative genomics peak order | standard | actual | gene size |
|---|---|---|---|---|---|---|---|---|---|---|
| uc001ban.1 | 17738916 | 17896957 | 158041 | | | | | | | |
| uc001bao.1 | 17779634 | 17896957 | 117323 | | | | | | | |
| uc001bap.1 | 17779634 | 17896957 | 117323 | | | | | | | |
| uc001baq.1 | 17814169 | 17896957 | 82788 | | | | | | | |
| uc001bar.1 | 17817397 | 17896957 | 79560 | | | | | | | |
| uc001bas.1 | 17893128 | 17896957 | 3829 | | | | | | | |
| uc001bat.1 | 17954430 | 18026145 | 71715 | | | | | | | |
| uc001bau.1 | 18306826 | 18577563 | 270737 | | | | | | | |
| uc001bav.1 | 18560447 | 18577563 | 17116 | | | | | | | |
| uc001baw.1 | 18573650 | 18574761 | 1111 | | | | | | | |
| uc001bax.1 | 18680010 | 18685067 | 5057 | | | | | | | |
| uc001bay.1 | 18830086 | 18935219 | 105133 | | | | | | | |
| uc001baz.1 | 18830086 | 18935219 | 105133 | uc001baz.1 | PAX7 | 6 (b5) | 1 | 8 | 0 | 2 |
| uc001bba.1 | 19038679 | 19058742 | 20063 | | | | | | | |
| uc001bbb.1 | 19070512 | 19101659 | 31147 | | | | | | | |
| uc001bbc.1 | 19070512 | 19101659 | 31147 | | | | | | | |
| uc001bbd.1 | 19103361 | 19116108 | 12747 | | | | | | | |
| uc001bbe.1 | 19271190 | 19274592 | 3402 | | | | | | | |
| uc001bbf.1 | 19273586 | 19280727 | 7141 | | | | | | | |
| uc001bbg.1 | 19273586 | 19303997 | 30411 | | | | | | | |
| uc001bbh.1 | 19273586 | 19304923 | 31337 | | | | | | | |
| uc001bbi.1 | 19273586 | 19409333 | 135747 | | | | | | | |
| uc001bbj.1 | 19310720 | 19317061 | 6341 | | | | | | | |
| uc001bbk.1 | 19320269 | 19350940 | 30671 | | | | | | | |
| uc001bbl.1 | 19350004 | 19356006 | 6002 | | | | | | | |
| uc001bbm.1 | 19350004 | 19378301 | 28297 | | | | | | | |
| uc001bbn.1 | 19417170 | 19420997 | 3827 | | | | | | | |
| uc001bbo.1 | 19417170 | 19450633 | 33463 | | | | | | | |
| uc001bbp.1 | 19417170 | 19450633 | 33463 | | | | | | | |

Fig. 27a

| #name | txStart | txEnd | size | fusion gene name | Rank size order | Comparative genomics peak order | standard | actual | gene size |
|---|---|---|---|---|---|---|---|---|---|
| uc001bbq.1 | 19417170 | 19450633 | 33463 | | | | | | |
| uc001bbr.1 | 19417170 | 19450633 | 33463 | | | | | | |
| uc001bbs.1 | 19450661 | 19459209 | 8548 | | | | | | |
| uc001bbt.1 | 19465062 | 19470016 | 4954 | | | | | | |
| uc001bbu.1 | 19465062 | 19473022 | 7960 | | | | | | |
| uc001bbv.1 | 19481643 | 19487867 | 6224 | | | | | | |
| uc001bbw.1 | 19503048 | 19511227 | 8179 | | | | | | |
| uc001bbx.1 | 19503048 | 19511227 | 8179 | | | | | | |
| uc001bby.1 | 19511326 | 19528381 | 17055 | | | | | | |
| uc001bbz.1 | 19511326 | 19528381 | 17055 | | | | | | |
| uc001bca.1 | 19511326 | 19528381 | 17055 | | | | | | |
| uc001bcb.1 | 19511326 | 19528381 | 17055 | | | | | | |
| uc001bcc.1 | 19511809 | 19528381 | 16572 | | | | | | |
| uc001bcd.1 | 19537859 | 19618840 | 80981 | | | | | | |
| uc001bce.1 | 19537859 | 19684579 | 146720 | | | | | | |
| uc001bcf.1 | 19545921 | 19548014 | 2093 | | | | | | |
| uc001bcg.1 | 19597959 | 19600295 | 2336 | | | | | | |
| uc001bch.1 | 19796053 | 19827391 | 31338 | | | | | | |
| uc001bci.1 | 19796053 | 19827761 | 31708 | | | | | | |
| uc001bcj.1 | 19842312 | 19857532 | 15220 | | | | | | |
| uc001bck.1 | 19843394 | 19857532 | 14138 | | | | | | |
| uc001bcl.1 | 19864366 | 19878642 | 14276 | | | | | | |
| uc001bcm.1 | 19881319 | 19979846 | 98527 | | | | | | |
| uc001bcn.1 | 19881319 | 19998997 | 117678 | | | | | | |
| uc001bco.1 | 19881321 | 19998424 | 117103 | | | | | | |
| uc001bcp.1 | 19881321 | 19998424 | 117103 | | | | | | |

Fig. 27b

Chromosome position represented
chr2:112,690,045-114,752,968
Total number of genes  34

| #name | txStart | txEnd | size | fusion gene name | Rank size order | Comparative genomics peak order | standard | actual | gene size |
|---|---|---|---|---|---|---|---|---|---|
| uc002thp.1 | 112689910 | 112729121 | 39211 | | | | | | |
| uc002thq.1 | 112749648 | 112814111 | 64463 | | | | | | |
| uc002thr.1 | 112773896 | 112779801 | 5905 | | | | | | |
| uc002ths.1 | 112842436 | 112907578 | 65142 | | | | | | |
| uc002tht.1 | 112862071 | 112896160 | 34089 | | | | | | |
| uc002thu.1 | 112956213 | 113006693 | 50480 | | | | | | |
| uc002thv.1 | 112997160 | 113006453 | 9293 | | | | | | |
| uc002thw.1 | 113016083 | 113051879 | 35796 | | | | | | |
| uc002thx.1 | 113016083 | 113051879 | 35796 | | | | | | |
| uc002thy.1 | 113016083 | 113051879 | 35796 | | | | | | |
| uc002thz.1 | 113058506 | 113063088 | 4582 | | | | | | |
| uc002tia.1 | 113058506 | 113063322 | 4816 | | | | | | |
| uc002tib.1 | 113119997 | 113137871 | 17874 | | | | | | |
| uc002tic.1 | 113130435 | 113134620 | 4185 | | | | | | |
| uc002tid.1 | 113195533 | 113216925 | 21392 | | | | | | |
| uc002tie.1 | 113211916 | 113238657 | 26741 | | | | | | |
| uc002tif.1 | 113211916 | 113238657 | 26741 | | | | | | |
| uc002tig.1 | 113247962 | 113259442 | 11480 | | | | | | |
| uc002tih.1 | 113303807 | 113309674 | 5867 | | | | | | |
| uc002tii.1 | 113303807 | 113310827 | 7020 | | | | | | |
| uc002tij.1 | 113387018 | 113392929 | 5911 | | | | | | |
| uc002tik.1 | 113387018 | 113392929 | 5911 | | | | | | |
| uc002til.1 | 113387018 | 113392929 | 5911 | | | | | | |
| uc002tim.1 | 113387018 | 113392929 | 5911 | | | | | | |
| uc002tin.1 | 113389240 | 113392929 | 3689 | | | | | | |
| uc002tio.1 | 113452076 | 113459698 | 7622 | | | | | | |
| uc002tip.1 | 113479919 | 113482092 | 2173 | | | | | | |
| uc002tiq.1 | 113496138 | 113526911 | 30773 | | | | | | |
| uc002tir.1 | 113501606 | 113526911 | 25305 | | | | | | |

Fig. 28a

| #name | txStart | txEnd | size | fusion gene name | Rank size order | Comparative genomics peak order | standard | actual | gene size |
|---|---|---|---|---|---|---|---|---|---|
| uc002tis.1 | 113532685 | 113538791 | 6106 | | | | | | |
| uc002tit.1 | 113533155 | 113538791 | 5636 | | | | | | |
| uc002tiu.1 | 113542017 | 113549898 | 7881 | | | | | | |
| uc002tiv.1 | 113546365 | 113549898 | 3533 | | | | | | |
| uc002tiw.1 | 113548586 | 113549898 | 1312 | | | | | | |
| uc002tix.1 | 113573407 | 113608061 | 34654 | | | | | | |
| uc002tiy.1 | 113591940 | 113608064 | 16124 | | | | | | |
| uc002tiz.1 | 113591940 | 113608064 | 16124 | | | | | | |
| uc002tja.1 | 113591940 | 113608064 | 16124 | | | | | | |
| uc002tjb.1 | 113601608 | 113608064 | 6456 | | | | | | |
| uc002tjc.1 | 113648030 | 113677148 | 29118 | | | | | | |
| uc002tjd.1 | 113648030 | 113677148 | 29118 | | | | | | |
| uc002tje.1 | 113648030 | 113677148 | 29118 | | | | | | |
| uc002tjf.1 | 113659004 | 113677148 | 18144 | | | | | | |
| uc002tjg.1 | 113671242 | 113677148 | 5906 | | | | | | |
| uc002tjh.1 | 113672605 | 113677148 | 4543 | | | | | | |
| uc002tji.1 | 113679973 | 113683444 | 3471 | | | | | | |
| uc002tjj.1 | 113690044 | 113752968 | 62924 | | | | | | |
| uc002tjk.1 | 113690044 | 113752968 | 62924 | | | | | | |
| uc002tjl.1 | 113690044 | 113752968 | 62924 | | | | | | |
| uc002tjm.1 | 113690044 | 113752968 | 62924 | | | | | | |
| uc002tjn.1 | 113690044 | 113752968 uc002tjn.1 | 62924 | PAX8 | 4 | b7 (8 or 9) | 8 | NA | 2 |
| uc002tjo.1 | 113699644 | 113711555 | 11911 | | | | | | |
| uc002tjp.1 | 113709583 | 113714872 | 5289 | | | | | | |
| uc002tjq.1 | 113709583 | 113741057 | 31474 | | | | | | |
| uc002tjr.1 | 113710316 | 113741057 | 30741 | | | | | | |
| uc002tjs.1 | 113724813 | 113741057 | 16244 | | | | | | |
| uc002tjt.1 | 113911852 | 113918064 | 6212 | | | | | | |
| uc002tju.1 | 113911852 | 113970216 | 58364 | | | | | | |
| uc002tjv.1 | 113911852 | 113970216 | 58364 | | | | | | |
| uc002tjw.1 | 113973130 | 113975380 | 2250 | | | | | | |
| uc002tjx.1 | 114014103 | 114016712 | 2609 | | | | | | |
| uc002tjy.1 | 114037320 | 114037347 | 27 | | | | | | |

Fig. 28b

| #name | txStart | txEnd | size | fusion gene name | Rank size order | Comparative genomics peak order | standard | actual | gene size |
|---|---|---|---|---|---|---|---|---|---|
| uc002tjz.1 | 114051432 | 114052897 | 1465 | | | | | | |
| uc002tka.1 | 114057699 | 114072513 | 14814 | | | | | | |
| uc002tkb.1 | 114058111 | 114073083 | 14972 | | | | | | |
| uc002tkc.1 | 114062596 | 114070625 | 8029 | | | | | | |
| uc002tkd.1 | 114062596 | 114073083 | 10487 | | | | | | |
| uc002tke.1 | 114067712 | 114070625 | 2913 | | | | | | |
| uc002tkf.1 | 114069730 | 114070625 | 895 | | | | | | |
| uc002tkg.1 | 114070114 | 114071685 | 1571 | | | | | | |
| uc002tkh.1 | 114070114 | 114073083 | 2969 | | | | | | |
| uc002tki.1 | 114073075 | 114076255 | 3180 | | | | | | |
| uc002tkj.1 | 114073075 | 114077764 | 4689 | | | | | | |
| uc002tkk.1 | 114085514 | 114101133 | 15619 | | | | | | |
| uc002tkl.1 | 114101353 | 114116517 | 15164 | | | | | | |
| uc002tkm.1 | 114101353 | 114116517 | 15164 | | | | | | |
| uc002tkn.1 | 114101353 | 114117436 | 16083 | | | | | | |
| uc002tko.1 | 114101353 | 114117436 | 16083 | | | | | | |
| uc002tkp.1 | 114101353 | 114117436 | 16083 | | | | | | |
| uc002tkq.1 | 114102600 | 114107940 | 5340 | | | | | | |
| uc002tkr.1 | 114102600 | 114116192 | 13592 | | | | | | |
| uc002tks.1 | 114102600 | 114116517 | 13917 | | | | | | |
| uc002tkt.1 | 114188399 | 114230740 | 42341 | | | | | | |
| uc002tku.1 | 114188402 | 114230870 | 42468 | | | | | | |
| uc002tkv.1 | 114215930 | 114230740 | 14810 | | | | | | |
| uc002tkw.1 | 114215930 | 114230870 | 14940 | | | | | | |
| uc002tkx.1 | 114364006 | 114432637 | 68631 | | | | | | |
| uc002tky.1 | 114453615 | 114457305 | 3690 | | | | | | |
| uc002tkz.1 | 114453615 | 114481349 | 27734 | | | | | | |

Fig. 28c

Chromosome position represented
chr2:112,690,045-114,752,968
Total number of genes  34

| #name | txStart | txEnd | size | fusion gene name | Rank size order | Comparative genomics peak order | standard | actual | gene size |
|---|---|---|---|---|---|---|---|---|---|
| uc002thp.1 | 112689910 | 112729121 | 39211 | | | | | | |
| uc002thq.1 | 112749648 | 112814111 | 64463 | | | | | | |
| uc002thr.1 | 112773896 | 112779801 | 5905 | | | | | | |
| uc002ths.1 | 112842436 | 112907578 | 65142 | | | | | | |
| uc002tht.1 | 112862071 | 112896160 | 34089 | | | | | | |
| uc002thu.1 | 112956213 | 113006693 | 50480 | | | | | | |
| uc002thv.1 | 112997160 | 113006453 | 9293 | | | | | | |
| uc002thw.1 | 113016083 | 113051879 | 35796 | | | | | | |
| uc002thx.1 | 113016083 | 113051879 | 35796 | | | | | | |
| uc002thy.1 | 113016083 | 113051879 | 35796 | | | | | | |
| uc002thz.1 | 113058506 | 113063088 | 4582 | | | | | | |
| uc002tia.1 | 113058506 | 113063322 | 4816 | | | | | | |
| uc002tib.1 | 113119997 | 113137871 | 17874 | | | | | | |
| uc002tic.1 | 113130435 | 113134620 | 4185 | | | | | | |
| uc002tid.1 | 113195533 | 113216925 | 21392 | | | | | | |
| uc002tie.1 | 113211916 | 113238657 | 26741 | | | | | | |
| uc002tif.1 | 113211916 | 113238657 | 26741 | | | | | | |
| uc002tig.1 | 113247962 | 113259442 | 11480 | | | | | | |
| uc002tih.1 | 113303807 | 113309674 | 5867 | | | | | | |
| uc002tii.1 | 113303807 | 113310827 | 7020 | | | | | | |
| uc002tij.1 | 113387018 | 113392929 | 5911 | | | | | | |
| uc002tik.1 | 113387018 | 113392929 | 5911 | | | | | | |
| uc002til.1 | 113387018 | 113392929 | 5911 | | | | | | |
| uc002tim.1 | 113387018 | 113392929 | 5911 | | | | | | |
| uc002tin.1 | 113389240 | 113392929 | 3689 | | | | | | |
| uc002tio.1 | 113452076 | 113459698 | 7622 | | | | | | |
| uc002tip.1 | 113479919 | 113482092 | 2173 | | | | | | |
| uc002tiq.1 | 113496138 | 113526911 | 30773 | | | | | | |
| uc002tir.1 | 113501606 | 113526911 | 25305 | | | | | | |

Fig. 29a

| #name | txStart | txEnd | size | fusion gene name | Rank size order | Comparative genomics peak order | standard | actual | gene size |
|---|---|---|---|---|---|---|---|---|---|
| uc002tis.1 | 113532685 | 113538791 | 6106 | | | | | | |
| uc002tit.1 | 113533155 | 113538791 | 5636 | | | | | | |
| uc002tiu.1 | 113542017 | 113549898 | 7881 | | | | | | |
| uc002tiv.1 | 113546365 | 113549898 | 3533 | | | | | | |
| uc002tiw.1 | 113548586 | 113549898 | 1312 | | | | | | |
| uc002tix.1 | 113573407 | 113608061 | 34654 | | | | | | |
| uc002tiy.1 | 135591940 | 113608064 | 16124 | | | | | | |
| uc002tiz.1 | 135591940 | 113608064 | 16124 | | | | | | |
| uc002tja.1 | 135591940 | 113608064 | 16124 | | | | | | |
| uc002tjb.1 | 136601608 | 113608064 | 6456 | | | | | | |
| uc002tjc.1 | 136648030 | 113677148 | 29118 | | | | | | |
| uc002tjd.1 | 136648030 | 113677148 | 29118 | | | | | | |
| uc002tje.1 | 136648030 | 113677148 | 29118 | | | | | | |
| uc002tjf.1 | 136659004 | 113677148 | 18144 | | | | | | |
| uc002tjg.1 | 136671242 | 113677148 | 5906 | | | | | | |
| uc002tjh.1 | 136672605 | 113677148 | 4543 | | | | | | |
| uc002tji.1 | 136679973 | 113683444 | 3471 | | | | | | |
| uc002tjj.1 | 136690044 | 113752968 | 62924 | | | | | | |
| uc002tjk.1 | 136690044 | 113752968 | 62924 | | | | | | |
| uc002tjl.1 | 136690044 | 113752968 | 62924 | | | | | | |
| uc002tjm.1 | 136690044 | 113752968 | 62924 | | | | | | |
| uc002tjn.1 uc002tjn.1 | 136690044 | 113752968 | 62924 | PAX8 | 4 | b7 (8 or 9) | 8 | NA | 2 |
| uc002tjo.1 | 136699644 | 113711555 | 11911 | | | | | | |
| uc002tjp.1 | 137709583 | 113714872 | 5289 | | | | | | |
| uc002tjq.1 | 137709583 | 113741057 | 31474 | | | | | | |
| uc002tjr.1 | 137710316 | 113741057 | 30741 | | | | | | |
| uc002tjs.1 | 137724813 | 113741057 | 16244 | | | | | | |
| uc002tjt.1 | 139911852 | 113918064 | 6212 | | | | | | |
| uc002tju.1 | 139911852 | 113970216 | 58364 | | | | | | |
| uc002tjv.1 | 139911852 | 113970216 | 58364 | | | | | | |
| uc002tjw.1 | 139973130 | 113975380 | 2250 | | | | | | |
| uc002tjx.1 | 140014103 | 114016712 | 2609 | | | | | | |
| uc002tjy.1 | 140037320 | 114037347 | 27 | | | | | | |

Fig. 29b

| #name | txStart | txEnd | size | fusion gene name | Rank size order | Comparative genomics peak order | standard | actual | gene size |
|---|---|---|---|---|---|---|---|---|---|
| uc002tjz.1 | 114051432 | 114052897 | 1465 | | | | | | |
| uc002tka.1 | 114057699 | 114072513 | 14814 | | | | | | |
| uc002tkb.1 | 114058111 | 114073083 | 14972 | | | | | | |
| uc002tkc.1 | 114062596 | 114070625 | 8029 | | | | | | |
| uc002tkd.1 | 114062596 | 114073083 | 10487 | | | | | | |
| uc002tke.1 | 114067712 | 114070625 | 2913 | | | | | | |
| uc002tkf.1 | 114069730 | 114070625 | 895 | | | | | | |
| uc002tkg.1 | 114070114 | 114071685 | 1571 | | | | | | |
| uc002tkh.1 | 114070114 | 114073083 | 2969 | | | | | | |
| uc002tki.1 | 114073075 | 114076255 | 3180 | | | | | | |
| uc002tkj.1 | 114073075 | 114077764 | 4689 | | | | | | |
| uc002tkk.1 | 114085514 | 114101133 | 15619 | | | | | | |
| uc002tkl.1 | 114101353 | 114116517 | 15164 | | | | | | |
| uc002tkm.1 | 114101353 | 114116517 | 15164 | | | | | | |
| uc002tkn.1 | 114101353 | 114117436 | 16083 | | | | | | |
| uc002tko.1 | 114101353 | 114117436 | 16083 | | | | | | |
| uc002tkp.1 | 114101353 | 114117436 | 16083 | | | | | | |
| uc002tkq.1 | 114102600 | 114107940 | 5340 | | | | | | |
| uc002tkr.1 | 114102600 | 114116192 | 13592 | | | | | | |
| uc002tks.1 | 114102600 | 114116517 | 13917 | | | | | | |
| uc002tkt.1 | 114188399 | 114230740 | 42341 | | | | | | |
| uc002tku.1 | 114188402 | 114230870 | 42468 | | | | | | |
| uc002tkv.1 | 114215930 | 114230740 | 14810 | | | | | | |
| uc002tkw.1 | 114215930 | 114230870 | 14940 | | | | | | |
| uc002tkx.1 | 114364006 | 114432637 | 68631 | | | | | | |
| uc002tky.1 | 114453615 | 114457305 | 3690 | | | | | | |
| uc002tkz.1 | 114453615 | 114481349 | 27734 | | | | | | |

Fig. 29c

Chromosome position represented
chr15:71,074,067-73,127,208
Total number of genes 40

| #name | txStart | txEnd | size | fusion gene name | Rank size order | Comparative genomics peak order | standard | actual | gene size |
|---|---|---|---|---|---|---|---|---|---|
| uc002avm.1 | 71131927 | 71382837 | 250910 | | | | | | |
| uc002avn.1 | 71215284 | 71382837 | 167553 | | | | | | |
| uc002avo.1 | 71382904 | 71384598 | 1694 | | | | | | |
| uc002avp.1 | 71400987 | 71448230 | 47243 | | | | | | |
| uc002avq.1 | 71522551 | 71639406 | 116855 | | | | | | |
| uc002avr.1 | 71639409 | 71649817 | 10408 | | | | | | |
| uc002avs.1 | 71639409 | 71712806 | 73397 | | | | | | |
| uc002avt.1 | 71639409 | 71712806 | 73397 | | | | | | |
| uc002avu.1 | 71763674 | 71791548 | 27874 | | | | | | |
| uc002avv.1 | 71763674 | 71793912 | 30238 | | | | | | |
| uc002avw.1 | 71763674 | 71793912 | 30238 | | | | | | |
| uc002avx.1 | 71783569 | 71793905 | 10336 | | | | | | |
| uc002avy.1 | 71819193 | 71830869 | 11676 | | | | | | |
| uc002avz.1 | 71953020 | 71968608 | 15588 | | | | | | |
| uc002awa.1 | 71996989 | 72007180 | 10191 | | | | | | |
| uc002awb.1 | 71996989 | 72007642 | 10653 | | | | | | |
| uc002awc.1 | 72005841 | 72031531 | 25690 | | | | | | |
| uc002awd.1 | 72027188 | 72031531 | 4343 | | | | | | |
| uc002awe.1 | 72062612 | 72071688 | 9076 | | | | | | |
| uc002awf.1 | 72062612 | 72071688 | 9076 | | | | | | |
| uc002awg.1 | 72062612 | 72071688 | 9076 | | | | | | |
| uc002awh.1 | 72062612 | 72071688 | 9076 | | | | | | |
| uc002awi.1 | 72062612 | 72074002 | 11390 | | | | | | |
| uc002awj.1 | 72074066 | 72115787 | 41721 | | | | | | |
| uc002awk.1 | 72074066 | 72115788 | 41722 | | | | | | |
| uc002awl.1 | 72074066 | 72115788 | 41722 | | | | | | |
| uc002awm.1 | 72074066 | 72115788 | 41722 | | | | | | |
| uc002awn.1 | 72074066 | 72115788 | 41722 | | | | | | |
| uc002awo.1 | 72074066 | 72115788 | 41722 | | | | | | |

Fig. 30a

| #name | txStart | txEnd | size | fusion gene name | Rank size order | Comparative genomics peak order | standard | actual | gene size |
|---|---|---|---|---|---|---|---|---|---|
| uc002awp.1 | 72074066 | 72115788 | 41722 | | | | | | |
| uc002awq.1 | 72074066 | 72122770 | 48704 | | | | | | |
| uc002awr.1 | 72074066 | 72122770 | 48704 | | | | | | |
| uc002aws.1 | 72074066 | 72122770 | 48704 | | | | | | |
| uc002awt.1 | 72074066 | 72122770 | 48704 | | | | | | |
| uc002awu.1 | 72074066 | 72127208 uc002awu.1 | 53142 | PML | 6(b5) | 5 | 7 | 2 | 1 |
| uc002awv.1 | 72074066 | 72127208 | 53142 | | | | | | |
| uc002aww.1 | 72077397 | 72107836 | 30439 | | | | | | |
| uc002awx.1 | 72102221 | 72115788 | 13567 | | | | | | |
| uc002awy.1 | 72104250 | 72115788 | 11538 | | | | | | |
| uc002awz.1 | 72145257 | 72145296 | 39 | | | | | | |
| uc002axa.1 | 72149250 | 72161944 | 12694 | | | | | | |
| uc002axb.1 | 72152718 | 72152749 | 31 | | | | | | |
| uc002axc.1 | 72206301 | 72208569 | 2268 | | | | | | |
| uc002axd.1 | 72208751 | 72216196 | 7445 | | | | | | |
| uc002axe.1 | 72209052 | 72216196 | 7144 | | | | | | |
| uc002axf.1 | 72209947 | 72216196 | 6249 | | | | | | |
| uc002axg.1 | 72253139 | 72256265 | 3126 | | | | | | |
| uc002axh.1 | 72253957 | 72256265 | 2308 | | | | | | |
| uc002axi.1 | 72258860 | 72275683 | 16823 | | | | | | |
| uc002axj.1 | 72258860 | 72281919 | 23059 | | | | | | |
| uc002axk.1 | 72258860 | 72282245 | 23385 | | | | | | |
| uc002axl.1 | 72258860 | 72282609 | 23749 | | | | | | |
| uc002axm.1 | 72258860 | 72288372 | 29512 | | | | | | |
| uc002axn.1 | 72258860 | 72288372 | 29512 | | | | | | |
| uc002axo.1 | 72315719 | 72415535 | 99816 | | | | | | |
| uc002axp.1 | 72346071 | 72415866 | 69795 | | | | | | |
| uc002axq.1 | 72397952 | 72415535 | 17583 | | | | | | |
| uc002axr.1 | 72397952 | 72415535 | 17583 | | | | | | |
| uc002axs.1 | 72417156 | 72445600 | 28444 | | | | | | |
| uc002axt.1 | 72417156 | 72447020 | 29864 | | | | | | |
| uc002axu.1 | 72433849 | 72444014 | 10165 | | | | | | |
| uc002axv.1 | 72489375 | 72513329 | 23954 | | | | | | |

Fig. 30b

| #name | txStart | txEnd | size | fusion gene name | Rank size order | Comparative genomics peak order | standard | actual | gene size |
|---|---|---|---|---|---|---|---|---|---|
| uc002axw.1 | 72525370 | 72540563 | 15193 | | | | | | |
| uc002axx.1 | 72525370 | 72540563 | 15193 | | | | | | |
| uc002axy.1 | 72525370 | 72540582 | 15212 | | | | | | |
| uc002axz.1 | 72525370 | 72540582 | 15212 | | | | | | |
| uc002aya.1 | 72540658 | 72560661 | 20003 | | | | | | |
| uc002ayb.1 | 72540994 | 72560661 | 19667 | | | | | | |
| uc002ayc.1 | 72620600 | 72654396 | 33796 | | | | | | |
| uc002ayd.1 | 72620600 | 72677525 | 56925 | | | | | | |
| uc002aye.1 | 72620600 | 72677525 | 56925 | | | | | | |
| uc002ayf.1 | 72677895 | 72688119 | 10224 | | | | | | |
| uc002ayg.1 | 72687765 | 72709511 | 21746 | | | | | | |
| uc002ayh.1 | 72687765 | 72709511 | 21746 | | | | | | |
| uc002ayi.1 | 72694387 | 72709511 | 15124 | | | | | | |
| uc002ayj.1 | 72695298 | 72709511 | 14213 | | | | | | |
| uc002ayk.1 | 72698590 | 72709511 | 10921 | | | | | | |
| uc002ayl.1 | 72703013 | 72709511 | 6498 | | | | | | |
| uc002aym.1 | 72709951 | 72775413 | 65462 | | | | | | |
| uc002ayn.1 | 72709951 | 72775413 | 65462 | | | | | | |
| uc002ayo.1 | 72709951 | 72775413 | 65462 | | | | | | |
| uc002ayp.1 | 72798942 | 72804930 | 5988 | | | | | | |
| uc002ayq.1 | 72798942 | 72804930 | 5988 | | | | | | |
| uc002ayr.1 | 72828236 | 72835994 | 7758 | | | | | | |
| uc002ays.1 | 72861767 | 72882558 | 20791 | | | | | | |
| uc002ayt.1 | 72892246 | 72906261 | 14015 | | | | | | |
| uc002ayu.1 | 72904869 | 72911189 | 6320 | | | | | | |
| uc002ayv.1 | 72915511 | 72919107 | 3596 | | | | | | |
| uc002ayw.1 | 72915511 | 72922573 | 7062 | | | | | | |
| uc002ayx.1 | 72915511 | 72922573 | 7062 | | | | | | |
| uc002ayy.1 | 72915511 | 72922573 | 7062 | | | | | | |
| uc002ayz.1 | 72915511 | 72922573 | 7062 | | | | | | |
| uc002aza.1 | 72923125 | 72933513 | 10388 | | | | | | |
| uc002azb.1 | 72924249 | 72952723 | 28474 | | | | | | |
| uc002azc.1 | 72969462 | 72977618 | 8156 | | | | | | |

Fig. 30c

| #name | txStart | txEnd | size | fusion gene name | Rank size order | Comparative genomics peak order | standard | actual | gene size |
|---|---|---|---|---|---|---|---|---|---|
| uc002azd.1 | 72969462 | 72977618 | 8156 | | | | | | |
| uc002aze.1 | 72969462 | 72977618 | 8156 | | | | | | |
| uc002azf.1 | 72979385 | 72986232 | 6847 | | | | | | |
| uc002azg.1 | 72979385 | 72986232 | 6847 | | | | | | |
| uc002azh.1 | 72980359 | 72986232 | 5873 | | | | | | |
| uc002azi.1 | 72999671 | 73017425 | 17754 | | | | | | |
| uc002azj.1 | 73034495 | 73036828 | 2333 | | | | | | |
| uc002azk.1 | 73074953 | 73100889 | 25936 | | | | | | |
| uc002azl.1 | 73074953 | 73100889 | 25936 | | | | | | |
| uc002azm.1 | 73074953 | 73100889 | 25936 | | | | | | |
| uc002azn.1 | 73074953 | 73100889 | 25936 | | | | | | |
| uc002azo.1 | 73102979 | 73130120 | 27141 | | | | | | |

Fig. 30d

Chromosome position represented
chr4:22,402,742-24,500,798
Total number of genes 6

| #name | txStart | txEnd | | size | fusion gene name | Rank size order | Comparative genomics peak order | standard | actual | gene size |
|---|---|---|---|---|---|---|---|---|---|---|
| uc003gqp.1 | 22303687 | 22430290 | | 126603 | | | | | | |
| uc003gqq.1 | 22303687 | 22430290 | | 126603 | | | | | | |
| uc003gqr.1 | 22608271 | 22667583 | | 59312 | | | | | | |
| uc003gqs.1 | 23402741 | 23500798 | uc003gqs.1 | 98057 | PPARGC1A | 3 | 1 | 8 | 0 | 2 |
| uc003gqt.1 | 23402741 | 23500798 | | 98057 | | | | | | |
| uc003gqu.1 | 23493401 | 23500798 | | 7397 | | | | | | |
| uc003gqv.1 | 24138185 | 24144920 | | 6735 | | | | | | |
| uc003gqw.1 | 24138185 | 24149871 | | 11686 | | | | | | |
| uc003gqx.1 | 24138185 | 24195282 | | 57097 | | | | | | |
| uc003gqy.1 | 24406182 | 24411533 | | 5351 | | | | | | |
| uc003gqz.1 | 24406182 | 24411565 | | 5383 | | | | | | |
| uc003gra.1 | 24416837 | 24419055 | | 2218 | | | | | | |
| uc003grb.1 | 24418907 | 24523669 | | 104762 | | | | | | |
| uc003grc.1 | 24418907 | 24523669 | | 104762 | | | | | | |
| uc003grd.1 | 24418907 | 24523669 | | 104762 | | | | | | |
| uc003gre.1 | 24437678 | 24590924 | | 153246 | | | | | | |

Fig. 31

Chromosome position represented
chr17:34,718,972-36,767,420
Total number of genes 70

| #name | txStart | txEnd | size | fusion gene name | Rank size order | Comparative genomics peak order | standard | actual |
|---|---|---|---|---|---|---|---|---|
| uc002hrt.1 | 34670365 | 34811402 | 141037 | | | | | |
| uc002hru.1 | 34814068 | 34861030 | 46962 | | | | | |
| uc002hrv.1 | 34816379 | 34861030 | 44651 | | | | | |
| uc002hrw.1 | 34871817 | 34941882 | 70065 | | | | | |
| uc002hrx.1 | 34871817 | 34942045 | 70228 | | | | | |
| uc002hry.1 | 35013546 | 35017701 | 4155 | | | | | |
| uc002hrz.1 | 35036704 | 35046404 | 9700 | | | | | |
| uc002hsa.1 | 35036704 | 35046404 | 9700 | | | | | |
| uc002hsb.1 | 35038278 | 35046404 | 8126 | | | | | |
| uc002hsc.1 | 35038278 | 35046404 | 8126 | | | | | |
| uc002hsd.1 | 35046937 | 35073250 | 26313 | | | | | |
| uc002hse.1 | 35046937 | 35073250 | 26313 | | | | | |
| uc002hsf.1 | 35062876 | 35073250 | 10374 | | | | | |
| uc002hsg.1 | 35067751 | 35073250 | 5499 | | | | | |
| uc002hsh.1 | 35075124 | 35076333 | 1209 | | | | | |
| uc002hsi.1 | 35078032 | 35080254 | 2222 | | | | | |
| uc002hsj.1 | 35080900 | 35097836 | 16936 | | | | | |
| uc002hsk.1 | 35080900 | 35097836 | 16936 | | | | | |
| uc002hsl.1 | 35097918 | 35127436 | 29518 | | | | | |
| uc002hsm.1 | 35097918 | 35138441 | 40523 | | | | | |
| uc002hsn.1 | 35109779 | 35122109 | 12330 | | | | | |
| uc002hso.1 | 35109779 | 35138441 | 28662 | | | | | |
| uc002hsp.1 | 35109779 | 35138441 | 28662 | | | | | |
| uc002hsq.1 | 35138934 | 35140314 | 1380 | | | | | |
| uc002hsr.1 | 35147712 | 35157064 | 9352 | | | | | |
| uc002hss.1 | 35148115 | 35157064 | 8949 | | | | | |
| uc002hst.1 | 35152030 | 35157064 | 5034 | | | | | |
| uc002hsu.1 | 35174724 | 35273967 | 99243 | | | | | |
| uc002hsv.1 | 35174724 | 35273967 | 99243 | | | | | |

Fig. 32a

| #name | txStart | txEnd | size | fusion gene name | Rank size order | Comparative genomics peak order | standard | actual |
|---|---|---|---|---|---|---|---|---|
| uc002hsw.1 | 35174724 | 35273967 | 99243 | | | | | |
| uc002hsx.1 | 35174724 | 35273967 | 99243 | | | | | |
| uc002hsy.1 | 35174724 | 35273967 | 99243 | | | | | |
| uc002hsz.1 | 35174724 | 35273967 | 99243 | | | | | |
| uc002hta.1 | 35174724 | 35273967 | 99243 | | | | | |
| uc002htb.1 | 35174724 | 35273967 | 99243 | | | | | |
| uc002htc.1 | 35174724 | 35273967 | 99243 | | | | | |
| uc002htd.1 | 35174724 | 35273967 | 99243 | | | | | |
| uc002hte.1 | 35277980 | 35287675 | 9695 | | | | | |
| uc002htf.1 | 35277980 | 35287675 | 9695 | | | | | |
| uc002htg.1 | 35314373 | 35327319 | 12946 | | | | | |
| uc002hth.1 | 35314373 | 35328429 | 14056 | | | | | |
| uc002hti.1 | 35330821 | 35336620 | 5799 | | | | | |
| uc002htj.1 | 35330821 | 35337380 | 6559 | | | | | |
| uc002htk.1 | 35330821 | 35337380 | 6559 | | | | | |
| uc002htl.1 | 35372751 | 35387545 | 14794 | | | | | |
| uc002htm.1 | 35375436 | 35387545 | 12109 | | | | | |
| uc002htn.1 | 35390585 | 35407738 | 17153 | | | | | |
| uc002hto.1 | 35425213 | 35427592 | 2379 | | | | | |
| uc002htp.1 | 35425213 | 35427592 | 2379 | | | | | |
| uc002htq.1 | 35425213 | 35427592 | 2379 | | | | | |
| uc002htr.1 | 35428875 | 35432263 | 3388 | | | | | |
| uc002hts.1 | 35428875 | 35463652 | 34777 | | | | | |
| uc002htt.1 | 35428875 | 35464415 | 35540 | | | | | |
| uc002htu.1 | 35428875 | 35464415 | 35540 | | | | | |
| uc002htv.1 | 35472588 | 35499816 | 27228 | | | | | |
| uc002htw.1 | 35472588 | 35503646 | 31058 | | | | | |
| uc002htx.1 | 35472588 | 35503646 | 31058 | | | | | |
| uc002hty.1 | 35498020 | 35503043 | 5023 | | | | | |
| uc002htz.1 | 35502566 | 35510499 | 7933 | | | | | |
| uc002hua.1 | 35532392 | 35546568 | 14176 | | | | | |
| uc002hub.1 | 35532975 | 35546568 | 13593 | | | | | |
| uc002huc.1 | 35535961 | 35540087 | 4126 | | | | | |

Fig. 32b

| #name | txStart | txEnd | size | | fusion gene name | Rank size order | Comparative genomics peak order | standard | actual |
|---|---|---|---|---|---|---|---|---|---|
| | | | | | | | | | 2 |
| uc002hud.1 | 35540779 | 35546568 | 5789 | | | | | | |
| uc002hue.1 | 35550032 | 35581957 | 31925 | | | | | | |
| uc002huf.1 | 35588138 | 35605426 | 17288 | | | | | | |
| uc002hug.1 | 35629099 | 35691965 | 62866 | | | | | | |
| uc002huh.1 | 35629099 | 35691965 | 62866 | | | | | | |
| uc002hui.1 | 35629134 | 35691965 | 62831 | | | | | | |
| uc002huj.1 | 35697671 | 35712939 | 15268 | | | | | | |
| uc002huk.1 | 35718971 | 35767420 | 48449 | | | | | | |
| uc002hul.1 | 35728035 | 35767420 | 39385 | | | | | | |
| uc002hum.1 | 35740634 | 35820467 uc002hum.1 | 79833 | | RARA | 3 | b7 | 8 | NA |
| uc002hun.1 | 35751867 | 35767420 | 15553 | | | | | | |
| uc002huo.1 | 35770432 | 35774471 | 4039 | | | | | | |
| uc002hup.1 | 35798304 | 35799299 | 995 | | | | | | |
| uc002huq.1 | 35798321 | 35827695 | 29374 | | | | | | |
| uc002hur.1 | 35817744 | 35821254 | 3510 | | | | | | |
| uc002hus.1 | 35853201 | 35867508 | 14307 | | | | | | |
| uc002hut.1 | 35885625 | 35911341 | 25716 | | | | | | |
| uc002huu.1 | 35886155 | 35890653 | 4498 | | | | | | |
| uc002huv.1 | 35926803 | 35936780 | 9977 | | | | | | |
| uc002huw.1 | 35963547 | 35975250 | 11703 | | | | | | |
| uc002hux.1 | 36037505 | 36057629 | 20124 | | | | | | |
| uc002huy.1 | 36037505 | 36057629 | 20124 | | | | | | |
| uc002huz.1 | 36043946 | 36057629 | 13683 | | | | | | |
| uc002hva.1 | 36050351 | 36057629 | 7278 | | | | | | |
| uc002hvb.1 | 36066042 | 36074813 | 8771 | | | | | | |
| uc002hvc.1 | 36066042 | 36074890 | 8848 | | | | | | |
| uc002hvd.1 | 36107768 | 36113528 | 5760 | | | | | | |
| uc002hve.1 | 36157798 | 36165091 | 7293 | | | | | | |
| uc002hvf.1 | 36176015 | 36181937 | 5922 | | | | | | |
| uc002hvg.1 | 36186585 | 36192312 | 5727 | | | | | | |
| uc002hvh.1 | 36201973 | 36209737 | 7764 | | | | | | |
| uc002hvi.1 | 36227894 | 36232373 | 4479 | | | | | | |
| uc002hvj.1 | 36228899 | 36246052 | 17153 | | | | | | |

Fig. 32c

| #name | txStart | txEnd | fusion gene name size | Rank size order | Comparative genomics peak order | standard | actual |
|---|---|---|---|---|---|---|---|
| uc002hvk.1 | 36271080 | 36276988 | 5908 | | | | |
| uc002hvl.1 | 36285718 | 36295005 | 9287 | | | | |
| uc002hvm.1 | 36332477 | 36347362 | 14885 | | | | |
| uc002hvn.1 | 36338223 | 36346812 | 8589 | | | | |
| uc002hvo.1 | 36368194 | 36376670 | 8476 | | | | |
| uc002hvp.1 | 36387493 | 36396152 | 8659 | | | | |
| uc002hvq.1 | 36387493 | 36396779 | 9286 | | | | |
| uc002hvr.1 | 36403207 | 36403911 | 704 | | | | |
| uc002hvs.1 | 36408970 | 36409664 | 694 | | | | |
| uc002hvt.1 | 36418299 | 36418892 | 593 | | | | |
| uc002hvu.1 | 36435804 | 36436980 | 1176 | | | | |
| uc002hvv.1 | 36443662 | 36444633 | 971 | | | | |
| uc002hvw.1 | 36450336 | 36451239 | 903 | | | | |
| uc002hvx.1 | 36469018 | 36469877 | 859 | | | | |
| uc002hvy.1 | 36474893 | 36475657 | 764 | | | | |
| uc002hvz.1 | 36526959 | 36528138 | 1179 | | | | |
| uc002hwa.1 | 36532870 | 36533945 | 1075 | | | | |
| uc002hwb.1 | 36558701 | 36559580 | 879 | | | | |
| uc002hwc.1 | 36569431 | 36570509 | 1078 | | | | |
| uc002hwd.1 | 36587223 | 36587986 | 763 | | | | |
| uc002hwe.1 | 36593877 | 36595099 | 1222 | | | | |
| uc002hwf.1 | 36636425 | 36637430 | 1005 | | | | |
| uc002hwg.1 | 36642240 | 36643232 | 992 | | | | |
| uc002hwh.1 | 36647804 | 36648330 | 526 | | | | |
| uc002hwi.1 | 36659464 | 36660431 | 967 | | | | |
| uc002hwj.1 | 36724694 | 36725473 | 779 | | | | |
| uc002hwk.1 | 36755896 | 36760582 | 4686 | | | | |

Fig. 32d

Chromosome position represented
chr17:34,718,972-36,767,420
Total number of genes 70

| #name | txStart | txEnd | size | fusion gene name | Rank size order | Comparative genomics peak order | standard | actual |
|---|---|---|---|---|---|---|---|---|
| uc002hrt.1 | 34670365 | 34811402 | 141037 | | | | | |
| uc002hru.1 | 34814068 | 34861030 | 46962 | | | | | |
| uc002hrv.1 | 34816379 | 34861030 | 44651 | | | | | |
| uc002hrw.1 | 34871817 | 34941882 | 70065 | | | | | |
| uc002hrx.1 | 34871817 | 34942045 | 70228 | | | | | |
| uc002hry.1 | 35013546 | 35017701 | 4155 | | | | | |
| uc002hrz.1 | 35036704 | 35046404 | 9700 | | | | | |
| uc002hsa.1 | 35036704 | 35046404 | 9700 | | | | | |
| uc002hsb.1 | 35038278 | 35046404 | 8126 | | | | | |
| uc002hsc.1 | 35038278 | 35046404 | 8126 | | | | | |
| uc002hsd.1 | 35046937 | 35073250 | 26313 | | | | | |
| uc002hse.1 | 35046937 | 35073250 | 26313 | | | | | |
| uc002hsf.1 | 35062876 | 35073250 | 10374 | | | | | |
| uc002hsg.1 | 35067751 | 35073250 | 5499 | | | | | |
| uc002hsh.1 | 35075124 | 35076333 | 1209 | | | | | |
| uc002hsi.1 | 35078032 | 35080254 | 2222 | | | | | |
| uc002hsj.1 | 35080900 | 35097836 | 16936 | | | | | |
| uc002hsk.1 | 35080900 | 35097836 | 16936 | | | | | |
| uc002hsl.1 | 35097918 | 35127436 | 29518 | | | | | |
| uc002hsm.1 | 35097918 | 35138441 | 40523 | | | | | |
| uc002hsn.1 | 35109779 | 35122109 | 12330 | | | | | |
| uc002hso.1 | 35109779 | 35138441 | 28662 | | | | | |
| uc002hsp.1 | 35109779 | 35138441 | 28662 | | | | | |
| uc002hsq.1 | 35138934 | 35140314 | 1380 | | | | | |
| uc002hsr.1 | 35147712 | 35157064 | 9352 | | | | | |
| uc002hss.1 | 35148115 | 35157064 | 8949 | | | | | |
| uc002hst.1 | 35152030 | 35157064 | 5034 | | | | | |
| uc002hsu.1 | 35174724 | 35273967 | 99243 | | | | | |
| uc002hsv.1 | 35174724 | 35273967 | 99243 | | | | | |

Fig. 33a

| #name | txStart | txEnd | size | fusion gene name | Rank size order | Comparative genomics peak order | standard | actual |
|---|---|---|---|---|---|---|---|---|
| uc002hsw.1 | 35174724 | 35273967 | 99243 | | | | | |
| uc002hsx.1 | 35174724 | 35273967 | 99243 | | | | | |
| uc002hsy.1 | 35174724 | 35273967 | 99243 | | | | | |
| uc002hsz.1 | 35174724 | 35273967 | 99243 | | | | | |
| uc002hta.1 | 35174724 | 35273967 | 99243 | | | | | |
| uc002htb.1 | 35174724 | 35273967 | 99243 | | | | | |
| uc002htc.1 | 35174724 | 35273967 | 99243 | | | | | |
| uc002htd.1 | 35174724 | 35273967 | 99243 | | | | | |
| uc002hte.1 | 35277980 | 35287675 | 9695 | | | | | |
| uc002htf.1 | 35277980 | 35287675 | 9695 | | | | | |
| uc002htg.1 | 35314373 | 35327319 | 12946 | | | | | |
| uc002hth.1 | 35314373 | 35328429 | 14056 | | | | | |
| uc002hti.1 | 35330821 | 35336620 | 5799 | | | | | |
| uc002htj.1 | 35330821 | 35337380 | 6559 | | | | | |
| uc002htk.1 | 35330821 | 35337380 | 6559 | | | | | |
| uc002htl.1 | 35372751 | 35387545 | 14794 | | | | | |
| uc002htm.1 | 35375436 | 35387545 | 12109 | | | | | |
| uc002htn.1 | 35390585 | 35407738 | 17153 | | | | | |
| uc002hto.1 | 35425213 | 35427592 | 2379 | | | | | |
| uc002htp.1 | 35425213 | 35427592 | 2379 | | | | | |
| uc002htq.1 | 35425213 | 35427592 | 2379 | | | | | |
| uc002htr.1 | 35428875 | 35432263 | 3388 | | | | | |
| uc002hts.1 | 35428875 | 35463652 | 34777 | | | | | |
| uc002htt.1 | 35428875 | 35464415 | 35540 | | | | | |
| uc002htu.1 | 35428875 | 35464415 | 35540 | | | | | |
| uc002htv.1 | 35472588 | 35499816 | 27228 | | | | | |
| uc002htw.1 | 35472588 | 35503646 | 31058 | | | | | |
| uc002htx.1 | 35472588 | 35503646 | 31058 | | | | | |
| uc002hty.1 | 35498020 | 35503043 | 5023 | | | | | |
| uc002htz.1 | 35502566 | 35510499 | 7933 | | | | | |
| uc002hua.1 | 35532392 | 35546568 | 14176 | | | | | |
| uc002hub.1 | 35532975 | 35546568 | 13593 | | | | | |
| uc002huc.1 | 35535961 | 35540087 | 4126 | | | | | |

Fig. 33b

| #name | txStart | txEnd | | size | fusion gene name | Rank size order | Comparative genomics peak order | standard | actual | |
|---|---|---|---|---|---|---|---|---|---|---|
| uc002hud.1 | 35540779 | 35546568 | | 5789 | | | | | | |
| uc002hue.1 | 35550032 | 35581957 | | 31925 | | | | | | |
| uc002huf.1 | 35588138 | 35605426 | | 17288 | | | | | | |
| uc002hug.1 | 35629099 | 35691965 | | 62866 | | | | | | |
| uc002huh.1 | 35629099 | 35691965 | | 62866 | | | | | | |
| uc002hui.1 | 35629134 | 35691965 | | 62831 | | | | | | |
| uc002huj.1 | 35697671 | 35712939 | | 15268 | | | | | | |
| uc002huk.1 | 35718971 | 35767420 | | 48449 | | | | | | |
| uc002hul.1 | 35728035 | 35767420 | | 39385 | | | | | | |
| uc002hum.1 | 35740634 | 35820467 | uc002hum.1 | 79833 | RARA | 3 | b7 | 8 | NA | 2 |
| uc002hun.1 | 35751867 | 35767420 | | 15553 | | | | | | |
| uc002huo.1 | 35770432 | 35774471 | | 4039 | | | | | | |
| uc002hup.1 | 35798304 | 35799299 | | 995 | | | | | | |
| uc002huq.1 | 35798321 | 35827695 | | 29374 | | | | | | |
| uc002hur.1 | 35817744 | 35821254 | | 3510 | | | | | | |
| uc002hus.1 | 35853201 | 35867508 | | 14307 | | | | | | |
| uc002hut.1 | 35885625 | 35911341 | | 25716 | | | | | | |
| uc002huu.1 | 35886155 | 35890653 | | 4498 | | | | | | |
| uc002huv.1 | 35926803 | 35936780 | | 9977 | | | | | | |
| uc002huw.1 | 35963547 | 35975250 | | 11703 | | | | | | |
| uc002hux.1 | 36037505 | 36057629 | | 20124 | | | | | | |
| uc002huy.1 | 36037505 | 36057629 | | 20124 | | | | | | |
| uc002huz.1 | 36043946 | 36057629 | | 13683 | | | | | | |
| uc002hva.1 | 36050351 | 36057629 | | 7278 | | | | | | |
| uc002hvb.1 | 36066042 | 36074813 | | 8771 | | | | | | |
| uc002hvc.1 | 36066042 | 36074890 | | 8848 | | | | | | |
| uc002hvd.1 | 36107768 | 36113528 | | 5760 | | | | | | |
| uc002hve.1 | 36157798 | 36165091 | | 7293 | | | | | | |
| uc002hvf.1 | 36176015 | 36181937 | | 5922 | | | | | | |
| uc002hvg.1 | 36186585 | 36192312 | | 5727 | | | | | | |
| uc002hvh.1 | 36201973 | 36209737 | | 7764 | | | | | | |
| uc002hvi.1 | 36227894 | 36232373 | | 4479 | | | | | | |
| uc002hvj.1 | 36228899 | 36246052 | | 17153 | | | | | | |

Fig. 33c

| #name | txStart | txEnd | size | fusion gene name | Rank size order | Comparative genomics peak order | standard | actual |
|---|---|---|---|---|---|---|---|---|
| uc002hvk.1 | 36271080 | 36276988 | 5908 | | | | | |
| uc002hvl.1 | 36285718 | 36295005 | 9287 | | | | | |
| uc002hvm.1 | 36332477 | 36347362 | 14885 | | | | | |
| uc002hvn.1 | 36338223 | 36346812 | 8589 | | | | | |
| uc002hvo.1 | 36368194 | 36376670 | 8476 | | | | | |
| uc002hvp.1 | 36387493 | 36396152 | 8659 | | | | | |
| uc002hvq.1 | 36387493 | 36396779 | 9286 | | | | | |
| uc002hvr.1 | 36403207 | 36403911 | 704 | | | | | |
| uc002hvs.1 | 36408970 | 36409664 | 694 | | | | | |
| uc002hvt.1 | 36418299 | 36418892 | 593 | | | | | |
| uc002hvu.1 | 36435804 | 36436980 | 1176 | | | | | |
| uc002hvv.1 | 36443662 | 36444633 | 971 | | | | | |
| uc002hvw.1 | 36450336 | 36451239 | 903 | | | | | |
| uc002hvx.1 | 36469018 | 36469877 | 859 | | | | | |
| uc002hvy.1 | 36474893 | 36475657 | 764 | | | | | |
| uc002hvz.1 | 36526959 | 36528138 | 1179 | | | | | |
| uc002hwa.1 | 36532870 | 36533945 | 1075 | | | | | |
| uc002hwb.1 | 36558701 | 36559580 | 879 | | | | | |
| uc002hwc.1 | 36569431 | 36570509 | 1078 | | | | | |
| uc002hwd.1 | 36587223 | 36587986 | 763 | | | | | |
| uc002hwe.1 | 36593877 | 36595099 | 1222 | | | | | |
| uc002hwf.1 | 36636425 | 36637430 | 1005 | | | | | |
| uc002hwg.1 | 36642240 | 36643232 | 992 | | | | | |
| uc002hwh.1 | 36647804 | 36648330 | 526 | | | | | |
| uc002hwi.1 | 36659464 | 36660431 | 967 | | | | | |
| uc002hwj.1 | 36724694 | 36725473 | 779 | | | | | |
| uc002hwk.1 | 36755896 | 36760582 | 4686 | | | | | |

Fig. 33d

Chromosome position represented
chr21:34,081,968-36,343,455
Total number of genes 16

| #name | txStart | txEnd | size | fusion gene name | Rank size order | Comparative genomics peak order | standard | actual | gene size |
|---|---|---|---|---|---|---|---|---|---|
| uc002ysn.1 | 33878765 | 34206573 | 327808 | | | | | | |
| uc002ysw.1 | 33936653 | 34132672 | 196019 | | | | | | |
| uc002ysx.1 | 33936653 | 34132672 | 196019 | | | | | | |
| uc002ysy.1 | 33936653 | 34132672 | 196019 | | | | | | |
| uc002ysz.1 | 33936653 | 34132672 | 196019 | | | | | | |
| uc002yta.1 | 33936653 | 34183479 | 246826 | | | | | | |
| uc002ytb.1 | 33936653 | 34183479 | 246826 | | | | | | |
| uc002ytc.1 | 34012971 | 34111788 | 98817 | | | | | | |
| uc002ytd.1 | 34012971 | 34132672 | 119701 | | | | | | |
| uc002yte.1 | 34016762 | 34132672 | 115910 | | | | | | |
| uc002ytf.1 | 34096603 | 34111788 | 15185 | | | | | | |
| uc002ytg.1 | 34112440 | 34123224 | 10784 | | | | | | |
| uc002yth.1 | 34112440 | 34123919 | 11479 | | | | | | |
| uc002yti.1 | 34123141 | 34151031 | 27890 | | | | | | |
| uc002ytj.1 | 34152859 | 34180634 | 27775 | | | | | | |
| uc002ytk.1 | 34169527 | 34179696 | 10169 | | | | | | |
| uc002ytl.1 | 34197626 | 34210028 | 12402 | | | | | | |
| uc002ytm.1 | 34206462 | 34209898 | 3436 | | | | | | |
| uc002ytn.1 | 34225810 | 34265357 | 39547 | | | | | | |
| uc002yto.1 | 34367692 | 34400431 | 32739 | | | | | | |
| uc002ytp.1 | 34367692 | 34437200 | 69508 | | | | | | |
| uc002ytq.1 | 34389031 | 34400431 | 11400 | | | | | | |
| uc002ytr.1 | 34474917 | 34477416 | 2499 | | | | | | |
| uc002yts.1 | 34474917 | 34484090 | 9173 | | | | | | |
| uc002ytt.1 | 34658192 | 34665310 | 7118 | | | | | | |
| uc002ytu.1 | 34669659 | 34683321 | 13662 | | | | | | |
| uc002ytv.1 | 34669659 | 34696944 | 27285 | | | | | | |
| uc002ytw.1 | 34669659 | 34696944 | 27285 | | | | | | |
| uc002ytx.1 | 34669772 | 34683321 | 13549 | | | | | | |

Fig. 34a

| #name | txStart | txEnd | size | fusion gene name | Rank size order | Comparative genomics peak order | standard | actual | gene size |
|---|---|---|---|---|---|---|---|---|---|
| uc002yty.1 | 34712882 | 34718134 | 5252 | | | | | | |
| uc002ytz.1 | 34740857 | 34753772 | 12915 | | | | | | |
| uc002yua.1 | 34740857 | 34806443 | 65586 | | | | | | |
| uc002yub.1 | 34810653 | 34821131 | 10478 | | | | | | |
| uc002yuc.1 | 34810653 | 34908012 | 97359 | | | | | | |
| uc002yud.1 | 34810653 | 34908615 | 97962 | | | | | | |
| uc002yue.1 | 34810653 | 34909252 | 98599 | | | | | | |
| uc002yuf.1 | 34963557 | 35012389 | 48832 | | | | | | |
| uc002yug.1 | 35040013 | 35079038 | 39025 | | | | | | |
| uc002yuh.1 | 35081967 | 35182857 | 100890 | | | | | | |
| uc002yui.1 | 35081967 | 35182857 | 100890 | | | | | | |
| uc002yuj.1 | 35081967 | 35343455 | 261488 | | | | | | |
| uc002yuk.1 | 35081967 | 35343465 | 261498 | | | | | | |
| uc002yul.1 | 35091579 | 35128768 | 37189 | | | | | | |
| uc002yum.1 | 35091579 | 35343125 | 251546 | | | | | | |
| uc002yun.1 | 35115443 | 35124138 | 8695 | | | | | | |
| uc002yuo.1 | 35115443 | 35182857 | 67414 | | | | | | |
| uc002yup.1 | 35117630 | 35120573 | 2943 | | | | | | |
| uc002yuq.1 | 35127127 | 35150614 | 23487 | | | | | | |
| uc002yur.1 | 35153500 | 35174880 | 21380 | | | | | | |
| uc002yus.1 | 35153640 | 35153741 | 101 | | | | | | |
| uc002yut.1 | 35181009 | 36278917 uc002yut.1 | 1097908 | RUNX1 | 1 | 2 | 26 | 2 | 20 |
| uc002yuu.1 | 36328708 | 36354789 | 26081 | | | | | | |
| uc002yuv.1 | 36328708 | 36358576 | 29868 | | | | | | |
| uc002yuw.1 | 36328709 | 36354429 | 25720 | | | | | | |
| uc002yux.1 | 36328709 | 36354789 | 26080 | | | | | | |
| uc002yuy.1 | 36337851 | 36354481 | 16630 | | | | | | |
| uc002yuz.1 | 36337851 | 36354481 | 16630 | | | | | | |
| uc002yva.1 | 36337851 | 36373557 | 35706 | | | | | | |

Fig. 34b

Chromosome position represented
chr8:92,040,328-94,176,619
Total number of genes 8

| #name | txStart | txEnd | size | fusion gene name | Rank size order | Comparative genomics peak order | standard | actual | gene size |
|---|---|---|---|---|---|---|---|---|---|
| uc003yeq.1 | 91872953 | 92040806 | 167853 | | | | | | |
| uc003yer.1 | 92022142 | 92040806 | 18664 | | | | | | |
| uc003yes.1 | 92075674 | 92122224 | 46550 | | | | | | |
| uc003yet.1 | 92149319 | 92151500 | 2181 | | | | | | |
| uc003yeu.1 | 92151753 | 92168497 | 16744 | | | | | | |
| uc003yev.1 | 92184022 | 92300640 | 116618 | | | | | | |
| uc003yew.1 | 92199779 | 92300640 | 100861 | | | | | | |
| uc003yex.1 | 92290897 | 92479554 | 188657 | | | | | | |
| uc003yey.1 | 92290897 | 92479554 | 188657 | | | | | | |
| uc003yez.1 | 92330691 | 92476122 | 145431 | | | | | | |
| uc003yfa.1 | 92330691 | 92479554 | 148863 | | | | | | |
| uc003yfb.1 | 93040327 | 93099084 | 58757 | | | | | | |
| uc003yfc.1 | 93040327 | 93144367 | 104040 | | | | | | |
| uc003yfd.1 | 93040327 | 93157540 | 117213 | | | | | | |
| uc003yfe.1 | 93040327 | 93176619 uc003yfe.1 | 136292 | RUNX1T1 | 5 | 1 | 9 | 0 | 3 |
| uc003yff.1 | 93085825 | 93099084 | 13259 | | | | | | |
| uc003yfg.1 | 93091049 | 93099084 | 8035 | | | | | | |
| uc003yfh.1 | 93091049 | 93176619 | 85570 | | | | | | |
| uc003yfi.1 | 93098676 | 93144367 | 45691 | | | | | | |
| uc003yfj.1 | 93794365 | 93959041 | 164676 | | | | | | |
| uc003yfk.1 | 93965038 | 93967189 | 2151 | | | | | | |
| uc003yfl.1 | 93966724 | 94047527 | 80803 | | | | | | |
| uc003yfm.1 | 93966724 | 94047527 | 80803 | | | | | | |
| uc003yfn.1 | 93966738 | 94047527 | 80789 | | | | | | |
| uc003yfo.1 | 93966738 | 94047527 | 80789 | | | | | | |
| uc003yfp.1 | 93966738 | 94047527 | 80789 | | | | | | |
| uc003yfq.1 | 93966738 | 94047527 | 80789 | | | | | | |
| uc003yfr.1 | 93966738 | 94099077 | 132339 | | | | | | |
| uc003yfs.1 | 94035809 | 94046892 | 11083 | | | | | | |

Fig. 35

Chromosome position represented
chr18:20,850,215-22,924,609
Total number of genes 7

| #name | txStart | txEnd | size | fusion gene name | Rank size order | Comparative genomics peak order | standard | actual |
|---|---|---|---|---|---|---|---|---|
| uc002kvk.1 | 20895888 | 21186114 | 290226 | | | | | |
| uc002kvl.1 | 20895888 | 21186114 | 290226 | | | | | |
| uc002kvm.1 | 21850214 | 21924609 | 74395 | | | | | |
| uc002kvn.1 | 21850214 | 21924609 uc002kvn.1 | 74395 | SS18 | 5 | b7 | 8 | NA | 2 |
| uc002kvo.1 | 21967813 | 22027317 | 59504 | | | | | |
| uc002kvp.1 | 21967813 | 22027317 | 59504 | | | | | |
| uc002kvq.1 | 21967813 | 22027317 | 59504 | | | | | |
| uc002kvr.1 | 21967813 | 22027317 | 59504 | | | | | |
| uc002kvs.1 | 22060844 | 22225645 | 164801 | | | | | |
| uc002kvt.1 | 22060844 | 22225645 | 164801 | | | | | |
| uc002kvu.1 | 22060844 | 22225645 | 164801 | | | | | |
| uc002kvv.1 | 22288871 | 22474306 | 185435 | | | | | |
| uc002kvw.1 | 22289420 | 22383118 | 93698 | | | | | |
| uc002kvx.1 | 22289605 | 22289856 | 251 | | | | | |
| uc002kvy.1 | 22289683 | 22310853 | 21170 | | | | | |
| uc002kvz.1 | 22686004 | 22696573 | 10569 | | | | | |
| uc002kwa.1 | 22686004 | 22699714 | 13710 | | | | | |
| uc002kwb.1 | 22699268 | 22769908 | 70640 | | | | | |
| uc002kwc.1 | 22749611 | 22882465 | 132854 | | | | | |
| uc002kwd.1 | 22749611 | 22976969 | 227358 | | | | | |
| uc002kwe.1 | 22749611 | 23019279 | 269668 | | | | | |

Fig. 36

Chromosome position represented
chr18:20,850,215-22,924,609
Total number of genes 7

| #name | txStart | txEnd | | size | fusion gene name | Rank size order | Comparative genomics peak order | standard | actual |
|---|---|---|---|---|---|---|---|---|---|
| uc002kvk.1 | 20895888 | 21186114 | | 290226 | | | | | |
| uc002kvl.1 | 20895888 | 21186114 | | 290226 | | | | | |
| uc002kvm.1 | 21850214 | 21924609 | | 74395 | | | | | |
| uc002kvn.1 | 21850214 | 21924609 | uc002kvn.1 | 74395 | SS18 | 5 | b7 | 8 | NA | 2 |
| uc002kvo.1 | 21967813 | 22027317 | | 59504 | | | | | |
| uc002kvp.1 | 21967813 | 22027317 | | 59504 | | | | | |
| uc002kvq.1 | 21967813 | 22027317 | | 59504 | | | | | |
| uc002kvr.1 | 21967813 | 22027317 | | 59504 | | | | | |
| uc002kvs.1 | 22060844 | 22225645 | | 164801 | | | | | |
| uc002kvt.1 | 22060844 | 22225645 | | 164801 | | | | | |
| uc002kvu.1 | 22060844 | 22225645 | | 164801 | | | | | |
| uc002kvv.1 | 22288871 | 22474306 | | 185435 | | | | | |
| uc002kvw.1 | 22289420 | 22383118 | | 93698 | | | | | |
| uc002kvx.1 | 22289605 | 22289856 | | 251 | | | | | |
| uc002kvy.1 | 22289683 | 22310853 | | 21170 | | | | | |
| uc002kvz.1 | 22686004 | 22696573 | | 10569 | | | | | |
| uc002kwa.1 | 22686004 | 22699714 | | 13710 | | | | | |
| uc002kwb.1 | 22699268 | 22769908 | | 70640 | | | | | |
| uc002kwc.1 | 22749611 | 22882465 | | 132854 | | | | | |
| uc002kwd.1 | 22749611 | 22976969 | | 227358 | | | | | |
| uc002kwe.1 | 22749611 | 23019279 | | 269668 | | | | | |

Fig. 37

Chromosome position represented
chr17:26,288,185-28,352,162
Total number of genes  17

| #name | txStart | txEnd | size | fusion gene name | Rank size order | Comparative genomics peak order | standard | actual | gene size |
|---|---|---|---|---|---|---|---|---|---|
| uc002htx.1 | 26272879 | 26310337 | 37458 | | | | | | |
| uc002hty.1 | 26272879 | 26310337 | 37458 | | | | | | |
| uc002htz.1 | 26322081 | 26351053 | 28972 | | | | | | |
| uc002hga.1 | 26322081 | 26351053 | 28972 | | | | | | |
| uc002hgb.1 | 26322081 | 26351053 | 28972 | | | | | | |
| uc002hgc.1 | 26326478 | 26327143 | 665 | | | | | | |
| uc002hgd.1 | 26375328 | 26382727 | 7399 | | | | | | |
| uc002hge.1 | 26446120 | 26570503 | 124383 | | | | | | |
| uc002hgf.1 | 26446120 | 26573908 | 127788 | | | | | | |
| uc002hgg.1 | 26446120 | 26728821 | 282701 | | | | | | |
| uc002hgh.1 | 26446120 | 26728821 | 282701 | | | | | | |
| uc002hgi.1 | 26576226 | 26683048 | 106822 | | | | | | |
| uc002hgj.1 | 26645793 | 26648481 | 2688 | | | | | | |
| uc002hgk.1 | 26654918 | 26665217 | 10299 | | | | | | |
| uc002hgl.1 | 26668800 | 26672843 | 4043 | | | | | | |
| uc002hgm.1 | 26668800 | 26672843 | 4043 | | | | | | |
| uc002hgn.1 | 26742767 | 26889352 | 146585 | | | | | | |
| uc002hgo.1 | 26839280 | 26889352 | 50072 | | | | | | |
| uc002hgp.1 | 27203011 | 27210369 | 7358 | | | | | | |
| uc002hgq.1 | 27214302 | 27239353 | 25051 | | | | | | |
| uc002hgr.1 | 27214302 | 27252842 | 38540 | | | | | | |
| uc002hgs.1 | 27288184 | 27352162 | 63978 | | | | | | |
| uc002hgt.1 | 27288184 | 27352162 uc002hgt.1 | 63978 | SUZ12 | b5 | 2 | 8 | 0 | 2 |
| uc002hgu.1 | 27372267 | 27404632 | 32365 | | | | | | |
| uc002hgv.1 | 27493585 | 27560870 | 67285 | | | | | | |
| uc002hgw.1 | 27493585 | 27576859 | 83274 | | | | | | |
| uc002hgx.1 | 27493585 | 27576859 | 83274 | | | | | | |
| uc002hgy.1 | 27493585 | 27576859 | 83274 | | | | | | |
| uc002hgz.1 | 27493585 | 27576859 | 83274 | | | | | | |

Fig. 38a

| #name | txStart | txEnd | size | fusion gene name | Rank size order | Comparative genomics peak order | standard | actual | gene size |
|---|---|---|---|---|---|---|---|---|---|
| uc002hha.1 | 27493585 | 27576859 | 83274 | | | | | | |
| uc002hhb.1 | 27493585 | 27576859 | 83274 | | | | | | |
| uc002hhc.1 | 27501499 | 27502703 | 1204 | | | | | | |
| uc002hhd.1 | 27522178 | 27576859 | 54681 | | | | | | |
| uc002hhe.1 | 27617307 | 27675793 | 58486 | | | | | | |
| uc002hhf.1 | 27618935 | 27675793 | 56858 | | | | | | |
| uc002hhg.1 | 27682501 | 27693302 | 10801 | | | | | | |
| uc002hhh.1 | 27701269 | 27721583 | 20314 | | | | | | |
| uc002hhi.1 | 27701269 | 27721583 | 20314 | | | | | | |
| uc002hhj.1 | 27701269 | 27721583 | 20314 | | | | | | |
| uc002hhk.1 | 27701269 | 27732088 | 30819 | | | | | | |
| uc002hhl.1 | 27711729 | 27732088 | 20359 | | | | | | |
| uc002hhm.1 | 27795614 | 27832155 | 36541 | | | | | | |
| uc002hhn.1 | 27838217 | 27842384 | 4167 | | | | | | |
| uc002hho.1 | 27843740 | 28228015 | 384275 | | | | | | |
| uc002hhp.1 | 27945333 | 28228015 | 282682 | | | | | | |
| uc002hhq.1 | 28279040 | 28292780 | 13740 | | | | | | |
| uc002hhr.1 | 28279040 | 28292780 | 13740 | | | | | | |
| uc002hhs.1 | 28342994 | 28349005 | 6011 | | | | | | |

Fig. 38b

Chromosome position represented
chr21:40,758,351-42,801,948
Total number of genes 21

| #name | txStart | txEnd | size | fusion gene name | Rank size order | Comparative genomics peak order | standard | actual |
|---|---|---|---|---|---|---|---|---|
| uc002yyq.1 | 40306212 | 41140909 | 834697 | | | | | |
| uc002yyr.1 | 40306212 | 41140909 | 834697 | | | | | |
| uc002yyv.1 | 41435296 | 41441861 | 6565 | | | | | |
| uc002yyw.1 | 41461597 | 41570394 | 108797 | | | | | |
| uc002yyx.1 | 41461597 | 41570394 | 108797 | | | | | |
| uc002yyy.1 | 41461597 | 41570394 | 108797 | | | | | |
| uc002yyz.1 | 41469027 | 41479036 | 10009 | | | | | |
| uc002yza.1 | 41598067 | 41651524 | 53457 | | | | | |
| uc002yzb.1 | 41610530 | 41651524 | 40994 | | | | | |
| uc002yzc.1 | 41610530 | 41651524 | 40994 | | | | | |
| uc002yzd.1 | 41616616 | 41651524 | 34908 | | | | | |
| uc002yze.1 | 41655819 | 41661103 | 5284 | | | | | |
| uc002yzf.1 | 41655819 | 41702739 | 46920 | | | | | |
| uc002yzg.1 | 41683339 | 41702739 | 19400 | | | | | |
| uc002yzh.1 | 41714311 | 41753008 | 38697 | | | | | |
| uc002yzi.1 | 41720023 | 41753008 | 32985 | | | | | |
| uc002yzj.1 | 41758350 | 41801948 uc002yzj.1 | 43598 | tmprss2 | b5 | b7 | 7 | NA |
| uc002yzk.1 | 41758352 | 41760885 | 2533 | | | | | |
| uc002yzl.1 | 42004748 | 42009004 | 4256 | | | | | |
| uc002yzm.1 | 42009664 | 42010809 | 1145 | | | | | |
| uc002yzn.1 | 42032597 | 42060318 | 27721 | | | | | |
| uc002yzo.1 | 42091453 | 42172660 | 81207 | | | | | |
| uc002yzp.1 | 42091453 | 42172660 | 81207 | | | | | |
| uc002yzq.1 | 42094222 | 42172660 | 78438 | | | | | |
| uc002yzr.1 | 42094222 | 42172660 | 78438 | | | | | |
| uc002yzs.1 | 42178287 | 42194927 | 16640 | | | | | NA |
| uc002yzt.1 | 42178287 | 42201421 | 23134 | | | | | |
| uc002yzu.1 | 42178287 | 42212211 | 33924 | | | | | NA |
| uc002yzv.1 | 42178287 | 42219868 | 41581 | | | | | |

Fig. 39a

| #name | txStart | txEnd | size | fusion gene name | Rank size order | Comparative genomics peak order | standard | actual |
|---|---|---|---|---|---|---|---|---|
| uc002yzw.1 | 42178287 | 42247068 | 68781 | | | | | |
| uc002yzx.1 | 42194130 | 42219868 | 25738 | | | | | |
| uc002yzy.1 | 42280008 | 42303519 | 23511 | | | | | |
| uc002yzz.1 | 42280008 | 42303519 | 23511 | | | | | |
| uc002zaa.1 | 42280008 | 42303519 | 23511 | | | | | |
| uc002zab.1 | 42280008 | 42303519 | 23511 | | | | | |
| uc002zac.1 | 42285670 | 42303519 | 17849 | | | | | |
| uc002zad.1 | 42356136 | 42436174 | 80038 | | | | | |
| uc002zae.1 | 42356136 | 42436174 | 80038 | | | | | |
| uc002zaf.1 | 42364494 | 42436174 | 71680 | | | | | |
| uc002zag.1 | 42364494 | 42436174 | 71680 | | | | | |
| uc002zah.1 | 42368072 | 42370042 | 1970 | | | | | |
| uc002zai.1 | 42378469 | 42397266 | 18797 | | | | | |
| uc002zaj.1 | 42378469 | 42397266 | 18797 | | | | | |
| uc002zak.1 | 42395312 | 42401630 | 6318 | | | | | |
| uc002zal.1 | 42413697 | 42436174 | 22477 | | | | | |
| uc002zam.1 | 42492867 | 42590423 | 97556 | | | | | |
| uc002zan.1 | 42492867 | 42590423 | 97556 | | | | | |
| uc002zao.1 | 42509255 | 42590423 | 81168 | | | | | |
| uc002zap.1 | 42512335 | 42590423 | 78088 | | | | | |
| uc002zaq.1 | 42512335 | 42590423 | 78088 | | | | | |
| uc002zar.1 | 42513076 | 42590423 | 77347 | | | | | |
| uc002zas.1 | 42549262 | 42590423 | 41161 | | | | | |
| uc002zat.1 | 42579058 | 42588514 | 9456 | | | | | |
| uc002zau.1 | 42592172 | 42593988 | 1816 | | | | | |
| uc002zav.1 | 42605231 | 42608775 | 3544 | | | | | |
| uc002zaw.1 | 42639535 | 42644176 | 4641 | | | | | |
| uc002zax.1 | 42655459 | 42659713 | 4254 | | | | | |
| uc002zay.1 | 42665067 | 42676929 | 11862 | | | | | |
| uc002zaz.1 | 42665067 | 42682296 | 17229 | | | | | |
| uc002zba.1 | 42665067 | 42683596 | 18529 | | | | | |
| uc002zbb.1 | 42665067 | 42689269 | 24202 | | | | | |
| uc002zbc.1 | 42665067 | 42689269 | 24202 | | | | | |

Fig. 39b

| #name | txStart | txEnd | size | fusion gene name | Rank size order | Comparative genomics peak order | standard | actual |
|---|---|---|---|---|---|---|---|---|
| uc002zbd.1 | 42675053 | 42689269 | 14216 | | | | | |
| uc002zbe.1 | 42697087 | 42740843 | 43756 | | | | | |
| uc002zbf.1 | 42697087 | 42740843 | 43756 | | | | | |
| uc002zbg.1 | 42765665 | 42789470 | 23805 | | | | | |
| uc002zbh.1 | 42789186 | 42811689 | 22503 | | | | | |
| uc002zbi.1 | 42792810 | 42874619 | 81809 | | | | | |

Fig. 39c

Chromosome position represented
chr21:40,758,351-42,801,948
Total number of genes: 21

| #name | txStart | txEnd | size | fusion gene name | Rank size order | Comparative genomics peak order | standard | actual |
|---|---|---|---|---|---|---|---|---|
| uc002yyq.1 | 40306212 | 41140909 | 834697 | | | | | |
| uc002yyr.1 | 40306212 | 41140909 | 834697 | | | | | |
| uc002yyv.1 | 41435296 | 41441861 | 6565 | | | | | |
| uc002yyw.1 | 41461597 | 41570394 | 108797 | | | | | |
| uc002yyx.1 | 41461597 | 41570394 | 108797 | | | | | |
| uc002yyy.1 | 41461597 | 41570394 | 108797 | | | | | |
| uc002yyz.1 | 41469027 | 41479036 | 10009 | | | | | |
| uc002yza.1 | 41598067 | 41651524 | 53457 | | | | | |
| uc002yzb.1 | 41610530 | 41651524 | 40994 | | | | | |
| uc002yzc.1 | 41610530 | 41651524 | 40994 | | | | | NA |
| uc002yzd.1 | 41616616 | 41651524 | 34908 | | | | | |
| uc002yze.1 | 41655819 | 41661103 | 5284 | | | | | |
| uc002yzf.1 | 41655819 | 41702739 | 46920 | | | | NA | |
| uc002yzg.1 | 41683339 | 41702739 | 19400 | | | | | |
| uc002yzh.1 | 41714311 | 41753008 | 38697 | | | | | |
| uc002yzi.1 | 41720023 | 41753008 | 32985 | | | | | |
| uc002yzj.1 | 41758350 | 41801948 uc002yzj.1 | 43598 | tmprss2 | b5 | b7 | 1 | |
| uc002yzk.1 | 41758352 | 41760885 | 2533 | | | | | |
| uc002yzl.1 | 42004748 | 42009004 | 4256 | | | | | |
| uc002yzm.1 | 42009664 | 42010809 | 1145 | | | | | |
| uc002yzn.1 | 42032597 | 42060318 | 27721 | | | | | |
| uc002yzo.1 | 42091453 | 42172660 | 81207 | | | | | |
| uc002yzp.1 | 42091453 | 42172660 | 81207 | | | | | |
| uc002yzq.1 | 42094222 | 42172660 | 78438 | | | | | |
| uc002yzr.1 | 42094222 | 42172660 | 78438 | | | | | |
| uc002yzs.1 | 42178287 | 42194927 | 16640 | | | | | |
| uc002yzt.1 | 42178287 | 42201421 | 23134 | | | | | |
| uc002yzu.1 | 42178287 | 42212211 | 33924 | | | | | |
| uc002yzv.1 | 42178287 | 42219868 | 41581 | | | | | |

Fig. 40a

| #name | txStart | txEnd | size | fusion gene name | Rank size order | Comparative genomics peak order | standard | actual |
|---|---|---|---|---|---|---|---|---|
| uc002yzw.1 | 42178287 | 42247068 | 68781 | | | | | |
| uc002yzx.1 | 42194130 | 42219868 | 25738 | | | | | |
| uc002yzy.1 | 42280008 | 42303519 | 23511 | | | | | |
| uc002yzz.1 | 42280008 | 42303519 | 23511 | | | | | |
| uc002zaa.1 | 42280008 | 42303519 | 23511 | | | | | |
| uc002zab.1 | 42280008 | 42303519 | 23511 | | | | | |
| uc002zac.1 | 42285670 | 42303519 | 17849 | | | | | |
| uc002zad.1 | 42356136 | 42436174 | 80038 | | | | | |
| uc002zae.1 | 42356136 | 42436174 | 80038 | | | | | |
| uc002zaf.1 | 42364494 | 42436174 | 71680 | | | | | |
| uc002zag.1 | 42364494 | 42436174 | 71680 | | | | | |
| uc002zah.1 | 42368072 | 42370042 | 1970 | | | | | |
| uc002zai.1 | 42378469 | 42397266 | 18797 | | | | | |
| uc002zaj.1 | 42378469 | 42397266 | 18797 | | | | | |
| uc002zak.1 | 42395312 | 42401630 | 6318 | | | | | |
| uc002zal.1 | 42413697 | 42436174 | 22477 | | | | | |
| uc002zam.1 | 42492867 | 42590423 | 97556 | | | | | |
| uc002zan.1 | 42492867 | 42590423 | 97556 | | | | | |
| uc002zao.1 | 42509255 | 42590423 | 81168 | | | | | |
| uc002zap.1 | 42512335 | 42590423 | 78088 | | | | | |
| uc002zaq.1 | 42512335 | 42590423 | 78088 | | | | | |
| uc002zar.1 | 42513076 | 42590423 | 77347 | | | | | |
| uc002zas.1 | 42549262 | 42590423 | 41161 | | | | | |
| uc002zat.1 | 42579058 | 42588514 | 9456 | | | | | |
| uc002zau.1 | 42592172 | 42593988 | 1816 | | | | | |
| uc002zav.1 | 42605231 | 42608775 | 3544 | | | | | |
| uc002zaw.1 | 42639535 | 42644176 | 4641 | | | | | |
| uc002zax.1 | 42655459 | 42659713 | 4254 | | | | | |
| uc002zay.1 | 42665067 | 42676929 | 11862 | | | | | |
| uc002zaz.1 | 42665067 | 42682296 | 17229 | | | | | |
| uc002zba.1 | 42665067 | 42683596 | 18529 | | | | | |
| uc002zbb.1 | 42665067 | 42689269 | 24202 | | | | | |
| uc002zbc.1 | 42665067 | 42689269 | 24202 | | | | | |

Fig. 40b

| #name | txStart | txEnd | size | fusion gene name | Rank size order | Comparative genomics peak order | standard | actual |
|---|---|---|---|---|---|---|---|---|
| uc002zbd.1 | 42675053 | 42689269 | 14216 | | | | | |
| uc002zbe.1 | 42697087 | 42740843 | 43756 | | | | | |
| uc002zbf.1 | 42697087 | 42740843 | 43756 | | | | | |
| uc002zbg.1 | 42765665 | 42789470 | 23805 | | | | | |
| uc002zbh.1 | 42789186 | 42811689 | 22503 | | | | | |
| uc002zbi.1 | 42792810 | 42874619 | 81809 | | | | | |

Fig. 40c

Chromosome position represented
chr11:112,435,641-114,626,607
Total number of genes 18

| #name | txStart | txEnd | size | fusion gene name | Rank size order | Comparative genomics peak order | standard | actual | gene size |
|---|---|---|---|---|---|---|---|---|---|
| uc001pno.1 | 112337204 | 112597835 | 260631 | | | | | | |
| uc001pnp.1 | 112337204 | 112641129 | 303925 | | | | | | |
| uc001pnq.1 | 112337204 | 112654368 | 317164 | | | | | | |
| uc001pnr.1 | 112337204 | 112654368 | 317164 | | | | | | |
| uc001pns.1 | 112631808 | 112654368 | 22560 | | | | | | |
| uc001pnt.1 | 112648951 | 112654368 | 5417 | | | | | | |
| uc001pnu.1 | 112690460 | 112742324 | 51864 | | | | | | |
| uc001pnv.1 | 112690460 | 112742324 | 51864 | | | | | | |
| uc001pnw.1 | 112690460 | 112749228 | 58768 | | | | | | |
| uc001pnx.1 | 112690533 | 112742324 | 51791 | | | | | | |
| uc001pny.1 | 112763722 | 112776350 | 12628 | | | | | | |
| uc001pnz.1 | 112785526 | 112800904 | 15378 | | | | | | |
| uc001poa.1 | 112785526 | 112851091 | 65565 | | | | | | |
| uc001pob.1 | 112785526 | 112851091 | 65565 | | | | | | |
| uc001poc.1 | 113063482 | 113082305 | 18823 | | | | | | |
| uc001pod.1 | 113063482 | 113082305 | 18823 | | | | | | |
| uc001poe.1 | 113109118 | 113149635 | 40517 | | | | | | |
| uc001pof.1 | 113165162 | 113167092 | 1930 | | | | | | |
| uc001pog.1 | 113173806 | 113205399 | 31593 | | | | | | |
| uc001poh.1 | 113173806 | 113251466 | 77660 | | | | | | |
| uc001poi.1 | 113173806 | 113251466 | 77660 | | | | | | |
| uc001poj.1 | 113173806 | 113251466 | 77660 | | | | | | |
| uc001pok.1 | 113189687 | 113251466 | 61779 | | | | | | |
| uc001pol.1 | 113280798 | 113322493 | 41695 | | | | | | |
| uc001pom.1 | 113285164 | 113322493 | 37329 | | | | | | |
| uc001pon.1 | 113351119 | 113366244 | 15125 | | | | | | |
| uc001poo.1 | 113351119 | 113366244 | 15125 | | | | | | |
| uc001pop.1 | 113435640 | 113565696 | 130056 | | | | | | |
| uc001pop.1 uc001pop.1 | 113435640 | 113626607 | 190967 | ZBTB16 | 3 | 4 | 10 | 0 | 4 |
| uc001poq.1 | 113436497 | 113626607 | 190110 | | | | | | |

Fig. 41a

| #name | txStart | txEnd | size | fusion gene name | Rank size order | Comparative genomics peak order | standard | actual | gene size |
|---|---|---|---|---|---|---|---|---|---|
| uc001por.1 | 113633762 | 113688448 | 54686 | | | | | | |
| uc001pos.1 | 113671744 | 113688448 | 16704 | | | | | | |
| uc001pot.1 | 113767379 | 113776349 | 8970 | | | | | | |
| uc001pou.1 | 113775002 | 113776440 | 1438 | | | | | | |
| uc001pov.1 | 113776593 | 113784845 | 8252 | | | | | | |
| uc001pow.1 | 113776593 | 113784845 | 8252 | | | | | | |
| uc001pox.1 | 113776593 | 113784845 | 8252 | | | | | | |
| uc001poy.1 | 113815386 | 113826210 | 10824 | | | | | | |
| uc001poz.1 | 113815386 | 113826210 | 10824 | | | | | | |
| uc001ppa.1 | 113897646 | 113935790 | 38144 | | | | | | |
| uc001ppb.1 | 113904727 | 113930302 | 25575 | | | | | | |
| uc001ppc.1 | 113946522 | 113971694 | 25172 | | | | | | |
| uc001ppd.1 | 113946522 | 113971694 | 25172 | | | | | | |
| uc001ppe.1 | 114054466 | 114084572 | 30106 | | | | | | |
| uc001ppf.1 | 114545163 | 114880325 | 335162 | | | | | | |
| uc001ppg.1 | 114549559 | 114551260 | 1701 | | | | | | |
| uc001pph.1 | 114550226 | 114593921 | 43695 | | | | | | |
| uc001ppi.1 | 114550226 | 114880325 | 330099 | | | | | | |
| uc001ppj.1 | 114550226 | 114880325 | 330099 | | | | | | |
| uc001ppk.1 | 114550226 | 114880325 | 330099 | | | | | | |
| uc001ppl.1 | 114590419 | 114880325 | 289906 | | | | | | |

Fig. 41b

|   | Fusion gene | Translocation |   | Fusion gene | Translocation |
|---|---|---|---|---|---|
|   | TEL/EVI1 |   |   | MLL | t(6;11)(q27: q23) |
|   | PML/RARA |   |   | MLL | t(6;11)(q27: q23) |
| 1 | unknown | t(15;16)(q13: q13) |   | MLL/ELL | t(11;19)(q23: p13.1) |
|   | MLL-AF10 |   |   | unknown | t(5;17)(q13: q12) |
|   | AML1-ETO |   |   | unknown | t(11;12)(q13: q24) |
|   | PML/RARA |   |   | AML-1/RUNX1 | t(6;21)(q22: q22) |
| 2 | unknown | t(2;11)(p23: q23) |   | RPN1-EVI1 | t(3;3)(q21: q26) |
|   | TEL/EVI1 |   |   | unknown | t(10;11)(p13: q13) |
|   | MDS1/EVI1 |   |   | MLL/ELL | t(11;19)(q23: p13.1) |
|   | RUNX1/MTG16 |   |   | unknown | t(6;11)(p23: q13) |
|   | MDS1/EVI1 |   |   | unknown | t(4;21)(q22: q11.2) |
|   | unknown | t(4;12)(p10: q10) |   | unknown | t(2;17)(q11.2: p13) |
|   | honerin |   |   | unknown | t(10;11)(p13: q13) |
| 3 | unknown | t(1;11)(p36: q16) |   | unknown | t(1;9)(p31: q34) |
| 4 | unknown | t(14;19)(q32: q13.2) |   | unknown | t(1;15)(p34: q21) |
| 5 | unknown | t(5;15)(q13: q13) |   | unknown | t(3;13)(q21: q34) |
|   | IgH-ECR |   |   | unknown | t(3;12)(q26: q13) |
|   |   |   |   | AML-MTG16 | t(4;21)(q22: p11.2) |
| 6 |   | t(16;19)(q24: q13.1) |   | unknown | t(3;12)(q26: q13-21) |
| 7 | unknown | t(7;17)(q22: q12) |   | unknown | t(4;21)(q22: q21) |
| 8 | unknown | t(5;19)(p11.2: q13.1) |   | MLL-ELL | t(11;19)(q23: p13.1) |
|   | unknown | t(19;21)(q13.1q11.2) |   |   |   |
|   | unknown | t(7;17)(q22: q12) |   |   |   |
| 9 | unknown | t(3;12)(q21: q13) |   |   |   |
|   | unknown | t(7;22)(q22: q13) |   |   |   |
| 10 | unknown | t(5;11)(q13: q23) |   |   |   |
|   | MLL-ELL | t(11;19)(q23: p13.1) |   |   |   |
|   | AML1/RUNX1 | t(8;21)(q22: q22) |   |   |   |
|   | AML1/RUNX1 | t(8;21)(q22: q22) |   |   |   |
|   | unknown | t(7;22)(q22: q13) |   |   |   |
|   | unknown | t(7;22)(q22: q13) |   |   |   |
|   | unknown | t(X;2)(q28: p11.1) |   |   |   |
|   | unknown | t(7;15)(q36: p11.1) |   |   |   |
|   | unknown | t(1;5)(p32: q12) |   |   |   |
|   | unknown | t(15;22)(q22: q13) |   |   |   |

Figure 42.

METHOD TO IDENTIFY CANCER FUSION GENES

CROSS REFERENCE TO RELATED APPLICATIONS

This application claims priority to U.S. Provisional Patent Application 61/073,211, entitled "Identification of DNA Segments Involved in Chromosomal Rearrangements", filed Jun. 17, 2008, the contents of which are herein incorporated by reference.

FIELD OF INVENTION

This invention relates to chromosome analysis. Specifically, the invention analyzes isolated DNA segments and determines the possibility of chromosomal rearrangement through genotypic characteristic analysis.

BACKGROUND OF THE INVENTION

Cancer results from uncontrolled cellular growth, due to a breakdown of normal cellular responses and cell cycle pathways, characterized by the progressive accumulation of lesions in the tumor genome. The number, severity and types of these lesions determine the biological properties of a given tumor. Genomic rearrangements, often the result of a translocation, interstitial deletion, or chromosomal inversion, account for the onset, development and progression of many tumorigenic diseases and predispositions to such diseases. Oncogenic fusion genes may lead to a gene product with a new or different function from the two fusion partners or upregulation of the gene product. Most fusion genes are found from hematological cancers, sarcomas and prostate cancer (Mitelman F, et al., "The impact of translocations and gene fusions on cancer causation." Nat Rev Cancer. 2007 April; 7(4):233-45. Epub 2007 Mar. 15; Teixeira M R, "Recurrent fusion oncogenes in carcinomas." Crit Rev Oncog. 2006 December; 12(3-4):257-71) and lymphomas (Vega F, Medeiros L J, "Chromosomal translocations involved in non-Hodgkin lymphomas." Arch Pathol Lab Med. 2003 September; 127(9): 1148-60).

Most if not all fusion genes have been discovered as a result of pursuing to the specific goal of isolating a fusion gene expected to be associated with a chromosomal translocation, with one recent exception representing a more general approach (Raphael B J, et al. "A sequence-based survey of the complex structural organization of tumor genomes." Genome Biol. 2008; 9(3):R59. Epub 2008 Mar. 25). Karyotypic detection of translocations has been very useful for cancer researchers, especially in identification of chromosomal translocation. Clinically, the presence or absence of specific translocations has therapeutic and prognostic implications. More fundamentally, genes identified at the translocation breakpoints are strong candidates for involvement in malignant transformation (Sanchez-Garcia, I. Anna. Rev. Genet. 1997 40 31:429-453). These translocations serve as markers of the malignant state and can be either the cause or the consequence of the transformed state. For example, the Philadelphia chromosome is a specific t(9;22)(q34;q11) translocation that fuses the B-cell antigen receptor gene BCR and the 45 ABL oncogene (De Klein A, et al. "A cellular oncogene is translocated to the Philadelphia chromosome in chronic myelocytic leukaemia." Nature. 1982 Dec. 23; 300(5894): 765-7). This fusion is thought to represent the crucial event in the development of chronic granulocytic leukemia. However, this translocation can also appear later in the course of multiple forms of leukemia. Solid tumors as well may have characteristic translocations, suggesting that the development of an unstable chromosomal state increases the likelihood of translocations which in turn increase the likelihood of tumor progression (Rabbitts T H, "Chromosomal translocations in human cancer." Nature 1994 Nov. 10; 372(6502):143-9; Sanchez-Garcia I, "Consequences of chromosomal abnormalities in tumor development." Annu Rev Genet. 1997; 31:429-53).

Chromosomal rearrangements are involved in a multiplicity of cellular events, which includes oncogenesis. The rearrangements can be detected microscopically, but determining the segments of DNA actually involved in the rearrangement is a tedious process, especially within a large DNA region. There are as many as 50,000 of these rearrangements with almost all having essentially unknown fusion points, i.e. the precise DNA segments are still undetermined. These rearrangements are listed in what is called the Mitelman database at an NIH web site, which contains over 50,000 case reports all representing likely unique chromosomal rearrangements. In all cases they are associated with some human pathological condition, mostly cancer. In most cases, limited DNA segments defining the novel chromosome junctions are not known.

The study of cancer fusion genes, arising from chromosomal translocations during cancer cell development, has led to a much more sophisticated understanding of the basis of cancer and to designer drugs specifically targeted to certain cancers. For example, translocations that have fused the c-myc gene with the IgH gene have led to the understanding that part of the development of Burkitt's lymphoma is due to an abnormal and apparently perennial activation of the c-myc gene, which in turn stimulates cell proliferation (Taub, R., et al. "Translocation of the c-myc gene into the immunoglobulin heavy chain locus in human Burkitt lymphoma and murine plasmacytoma cells." Proc. Nat'l Acad. Sci. USA. 1982 December; 79(24):7837-41; Dalla-Favera, R., et al. Human c-myc one gene is located on the region of chromosome 8 that is translocated in Burkitt lymphoma cells. Proc. Nat'l Acad. Sci. USA. 1982 December; 79(24):7824-7; Neel, B. G., et al. Two human c-onc genes are located on the long arm of chromosome 8. Proc. Nat'l Acad. Sci. USA. 1982 December; 79(24):7842-6) and the understanding of the structure of the bcr-abl protein, resulting from the fusion of the bcr and abl genes (Heisterkamp, N., et al. Structural organization of the bcr gene and its role in the Ph' translocation. Nature. 1985 Jun. 27-Jul. 3; 315(6022):758-61), led to the discovery and use of Gleevec (Buchdunger, E., et al. Inhibition of the Abl protein-tyrosine kinase in vitro and in vivo by a 2-phenylaminopyrimidine derivative. Cancer Res. 1996 Jan. 1; 56(1):100-4; Druker, B. J., et al. Effects of a selective inhibitor of the Abl tyrosine kinase on the growth of Bcr-Abl positive cells. Nat. Med. 1996 May; 2(5):561-6), which efficiently retards the progress of chronic myelocytic leukaemia without the side of effects of less specific, anti-proliferative drugs. Moreover, it is expected that fusion proteins may be used to generate cancer specific immune responses (Chiarle, R., et al. The anaplastic lymphoma kinase is an effective oncoantigen for lymphoma vaccination. Nat. Med. 2008 June; 14(6):676-80. Epub 2008 May 11).

Currently, chromosomal fusion cancer testing requires laboratory personnel to identify the point of chromosomal fusion by karyotype analysis, followed by fluorescence in-situ hybridization (FISH) analysis of BAC clones to identify DNA region involved. Finally, the genes, or regions, in proximity to the BAC clone are analyzed for a fusion event using mRNA-based assays, such as reverse PCR. Alternatively, a BAC library is created from cells possessing a translocation. The end sequences of these clones are sequenced and analyzed by computer to identify any two "end sequences" that are not on the same chromosome A precise diagnosis is the first requirement for rational therapy, since each individual patient, as well as each individual tumor, has certain unique genetic traits. These differences in patients and tumors with similar phenotypic characteristics may not have the same underlying genotypes, and therefore, may respond differently to the same treatment. The classical histopathological and clinical criteria used to assess the likelihood of response to the most commonly used modalities used to treat cancer and other diseases and disorders are inadequate predictors of treatment efficacy. A case-by-case approach to identifying fusion genes is inefficient, with over 50,000 reported disease-associated chromosomal rearrangements in the Mitelman database. Consequently, there is a significant and unmet need for accurate diagnostic methods that improve patient care and disease outcome.

SUMMARY OF THE INVENTION

The invention provides a means to analyze fusion incidents, predicting, or at least substantially narrowing down, genes involved in chromosomal arrangement detected by light microscopy. The method requires the size of segments in a DNA region be determined. To identify a segment of DNA involved in a chromosome rearrangement, the largest genes within the segment are determined. For example, if a microscopic analysis reveals that the rearrangement has occurred within a two million base pair segment, the largest three genes in those 2 million base pairs is determined. After the DNA segment size is known, the inventive statisical analyses are applied.

Fifty-nine fusion genes were selected from the published literature and the Atlas of Genetics and Cytogenetics in Oncology and Haematology to determine whether these genes have features in common that would distinguish them from neighboring genes. This type of information offers the ability to predict which genes, within the large regions defined by karyotype analyses of chromosomal translocations, are most likely to be involved in a fusion event. The 59 genes involved in fusion events were analyzed to determine which genomic characteristics the fusion genes share. The common genomic characteristics were assessed to determine the prognostic ability of using the genes to predict other fusion genes within the genome.

The results indicated that, with a high degree of probability and statistical significance, the majority of fusion genes are either very large, compared to their neighbors, or have an unusually high degree of evolutionary conservation, or both. An algorithm was generated to calculate fusion events based on these characteristics and the occurrence of the translocation events. Select large candidate genes were subjected to PCR to test the prognostic ability of the algorithm on apparent, unknown fusion genes associated with acute myeloid leukemia (AML) chromosomal translocations and with translocations in a variety of tissue culture cell lines. Analyses of the data indicated that most known cancer fusion genes are formed from relatively large genes, compared to neighboring genes, or from genes that are highly conserved in evolution, compared to neighboring genes. A quantitative assessment of the expectations of identifying new fusion genes identified as many as 32 new AML-related cancer fusion genes (Table 3) using the size and evolutionary conservation parameters as guides.

Identification of gene-breakpoints without reference to size or evolutionary conservation have indicated that the gene density surrounding genes that form cancer fusion genes is about 29 genes per 2 million base pairs. Thus, to generate a PCR matrix of primers, such that primers representing all 29 genes from one chromosome participating in a translocation were combined with primers representing all 29 genes from a second chromosome, 29×29=841 assays would be necessary. Each PCR assay would attempt to amplify cDNA from RNA from a patient with a single, previously characterized translocation. Few of the translocation breakpoints are established sufficiently precisely to narrow the gene region to about 2 million base pairs. Thus in most cases, more than 29 genes will be candidates for participating in the fusion and more primers would be required. But the above numbers provide a comparison reference point for 32 translocations, ie, about a total of 26,912 assays. Because the gene orientations are all known, and would be revealed by simple inspection of the human genome data representing the approximate position of the translocation breakpoint and the p- or q-arm of the chromosome involved in the translocation, only one primer, either a 5' or 3' primer, would be needed to represent any given gene in the PCR matrix.

The proposed approach indicates a 46% chance of identifying a fusion gene by designing a PCR matrix where only the 5 largest genes are represented in the matrix, i.e., a PCR matrix with 25 assays, with each assay representing mRNA from cancer cells representing a single patient. This is because there is a 67.8% chance that either one of the partners will be among the top five largest genes (Table 1). Thus, for thirty-two samples, there is the likelihood of identifying about 15 cancer fusion genes with this approach, representing a total of 32×25=800 PCR assays. In addition, an estimated 54% of the translocations could be pursued by application of the evolutionary conservation parameter. For example, primers for the five most conserved genes in a DNA segment representing a translocation breakpoint for chromosome A could be combined with the primers representing the five largest genes of chromosome B, and so on. This approach would require 5×5 assay-matrix three more times to exploit both evolutionary conservation and size parameters, leading to the expectation of about more 12 fusion genes from 32 patient samples. The remaining 5 fusion genes could then be identified by the expected 29×29 matrix representing a test for 100% of the possible genes in the two chromosomes at their respective translocation breakpoints. The total number of reactions, for all 32 patient samples, in this case, would be about 6280, versus the 26,912 reactions needed without application of size or evolutionary conservation parameters.

Testing was performed on 32 acute myeloid leukemia (AML) samples (Moffitt Cancer Center tumor bank, Tampa, Fla.), as seen in FIG. 42, where there is no information regarding the AML-related fusion gene created by the translocations. Results are easily verified and cross-references using other databases, such as PubMed (U.S. National Library of Medicine, Bethesda, Md.), as seen in Tables 3 and 4. The results demonstrate the relatively high frequencies of unstudied translocations in current AML patients and the high likelihood of obtaining additional samples.

The proposed approach should lead to identification of 15 new fusion genes in about 46% of the above indicated 32 AML cases, which was expected based on results indicating that about 68% of the fusion gene partners are among the five largest genes in the region of the translocation breakpoint, when there is an average gene density of about 20 and an upper limit gene density of above 44, for 2 million base pairs. This corresponds to a 7-fold enrichment in the above circumstances. In situations where no fusion gene is identified by a PCR matrix that covers the largest genes in two chromosomal regions representing the two breakpoints for a translocation, the top 17% most evolutionarily conserved genes are selected and subjected to the PCR assay matrix. The testing is expected to yield a total of 83% of the fusion genes tested. Results of the 32 unknown AML translocations in Table 3 confirm these expectations. The tests were designed to verify the algorithm for identification of fusion genes, which facilitates the inexpensive and technically straightforward large-scale identification of fusion genes.

In specific embodiments, the algorithm is generated by select translocations with chromosomal break points and select largest 17% of genes for both chromosomal regions involved in the translocation breakpoint. These selected genes are subjected to a PCR assay matrix of patient sample mRNA. The 17% most evolutionarily conserved genes for one chromosome are then selected and matched with the largest 17% of genes from the other chromosome, for a PCR assay matrix. The selected genes are then focused on for further testing. This method allows practical screening of the general population for cancer fusion genes. This type of large-scale screening has the potential of identifying cancer fusion genes that occur in the absence of disease; and the potential of early identification of cancer fusion genes that predict a high likelihood of developing cancer. Further, an accelerated identification of cancer fusion genes will also improve public health by providing for opportunities to design drugs specific for the fusion protein and to monitor treatments and prognoses, with PCR-based monitoring tests that detect very small numbers of cancer cells.

The present invention also provides methods and compositions directed to assessing or predicting whether a patient is likely to respond to a particular drug or therapeutic regimen by analyzing that patient's genomic profile, for example, or a region of the patient's genomic profile that includes one or more genetic or genomic loci of interest. The methods and compositions of the invention are useful in determining a therapeutic regimen for an individual patient, the preferred therapy or therapeutic regimen being one that targets or treats one or more physiological pathways affected by the genetic rearrangements (e.g., one or more amplifications and/or deletions) identified in the patient's genomic profile, thereby ameliorating that patient's condition. The methods and compositions are useful in evaluating the suitability of a particular therapy or therapeutic regimen for a particular patient. Certain embodiments of the present invention also assess the likelihood of a patient's response to a therapy that targets or treats one or more downstream effects of chromosomal rearrangement at a particular genetic locus.

The present invention also provides a highly efficient means to determine DNA segments involved chromosomal rearrangements, and allows for an efficient means of screening genes, thereby allowing PCR tests for these rearrangements. PCR primers can be designed to test each of these three genes or to test potential mRNA fusions resulting from the three gene fusions. If none of the top three sized-genes is part of the rearrangement, then select the top 7 genes, according to species homology percentage peaks, over the 2 million base pairs. The data indicates that with this follow up, there is about an 83% chance of identifying the genes involved in the chromosomal rearrangement. In sum, using this two step procedure for any chromosomal rearrangement, there is only about a 5% chance of not identifying a fusion gene or DNA segment. Knowing the fusion points in chromosomal rearrangements could lead to mass population screening tools, i.e., like a PSA test.

BRIEF DESCRIPTION OF THE DRAWINGS

For a fuller understanding of the invention, reference should be made to the following detailed description, taken in connection with the accompanying drawings, in which:

FIGS. 1(a) through 1(c) are spreadsheets on the RNA transcripts for (ABL), and the transcripts on either side of the known cancer fusion gene. The spreadsheet contains the exact chromosomal coordinates represented by the fusion gene and the surrounding genes. (upper right corner).

FIGS. 2(a) through 2(c) are spreadsheets on the RNA transcripts for (AF4), and the transcripts on either side of the known cancer fusion gene. The spreadsheet contains the exact chromosomal coordinates represented by the fusion gene and the surrounding genes. (upper right corner).

FIGS. 3(a) through 3(b) are spreadsheets on the RNA transcripts for (ALK), and the transcripts on either side of the known cancer fusion gene. The spreadsheet contains the exact chromosomal coordinates represented by the fusion gene and the surrounding genes. (upper right corner).

FIGS. 4(a) through 4(d) are spreadsheets on the RNA transcripts for (BCR), and the transcripts on either side of the known cancer fusion gene. The spreadsheet contains the exact chromosomal coordinates represented by the fusion gene and the surrounding genes. (upper right corner).

FIGS. 5(a) through 5(b) are spreadsheets on the RNA transcripts for (BIRC3), and the transcripts on either side of the known cancer fusion gene. The spreadsheet contains the exact chromosomal coordinates represented by the fusion gene and the surrounding genes. (upper right corner).

FIGS. 6(a) through 6(e) are spreadsheets on the RNA transcripts for (CLTCL1), and the transcripts on either side of the known cancer fusion gene. The spreadsheet contains the exact chromosomal coordinates represented by the fusion gene and the surrounding genes. (upper right corner).

FIGS. 7(a) through 7(f) are spreadsheets on the RNA transcripts for (CREBBP), and the transcripts on either side of the known cancer fusion gene. The spreadsheet contains the exact chromosomal coordinates represented by the fusion gene and the surrounding genes. (upper right corner).

FIGS. 8(a) through 8(e) are spreadsheets on the RNA transcripts for (DDIT3), and the transcripts on either side of the known cancer fusion gene. The spreadsheet contains the exact chromosomal coordinates represented by the fusion gene and the surrounding genes. (upper right corner).

FIGS. 9(a) through 9(b) are spreadsheets on the RNA transcripts for (DDX10v2), and the transcripts on either side of the known cancer fusion gene. The spreadsheet contains the exact chromosomal coordinates represented by the fusion gene and the surrounding genes. (upper right corner).

FIGS. 10(a) through 10(b) are spreadsheets on the RNA transcripts for (DDX10), and the transcripts on either side of the known cancer fusion gene. The spreadsheet contains the exact chromosomal coordinates represented by the fusion gene and the surrounding genes. (upper right corner).

FIGS. 11(a) through 11(b) are spreadsheets on the RNA transcripts for (ERG), and the transcripts on either side of the known cancer fusion gene. The spreadsheet contains the exact chromosomal coordinates represented by the fusion gene and the surrounding genes. (upper right corner).

FIGS. 12(a) through 12(c) are spreadsheets on the RNA transcripts for (ETV6), and the transcripts on either side of the known cancer fusion gene. The spreadsheet contains the exact chromosomal coordinates represented by the fusion gene and the surrounding genes. (upper right corner).

FIGS. 13(a) through 13(d) are spreadsheets on the RNA transcripts for (EWSR1), and the transcripts on either side of the known cancer fusion gene. The spreadsheet contains the exact chromosomal coordinates represented by the fusion gene and the surrounding genes. (upper right corner).

FIGS. 14(a) through 14(b) are spreadsheets on the RNA transcripts for (FKHRL1), and the transcripts on either side of the known cancer fusion gene. The spreadsheet contains the exact chromosomal coordinates represented by the fusion gene and the surrounding genes. (upper right corner).

FIGS. 15(a) through 15(b) are spreadsheets on the RNA transcripts for (FLT1), and the transcripts on either side of the known cancer fusion gene. The spreadsheet contains the exact chromosomal coordinates represented by the fusion gene and the surrounding genes. (upper right corner).

FIGS. 16(a) through 16(e) are spreadsheets on the RNA transcripts for (FUS), and the transcripts on either side of the known cancer fusion gene. The spreadsheet contains the exact chromosomal coordinates represented by the fusion gene and the surrounding genes. (upper right corner).

FIGS. 17(a) through 17(b) are spreadsheets on the RNA transcripts for (JAZF1), and the transcripts on either side of the known cancer fusion gene. The spreadsheet contains the exact chromosomal coordinates represented by the fusion gene and the surrounding genes. (upper right corner).

FIGS. 18(a) through 18(b) are spreadsheets on the RNA transcripts for (MALT1), and the transcripts on either side of the known cancer fusion gene. The spreadsheet contains the exact chromosomal coordinates represented by the fusion gene and the surrounding genes. (upper right corner).

FIGS. 19(a) through 19(d) are spreadsheets on the RNA transcripts for (MLL1), and the transcripts on either side of the known cancer fusion gene. The spreadsheet contains the exact chromosomal coordinates represented by the fusion gene and the surrounding genes. (upper right corner).

FIGS. 20(a) through 20(e) are spreadsheets on the RNA transcripts for (MLL11Q), and the transcripts on either side of the known cancer fusion gene. The spreadsheet contains the exact chromosomal coordinates represented by the fusion gene and the surrounding genes. (upper right corner).

FIGS. 21(a) through 21(b) are spreadsheets on the RNA transcripts for (MLLT3), and the transcripts on either side of the known cancer fusion gene. The spreadsheet contains the exact chromosomal coordinates represented by the fusion gene and the surrounding genes. (upper right corner).

FIGS. 22(a) through 22(b) are spreadsheets on the RNA transcripts for (MYST3), and the transcripts on either side of the known cancer fusion gene. The spreadsheet contains the exact chromosomal coordinates represented by the fusion gene and the surrounding genes. (upper right corner).

FIG. 23 is a spreadsheet on the RNA transcripts for (NPM1), and the transcripts on either side of the known cancer fusion gene. The spreadsheet contains the exact chromosomal coordinates represented by the fusion gene and the surrounding genes. (upper right corner).

FIGS. 24(a) through 24(b) are spreadsheets on the RNA transcripts for (NTRK3), and the transcripts on either side of the known cancer fusion gene. The spreadsheet contains the exact chromosomal coordinates represented by the fusion gene and the surrounding genes. (upper right corner).

FIGS. 25(a) through 25(c) are spreadsheets on the RNA transcripts for (NUP98), and the transcripts on either side of the known cancer fusion gene. The spreadsheet contains the exact chromosomal coordinates represented by the fusion gene and the surrounding genes. (upper right corner).

FIG. 26 is a spreadsheet on the RNA transcripts for (PAX3), and the transcripts on either side of the known cancer fusion gene. The spreadsheet contains the exact chromosomal coordinates represented by the fusion gene and the surrounding genes. (upper right corner).

FIGS. 27(a) through 27(b) are spreadsheets on the RNA transcripts for (PAX7), and the transcripts on either side of the known cancer fusion gene. The spreadsheet contains the exact chromosomal coordinates represented by the fusion gene and the surrounding genes. (upper right corner).

FIGS. 28(a) through 28(c) are spreadsheets on the RNA transcripts for (PAX8v2), and the transcripts on either side of the known cancer fusion gene. The spreadsheet contains the exact chromosomal coordinates represented by the fusion gene and the surrounding genes. (upper right corner).

FIGS. 29(a) through 29(c) are spreadsheets on the RNA transcripts for (PAX8), and the transcripts on either side of the known cancer fusion gene. The spreadsheet contains the exact chromosomal coordinates represented by the fusion gene and the surrounding genes. (upper right corner).

FIGS. 30(a) through 30(d) are spreadsheets on the RNA transcripts for (PML), and the transcripts on either side of the known cancer fusion gene. The spreadsheet contains the exact chromosomal coordinates represented by the fusion gene and the surrounding genes. (upper right corner).

FIG. 31 is a spreadsheet on the RNA transcripts for (PPARGC1A), and the transcripts on either side of the known cancer fusion gene. The spreadsheet contains the exact chromosomal coordinates represented by the fusion gene and the surrounding genes. (upper right corner).

FIGS. 32(a) through 32(d) are spreadsheets on the RNA transcripts for (RARAv2), and the transcripts on either side of the known cancer fusion gene. The v contains the exact chromosomal coordinates represented by the fusion gene and the surrounding genes. (upper right corner).

FIGS. 33(a) through 33(d) are spreadsheets on the RNA transcripts for (RARA), and the transcripts on either side of the known cancer fusion gene. The spreadsheet contains the exact chromosomal coordinates represented by the fusion gene and the surrounding genes. (upper right corner).

FIGS. 34(a) through 34(b) are spreadsheets on the RNA transcripts for (RUNX1), and the transcripts on either side of the known cancer fusion gene. The spreadsheet contains the exact chromosomal coordinates represented by the fusion gene and the surrounding genes. (upper right corner).

FIG. 35 is a spreadsheet on the RNA transcripts for (RUNX1T1), and the transcripts on either side of the known cancer fusion gene. The spreadsheet contains the exact chromosomal coordinates represented by the fusion gene and the surrounding genes. (upper right corner).

FIG. 36 is a spreadsheet on the RNA transcripts for (SS18v2), and the transcripts on either side of the known cancer fusion gene. The spreadsheet contains the exact chromosomal coordinates represented by the fusion gene and the surrounding genes. (upper right corner).

FIG. 37 is a spreadsheet on the RNA transcripts for (SS18), and the transcripts on either side of the known cancer fusion gene. The spreadsheet contains the exact chromosomal coordinates represented by the fusion gene and the surrounding genes. (upper right corner).

FIGS. 38(a) through 38(b) are spreadsheets on the RNA transcripts for (SUZ12), and the transcripts on either side of the known cancer fusion gene. The spreadsheet contains the exact chromosomal coordinates represented by the fusion gene and the surrounding genes. (upper right corner).

FIGS. 39(a) through 39(c) are spreadsheets on the RNA transcripts for (TMPRSS2v2), and the transcripts on either side of the known cancer fusion gene. The spreadsheet contains the exact chromosomal coordinates represented by the fusion gene and the surrounding genes. (upper right corner).

FIGS. 40(a) through 40(c) are spreadsheets on the RNA transcripts for (TMPRSS2), and the transcripts on either side of the known cancer fusion gene. The spreadsheet contains the exact chromosomal coordinates represented by the fusion gene and the surrounding genes. (upper right corner).

FIGS. 41(a) through 41(b) are spreadsheets on the RNA transcripts for (ZBTB16), and the transcripts on either side of the known cancer fusion gene. The spreadsheet contains the exact chromosomal coordinates represented by the fusion gene and the surrounding genes. (upper right corner).

FIG. 42 is a table showing fusion genes and the chromosomal translocation of the gene for acute myeloid leukemia samples.

DETAILED DESCRIPTION OF THE PREFERRED EMBODIMENT

Figure 43:
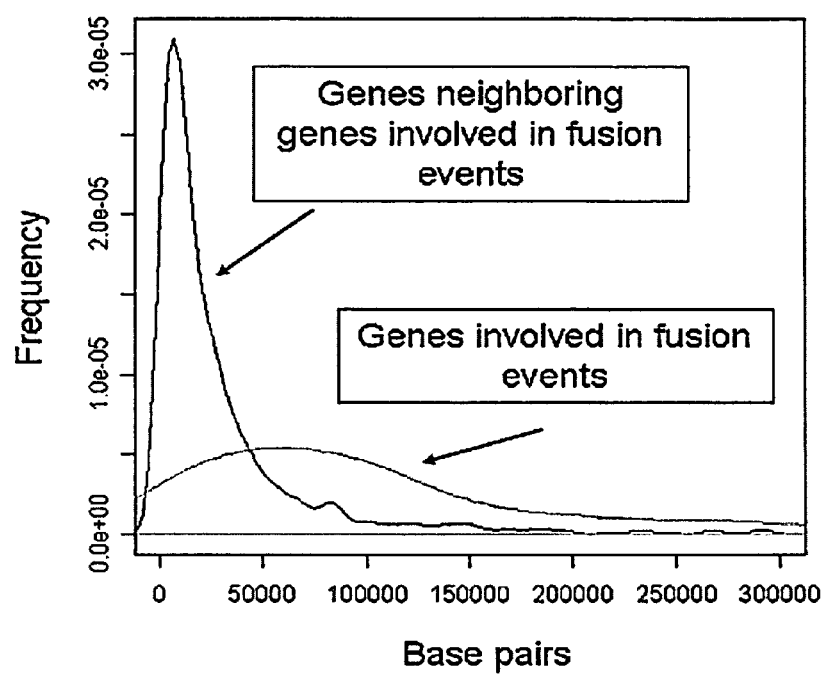
FIG. 43 is a graph depicting the frequencies of sizes represented by the genes involved in fusion events and the neighboring genes, one million base pairs on either side of the fusion-related genes.

Thirty-six genes involved in fusion events were selected using the PubMed database (U.S. National Library of Medicine, Bethesda, Md.) for a preliminary study. An additional 23 genes involved in fusion events were then selected from the Atlas of Genetics and Cytogenetics in Oncology and Haematology (Jean-Loup Huret, ed., University Hospital, Poitiers, France). The analysis began using the latter 23 genes with chromosome 22, and worked towards larger chromosomes until 23 genes that did not involve either the immunoglobulin or T-cell receptor loci were selected. To compare the fusion genes with neighboring genes, a region of one million base pairs was selected on either side of the fusion-related gene using the Genome Browser (UCSC Genome Bioinformatics Group, University of California, Santa Cruz, Calif.). The available sizes for all genes in the two million base pair region, and the region representing the fusion gene, were downloaded into spreadsheets, seen in FIGS. 1-41(b). The spreadsheets representing each fusion gene was then inspected for the rank order of size of the fusion gene, down to fifth largest in size. Genes involved in fusion events that were below the fifth largest were simply noted as below the fifth largest in size (b5). The genome browser data for evolutionary conservation was also inspected for each region of surrounding a fusion gene, as follows. The genome browser window of 2 million base pairs, plus the length of a gene involved in a fusion event, was arbitrarily divided into 42 segments, with each segment being assigned a peak height representing the mammalian evolutionary conservation. The peak heights were assigned in pixels using software able to measure the number of pixels in the distance from the baseline to the height of the peak. Each of the 42 segments was identified as having a peak of rank order of one through five, or below five (b5), as seen in FIG. 43. Thus, each fusion gene was determined to be associated with an evolutionary conservation value, represented by peak height, of one through five, or below five. The settings for establishing the mammalian conservation values using the genome browser were as follows. For the Comparative Genomics tracks, "full" was selected for the Conservation field. Fields for all other selections were set to "hide". For the Conservation setting, all primates were selected (chimp, rhesus, bushbaby); for the placental mammal setting, all placental mammals were selected (treeshrew, mouse, rat, guinea pig, rabbit, shrew, hedgehog, dog, cat, horse, cow, armadillo, elephant, tenrec); and for the vertebrate setting, only opossum and platypus were selected. The pixel height was established as 100. For generating the Excel file, the Table Browser was used. The settings for using the Table Browser were as follows. "Genes and Gene prediction tracks" was selected for the Group field; "UCSC Genes" was selected for the Tracks field; and "knownGene" was selected for the Table field; "selected fields from primary and related tables" was selected for the Output format field. Following the toggling of "get output", "name" (Name of gene), "txStart" (Transcription start position), and "txEnd" (Transcription end position) were selected from the list of hg18.knownGene Table fields; "kgXref" (Link together a Known Gene ID and a gene alias) was selected from the Linked Tables fields. "Allow Selection From Checked Tables" was toggled. "refFlat" was then selected. "Allow Selection From Checked Tables" was re-toggled; "geneName" (Name of gene as it appears in genome browser)" was selected from refFlat fields; "get output" was toggled and saved as a .txt file. This file was then opened using spreadsheets, seen in FIG. 4(a), et seq.

Example 1

Each of the genes, in each of FIGS. 1-41(b), on either side of the fusion gene may have several versions, due to several known primary transcripts. Thus, gene 1 may be listed five times, for example, with each of the five members in the list representing a genomic distance equal to the size of a previously described primary transcript. Each "gene" listed is the genomic representation of all known primary RNA transcripts on either side of the fusion gene, within 1,000,000 base pairs.

Present methodology does not permit one to equate a series of primary transcripts to specific genes. This would have to be performed for each transcript by use of the gene code name in the genomics database. However, this has been done manually and the total number of genes, independently of the number of transcripts, is indicated in the spreadsheets. The gene code name identifies every primary transcript region in the spreadsheet list, to the far left of the file.

The rank order of size for the fusion gene is listed, compared with all other genes provided in the figures, unless it is below 5, in which case it is indicated as "b5". In the majority of cases, as indicated in detail by statistical analyses under separate cover, the fusion gene is one of the top five genes, based on size. The figures also indicate the association of the fusion gene with the nearest comparative genomics peak. In the majority of cases, the fusion gene is associated with one of the highest several peaks, with a statistical analysis to follow.

The probability that the evolutionary conservation peak(s) of 1, 2, 3, 4, or 5 occur within the fusion gene related segment was first estimated using 36 fusion genes. For each fusion gene approximately 2 million base pairs are considered with one million base pairs on either side of the fusion gene, and divided into 42 units. The number of units covered by the fusion gene was obtained by adding 3 units to both sides of the fusion gene. For a fusion gene that is 2 units long, the fusion gene related segment is 8 (2+3+3) units.

If there is no association between being a fusion gene and higher rank order of gene associated conservation peak, the top 1, 2, 3, 4, or 5 peaks should be evenly distributed among the 42 units. The total number of 42 units is taken as the denominator. Considering the numerator—number of units related to the fusion gene, as described above, varies from fusion gene to fusion gene, it is not straightforward to derive the probability of being top 1, 2, 3, 4, or 5 of a fusion gene under the null hypothesis. One approximate approach is to average all the numerators from all fusion genes (10 units long on average). It was assumed that top 1, 2, 3, 4, or 5 peaks may occur anywhere among the 42 units independently. As a result, the probability of being top 1, 2, 3, 4, or 5 conservation peaks under the null hypothesis ($p_0$) can be calculated as:

$$Pr(\text{Top 1}/H0) = 9/42 = 0.214 \tag{1}$$

$$Pr(\text{Top 2}/H0) = Pr(\text{Top 1 or Top 2}) = \text{Prob}(\text{Top 1}) + \text{Prob}(\text{Top 2}) - \text{Prob}(\text{Top 1 and Top 2}) = 9/42 + 9/42 - (9/42)(9/42) = 0.383 \tag{2}$$

$$Pr(\text{Top 3}/H0) = Pr(\text{Top 1 or Top 2 or Top 3}) = \text{Prob}(\text{Top 1}) + \text{Prob}(\text{Top 2}) + \text{Prob}(\text{Top 3}) - \text{Prob}(\text{Top 1 and Top 2}) - \text{Prob}(\text{Top 1 and Top 3}) - \text{Prob}(\text{Top 2 and Top 3}) + \text{Prob}(\text{Top 1 and Top 2 and Top 3}) = 9/42 + 9/42 + 9/42 - (9/42)(9/42) - (9/42)(9/42) - (9/42)(9/42) + (9/42)(9/42)(9/42) = 0.515 \tag{3}$$

Continue on this same line, $$Pr(\text{Top 4}/H0) = 0.619 \tag{4}$$

$$Pr(\text{Top 5}/H0) = 0.701 \tag{5}$$

Furthermore the null hypothesis and alternative hypothesis can be rewritten as:

$$H_0: p = p_0 \text{ vs. } H_a: p > p_0 \tag{6}$$

where p is the probability of being top 1, 2, 3, 4, or 5 conservation peaks.

Statistical significance is obtained by comparing the observed probability of being top 1, 2, 3, 4, or 5 has very small probability for uniformly distributed genes. The probability of being top 1, 2, 3, 4, or 5 of a fusion gene in terms of gene size rank order is estimated and tested against $p_0$ using one-sided z-test (normal approximation).

Top 1 Peak: Hypothesis: $H_0: p = 0.214$ vs. $H_a: p > 0.215$ \hfill (7)

$$p_{obs} = 19/59 = 32.2\% \tag{8}$$

$$Z(\text{statistics}) = \frac{\hat{p} - p_0}{\sqrt{p_0(1-p_0)/n}} = \frac{0.322 - 0.214}{\sqrt{0.214(1-0.214)/59}} = 2.02; \tag{9}$$

p-value = 0.02

Top 2 Peaks: Hypothesis: $H_0: p = 0.383$ vs. $H_a: p > 0.383$ \hfill (10)

$$p_{obs} = 29/59 = 49.2\% \tag{11}$$

$$Z(\text{statistics}) = \frac{\hat{p} - p_0}{\sqrt{p_0(1-p_0)/n}} = \frac{0.492 - 0.383}{\sqrt{0.383(1-0.383)/59}} = 1.73; \tag{12}$$

p-value = 0.04

Top 3 Peaks: Hypothesis: $H_0: p = 0.515$ vs. $H_a: p > 0.515$ \hfill (13)

$$p_{obs} = 40/59 = 67.8\% \tag{14}$$

$$Z(\text{statistics}) = \frac{\hat{p} - p_0}{\sqrt{p_0(1-p_0)/n}} = \frac{0.678 - 0.515}{\sqrt{0.515(1-0.515)/59}} = 2.51; \tag{15}$$

p-value = 0.006

Top 4 Peaks: Hypothesis: $H_0: p = 0.619$ vs. $H_a: p > 0.619$ \hfill (16)

$$p_{obs} = 43/59 = 72.9\% \tag{17}$$

$$Z(\text{statistics}) = \frac{\hat{p} - p_0}{\sqrt{p_0(1-p_0)/n}} = \frac{0.729 - 0.619}{\sqrt{0.619(1-0.619)/59}} = 1.74; \tag{18}$$

p-value = 0.04

Top 5 Peaks: Hypothesis: $H_0: p = 0.701$ vs. $H_a: p > 0.701$ \hfill (19)

$$p_{obs} = 50/59 = 84.7\% \tag{20}$$

$$Z(\text{statistics}) = \frac{\hat{p} - p_0}{\sqrt{p_0(1-p_0)/n}} = \frac{0.847 - 0.701}{\sqrt{0.701(1-0.701)/59}} = 2.45; \tag{21}$$

p-value = 0.007

As noted from the analysis, there is a significant association between being a fusion gene and the top 1, 2, 3, 4, or 5 conservation peaks falling within the fusion gene related segment (9 units average long) among the total 42 units representing 2 million base pairs (p-value=0.05).

The fusion gene associated segment is defined as 3 units on both side of the gene and gene itself as compared to the total units of 42 representing 2 million base pairs. As a result the length of a fusion gene associated segment is 9 units on average, which covers almost one quarter of the total 42 units.

For the 59 genes in the data set, the average number of surrounding genes was 29.457, with a range from 4 to 75. The rank order of size of 1 to 5 for the gene data set involved in fusion events was determined, seen in Table 1, among all genes present within one million base pairs on either side of each fusion gene. Genes involved in fusion events that were not among the top five in size were labeled as below 5 (b5) and not ordered further. The size range was selected because karyotype analyses in general has the potential of identifying a region of DNA represented by a chromosomal translocation with a lower limit of about 2 million base pairs. Thus, this size range represents the smallest range usually available, by karyotype analyses, in defining a region that includes a gene involved in a fusion event. The significance of the frequency was also determined, based on the null hypothesis of a binomial distribution of rank orders for the fusion genes (Table 1).

TABLE 1

Summary of sizes and degree of evolutionary conservation of genes involved in fusion events.

| | Fusion gene | Fusion partner(s) | Size rank order[a] | Evolutionary conservation rank order[b] | Disease |
|---|---|---|---|---|---|
| | | | | | Thirty-six genes from the literature |
| 1 | MLL | | 3/45 | 1 | acute lymphoblastic leukemia (ALL); M4/M5 acute nonlymphocytic leukemia (ANLL); acute myelogenous leukemia (AML) |
| 2 | | AF4 | 3/25 | 1 | acute lymphoblastic leukemia (ALL) |
| 3 | | MLLT3 | 1/23 | 1 | acute non-lymphocytic leukemias (ANLL) |
| 4 | | MLLT1 | 5/45 | 1 | CD19+ acute lymphoblastic leukemia (ALL), acute non-lymphocytic leukemia (ANLL) |
| 5 | | CREBBP | 1/59 | 2 | treatment related leukemias |
| 6 | MYST3 | | 4/19 | 1 | acute myelomonocytic or monocytic leukaemia (M4 or M5 AML) |
| | | CREBBP | | | See line 5 |
| 7 | ABL | | 1/24 | 1 | CML, acute lymphoblastic leukemias (ALL), acute nonlymphocytic leukemia (ANLL) |
| 8 | | BCR | 2/24 | 4 | CML, ALL, ANLL |
| 9 | ETV6 | | 3/33 | 1 | congenital fibrosarcoma (CFS); congenital mesoblastic nephroma (CMN, cellular and mixed variants); secretory ductal carcinoma of breast, AML; refractory anemia with excess blasts |
| 10 | | NTRK3 | 2/12 | 1 | CFS; CMN; secretory ductal breast carcinoma |
| 11 | | RUNX1 | 1/10 | 3 | B cell ALL (CD10+) |
| | | ABL | | | See line 7 |
| 12 | RUNX1T1 | | 3/5 | 1 | AML, ANLL |
| | | RUNX1 | | | See line 11 |
| 13 | ERG | | 1/12 | 5 | AML; Ewing sarcoma; prostate cancer |
| 14 | | EWSR1 | b5/26 | 1 | Ewing tumors |
| 15 | | TMPRSS2 | b5/17 | b5 | |
| 16 | | FUS | b5/55 | 2 | Angiomatoid fibrous histiocytoma (AFH); Myxoid liposarcoma (MLS); AML. |
| 17 | DDIT3 | | b5/46 | 1 | MLS |
| | | FUS | | | See line 16 |
| 18 | FKHRL1 | | 4/18 | 5 | |
| 19 | | PAX3 | 3/7 | 3 | Alveolar rhabdomyosarcoma (ARMS) |
| 20 | | PAX7 | 5/18 | 1 | |
| 21 | RARA | | 3/63 | b5 | acute promyelocytic leukemia (APL) |
| 22 | | PML | b5/33 | 5 | APL |
| 23 | | ZBTB16 | 3/17 | 3 | APL with a 'variant' translocation |
| 24 | | NPM1 | b5/12 | 2 | promyelocytic ANLL, Anaplastic large cell lymphoma (ALCL) |
| 25 | ALK | | 1/16 | 4 | ALCL; cytoplasmic ALK, inflammatory myofibroblastic tumours |
| 26 | | CLTCL1 | 1/34 | 1 | ALCL |
| 27 | BIRC3 | | b5/20 | 1 | B-cell non-Hodgkin lymphoma (NHL); marginal zone B-cell lymphoma (MZBCL) of mucosa-associated lymphoid tissue (MALT); |
| 28 | | MALT1 | b5/11 | 1 | MALT lymphomas |
| 29 | DDX10 | | 1/13 | b5 | therapy related myelodysplastic syndromes (MDS); ANLL |
| 30 | | NUP98 | 3/30 | 1 | MDS; ANLL |
| 31 | JAZF1 | | 2/19 | 2 | endometrial stromal tumors |

TABLE 1-continued

Summary of sizes and degree of evolutionary conservation of genes involved in fusion events.

| | Fusion gene | Fusion partner(s) | Size rank order[a] | Evolutionary conservation rank order[b] | Disease |
|---|---|---|---|---|---|
| 32 | FLT1 | | 2/11 | 3 | ? |
| 33 | PAX8 | | 3/22 | b5 | follicular thyroid cancer |
| 34 | | PPARGC1A | 2/4 | 1 | follicular thyroid cancer |
| 35 | SS18 | | 5/7 | b5 | synovial sarcoma |
| 36 | SUZ12 | | 4/20 | 2 | endometrial stromal neoplasms |

Twenty-three genes from Atlas of Genetics and Cytogenetics in Oncology and Hematology

| | Fusion gene | Fusion partner(s) | Size rank order[a] | Evolutionary conservation rank order[b] | Disease |
|---|---|---|---|---|---|
| 37 | BCAS3 | | 1/18 | 4 | breast cancer |
| 38 | | BCAS4 | 3/16 | 1 | breast cancer |
| 39 | PDGFB | | b5/34 | 3 | infiltrative skin tumors of intermediate malignancy |
| 40 | | COL1A1 | b5/41 | 5 | infiltrative skin tumours of intermediate malignancy |
| 41 | SEPT5 | | b5/27 | 5 | M4, M2, and M1 ANLL |
| | | MLL | | | See line 1 |
| 42 | ELL | | 2/50 | 2 | M4/M5 leukemia |
| | | MLL | | | See line 1 |
| 43 | SH3GL1 | | b5/48 | b5 | leukemias |
| | | MLL | | | See line 1 |
| 44 | MN1 | | 3/6 | 1 | M4 ANLL and other myeloid malignancies |
| | | ETV6 | | | See line 9 |
| 45 | TOP 1 | | 4/8 | 5 | acute monocytic leukemia |
| | | NUP98 | | | See line 30 |
| 46 | MYH9 | | 2/31 | b5 | ALCL |
| | | ALK | | | See line 25 |
| 47 | MKL1 | | 2/30 | 3 | acute megakaryocytic leukaemia found in infants |
| 48 | SMARCB1 | | b5/30 | b5 | tumor of uncertain origin, occurring in early childhood (due to inactivation of both alleles) |
| 49 | NKX2-2 | | 5/5 | 5 | Ewing's sarcoma See line 14 |
| 50 | TCF3 | | b5/75 | 3 | B-ALL |
| 51 | LYL1 | | b5/57 | 2 | T-cell acute lymphoblastic leukemia; other T-ALL |
| 52 | BRD4 | | 1/46 | 3 | carcinoma with t(15;19) (q14;p13) translocation |
| 53 | CRTC1 | | 1/63 | b5 | mucoepidermoid carcinoma (most common type of malignant salivary gland tumor) |
| 54 | NOTCH3 | | 4/46 | 3 | non-small-cell lung cancer |
| 55 | TFPT | | b5/60 | 3 | childhood pre-B ALL |
| 56 | STK11 | | b5/73 | 2 | Peutz-Jeghers syndrome (PJS)/lung adenocarcinoma (due to somatic mutations) |
| 57 | TPM4 | | b5/41 | b5 | rare soft tissue tumour found in children and young adults; ALCL |
| | | ALK | | | See line 25 |
| 58 | BCL2 | | 2/17 | 2 | B- cell NHL |
| 59 | ASPSCR1 | | b5/61 | 3 | Alveolar soft part sarcoma; a subset of renal cell carcinoma |

[a] rank order and total number of genes within 1 million base pairs on either side are indicated, as in individual spreadsheets in the Figures
[b] as indicated in individual spreadsheets and graphical pdf files indicating evolutionary conservation peaks.

The association of a gene involved in a fusion event with evolutionary conservation occurred independently of gene size was determined by calculating the probability of this association, and the significance of the frequencies. The calculation took into account the 19 genes ranked as being not among one of the top five sizes among neighboring genes, using the null hypothesis of a binomial distribution of rank orders for the fusion genes, seen in Table 2. Results indicate that genes previously identified as being involved in a fusion event have a very high probability, with a high degree of statistical significance, of being among the top five genes in an average set of 29.457 genes, with varying frequencies and significances for the top one through top five categories, seen in Table 2.

TABLE 2

Probability of a gene involved in a fusion event being in the top 1-5 sizes in comparison with neighboring genes within 1 million base pairs on either side.

| Rank order of size of gene involved in a fusion event | Observed Probability | Expected probability | p-value * |
|---|---|---|---|
| 1 | 18.6% | 3.3% | <0.0001 |
| 1 or 2 | 33.9% | 6.7% | <0.0001 |
| 1, 2, or 3 | 52.5% | 10.0% | <0.0001 |
| 1, 2, 3 or 4 | 61.0% | 13.3% | <0.0001 |
| 1, 2, 3, 4 or 5 | 67.8% | 16.7% | <0.0001 |

*Z-test (normal approximation to binomial distribution) was used to test the null hypothesis of NO association between being a fusion gene and higher rank order of gene size.

Figure 44:
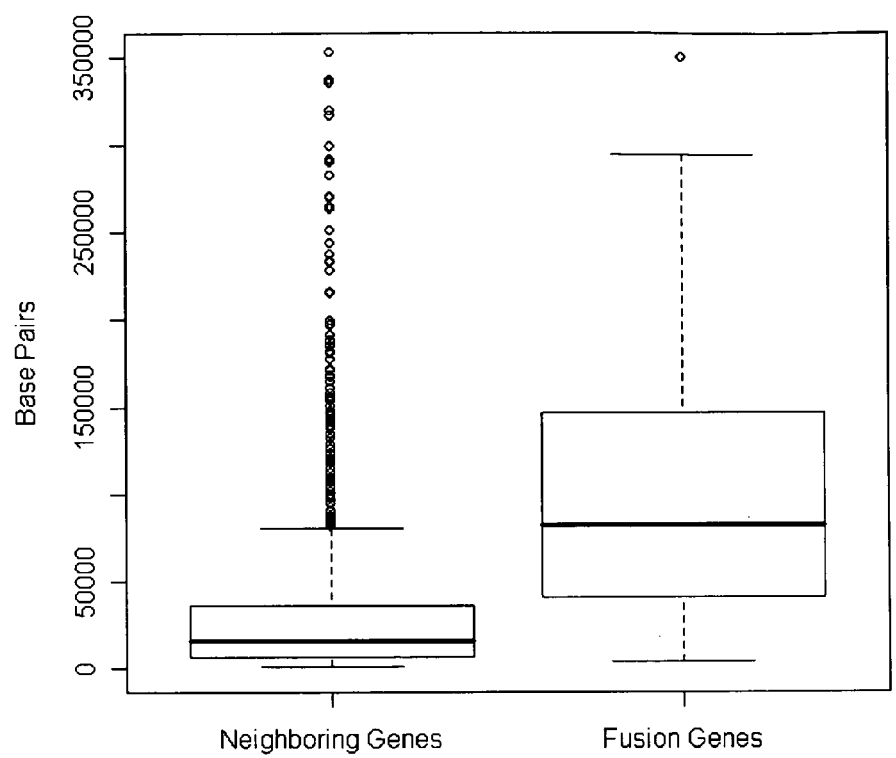
FIG. 44 is a graph depicting the interquartile size range for the genes involved in fusion events and the neighboring genes. The interquartile ranges are indicated by open boxes and the median size is indicated by the bar in the box. The data indicate that the interquartile ranges for the two classes of genes do not overlap.

The size distributions for the genes involved in fusion events was determined. Genes involved in a fusion event have a mean size of 140,254 base pairs (interquartile range of 40,727-146,370), versus all of the neighboring genes, which have a mean size of 35,891 base pairs (interquartile range of 6,358-35,986). Results indicate that the gene size is significantly larger for genes involved in a fusion event than for their respective, neighboring genes, seen in FIGS. 43 and 44.

Figure 45:
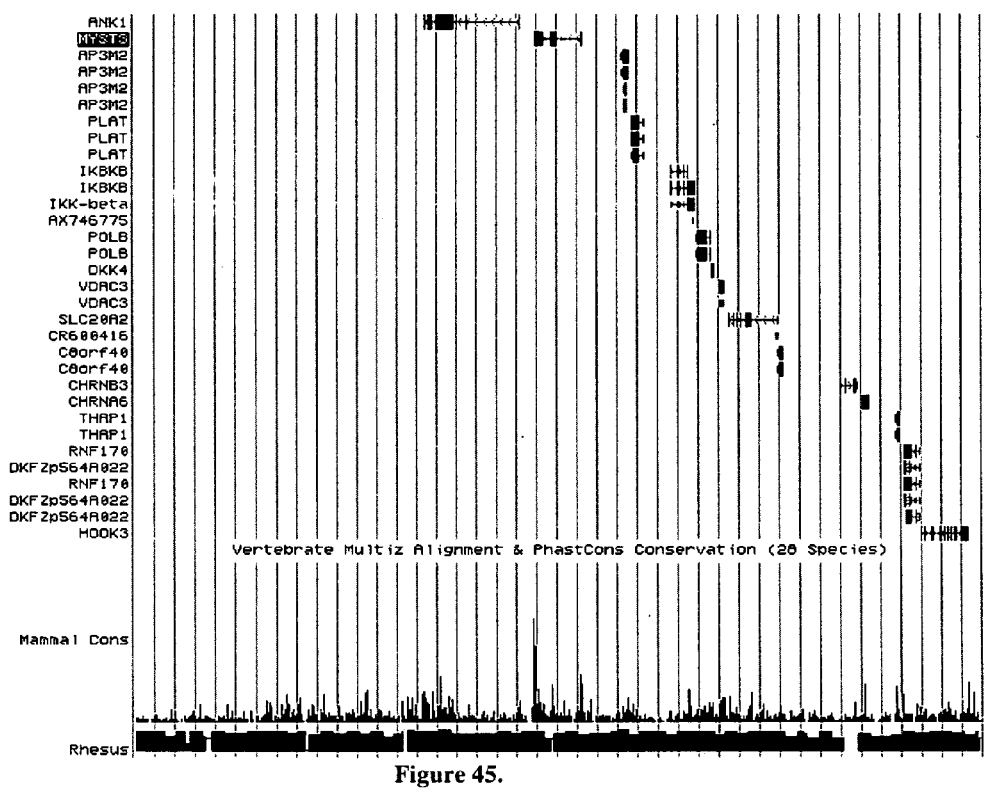
FIG. 45 is a graph showing an example of the evolutionary peak height established for the MYST3 gene, in contrast with peak heights observed for genes within one million base pairs on either side of the MYST3 gene.

The genome browser data suggests that genes involved in fusion events were associated with high levels of evolutionary conservation, as indicated by graphical (histogram) representations of the conservation parameters, seen in FIG. 45. To test this possibility, the peak heights associated with each of one of 42 arbitrary segments dividing the DNA region containing the fusion gene plus 1 million base pairs on either side of each fusion gene were quantified. Genes involved in fusion events were assigned a rank peak height order of 1 through 5 or below 5 (b5). The frequency of a gene involved in a fusion event being associated with one of the top five peak heights, and the statistical significance of the frequency of association, were determined, with results indicating that genes associated with fusion events are more evolutionarily conserved than the neighboring genes in the data set, seen in Table 3.

TABLE 3

Probability of a gene involved in a fusion event being associated with the top 1-5 evolutionary conservation peaks.

| Rank order of evolutionary conservation | Observed probability | Expected probability | p-value* |
|---|---|---|---|
| 1 | 32.2% | 21.4% | 0.02 |
| 1 or 2 | 49.2% | 38.3% | 0.04 |
| 1, 2, or 3 | 67.8% | 51.5% | 0.006 |
| 1, 2, 3 or 4 | 72.9% | 61.9% | 0.04 |
| 1, 2, 3, 4 or 5 | 84.7% | 70.1% | 0.07 |

*Z-test (normal approximation to binomial distribution) was used to test the null hypothesis of NO association between being a fusion gene and higher rank order of conservation peak.

Example 2

To determine whether the association of a gene involved in a fusion event with evolutionary conservation occurred independently of gene size, the probability of this association was determined, and the significance of the frequencies, for the 19 genes ranked as being not among one of the top five sizes among neighboring genes. Results indicated that among these relatively small genes, there was a significant association with evolutionary conservation, seen in Table 4.

A subset of results were analyzed to estimate the probability that the top 1-5 evolutionary conservation peak(s) occur within the fusion gene related segment (fusion Gene +3 units on each site) given the fusion gene size, i.e. largest mRNA, is below top 5. Statistical analysis was repeated, as above, using 19 fusion genes, where the gene size is below the top 5. The probability of being top 1, 2, 3, 4, or 5 conservation peaks under the null hypothesis ($p_0$) can be calculated as:

$$Pr(\text{Top } 1/H_0) = 7/42 = 0.167 \tag{22}$$

$$Pr(\text{Top } 2/H_0) = Pr(\text{Top 1 or Top 2}) = \text{Prob(Top 1)} + \text{Prob(Top 2)} - \text{Prob(Top 1 and Top 2)} = 7/42 + 7/42 - (7/42)(7/42) = 0.306 \tag{23}$$

$$Pr(\text{Top } 3/H_0) = Pr(\text{Top 1 or Top 2 or Top 3}) = \text{Prob(Top 1)} + \text{Prob(Top 2)} + \text{Prob(Top 3)} - \text{Prob(Top 1 and Top 2)} - \text{Prob(Top 1 and Top 3)} - \text{Prob(Top 2 and Top 3)} + \text{Prob(Top 1 and Top 2 and Top 3)} = 7/42 + 7/42 + 7/42 - (7/42)(7/42) - (7/42)(7/42) - (7/42)(7/42) + (7/42)(7/42)(7/42) = 0.421 \tag{24}$$

Continue on this same line, $$Pr(\text{Top } 4/H_0) = 0.518 \tag{25}$$

$$Pr(\text{Top } 5/H_0) = 0.598 \tag{26}$$

Using the null hypothesis above, with p the probability of being in the top 1, 2, 3, 4, or 5 conservation peaks, $p_0$) was calculated using z-test under normal approximation;

$$\text{Top 1 Peak: Hypothesis: } H_0: p = 0.167 \text{ vs. } H_a: p > 0.167 \tag{27}$$

$$p_{obs} = 4/19 = 21.1\% \tag{28}$$

$$t(\text{statistics}) = \frac{\hat{p} - p_0}{\sqrt{p_0(1-p_0)/n}} = \frac{0.22 - 0.167}{\sqrt{0.167(1-0.167)/19}} = 0.51; \tag{29}$$

p-value = 0.3

$$\text{Top 2 Peaks: Hypothesis: } H_0: p = 0.306 \text{ vs. } H_a: p > 0.306 \tag{30}$$

$$p_{obs} = 8/19 = 42.1\% \tag{31}$$

$$t(\text{statistics}) = \frac{\hat{p} - p_0}{\sqrt{p_0(1-p_0)/n}} = \frac{0.421 - 0.306}{\sqrt{0.306(1-0.306)/19}} = 1.09; \tag{32}$$

p-value = 0.14

$$\text{Top 3 Peaks: Hypothesis: } H_0: p = 0.421 \text{ vs. } H_a: p > 0.421 \tag{33}$$

$$p_{obs} = 12/19 = 63.2\% \tag{34}$$

$$t(\text{statistics}) = \frac{\hat{p} - p_0}{\sqrt{p_0(1-p_0)/n}} = \frac{0.632 - 0.421}{\sqrt{0.421(1-0.421)/19}} = 1.86; \tag{35}$$

p-value = 0.03

$$\text{Top 4 Peaks: Hypothesis: } H_0: p = 0.518 \text{ vs. } H_a: p > 0.518 \tag{36}$$

$$p_{obs} = 12/19 = 63.2\% \tag{37}$$

$$t(\text{statistics}) = \frac{\hat{p} - p_0}{\sqrt{p_0(1-p_0)/n}} = \frac{0.632 - 0.518}{\sqrt{0.518(1-0.518)/19}} = 0.99; \tag{38}$$

p-value = 0.16

Top 5 Peaks: Hypothesis: $H_0: p=0.598$ vs. $H_a: p>0.598$ (39)

$p_{obs}=15/19=78.9\%$ (40)

$$t(\text{statistics}) = \frac{\hat{p} - p_0}{\sqrt{p_0(1-p_0)/n}} = \frac{0.789 - 0.598}{\sqrt{0.598(1-0.598)/19}} = 1.70; \quad (41)$$

p-value = 0.04

For genes with size below top 5 there is a significant association between being a fusion gene and top 3 or 5 conservation peaks occurring within the fusion gene related segment (7 units average long) among the total 42 units representing 2 million base pairs, p-value<0.05.

The observed proportions of being top 1, 2, 3, 4 or 5 conservation peaks obtained from the 19 fusions genes (gene size below top 5) are smaller than those based on the full sample set of 59 fusion genes.

TABLE 4

The probabilities of small genes involved in fusion events associated with a high degree of evolutionary conservation

| Rank order of conservation peak | Observed probability | Expected probability | p-value* |
|---|---|---|---|
| 1 | 21.1% | 16.7 | 0.3 |
| 1 or 2 | 42.1% | 30.6 | 0.14 |
| 1, 2, or 3 | 63.2% | 42.1 | 0.03 |
| 1, 2, 3 or 4 | 63.2% | 51.8 | 0.16 |
| 1, 2, 3, 4 or 5 | 78.9% | 59.8 | 0.04 |

*Z-test (normal approximation to binomial distribution) was used to test the null hypothesis of NO association between being a fusion gene and higher rank order of conservation peak.

In the first analysis of the small gene association with evolutionary conservation peaks, seen in Table 4, described in the preceding paragraph, the probability of an association of one of the top five evolutionary conservation peaks and the indicated genes was considered, defining the association as including a maximum distance on either side of the gene. This approach was based on a standard assignment of a 42 peaks per segment of DNA that included the gene involved in a fusion event plus one million base pairs on either side of this gene, i.e., the segment of DNA was divided into a 42 arbitrary segments, as seen in FIG. 45, with one peak allowed per segment. Thus, the data in Table 4 represent the probabilities of the top 1-5 evolutionary conservation peaks being associated with, on average, a 7 unit segment representing the fusion gene size plus 3 units on either side.

To determine whether there was a more direct association of the small fusion genes with evolutionary conservation peaks, the analyses represented by Table 4 was repeated. However, in this case, it was determined that the probability that the small 19 genes involved in fusion events were associated directly with an evolutionary conservation peak. The standard for a direct association was the presence of one of the top five evolutionary conservation peaks in the body of the gene or within a fraction of a unit, when the regions that included 2 million base pairs and the fusion were divided by 42 units, seen in FIG. 45. The average size of the genes, in terms of these arbitrary units, was 1.16 units. The expected result, based on random chance, would be that 13.1% of the fusion genes would be associated with one of the top five evolutionary conservation peaks, keeping in mind that no more than 42 peaks per gene region was permitted. The observed result was that 47.4% of the small genes involved in fusion events were associated with one of the top five evolutionary conservation peaks, with a p value of <0.0001. (See Statistical analyses of the rank order of evolutionary conservation peaks (subset, where peak is associated with the gene).

Example 3

A subset of results were analyzed to estimate the probability that the top 1-5 evolutionary conservation peak(s) occur within the fusion gene given the fusion gene size, i.e. largest mRNA, is below top 5. Statisical analysis was repeated, as above, using 19 fusion genes, where the gene size is below the top 5. Nineteen fusion genes, where the gene size is below the top 5, were considered, using the approximately 2 million base pairs (one million base pairs on either side of the fusion gene), divided into 42 units. The hypothesis used is the same as above. The probability of being top 1, 2, 3, 4, or 5 conservation peaks under the null hypothesis ($p_0$) can be calculated as:

$Pr(\text{Top } 5/H_0)=1-(1-1.16/42)5=0.131$ (42)

The probability of being top 1, 2, 3, 4 or 5 conservation peak of a fusiongene is estimated and tested against the expected probability ($p_0$) using one-sided z-test (normal approximation).

Top 5 Peaks: Hypothesis: $H_0: p=0.131$ vs. $H_a: p>0.131$ (43)

$p_{obs}=9/19=47.4\%$ (44)

$$t(\text{statistics}) = \frac{\hat{p} - p_0}{\sqrt{p_0(1-p_0)/n}} = \frac{0.474 - 0.131}{\sqrt{0.131(1-0.131)/19}} = 4.43; \quad (45)$$

p-value = 0.0001

For genes with size below the top 5 sizes, there is a significant association between being a fusion gene and being among the top 1, 2, 3, 4, or 5 conservation peaks occurring within the fusion gene segment among, with a total 42 units representing 2 million base pairs, p-value<0.0001.

Example 4

The above analyses represent previously identified genes involved in fusion events in cancer. Thus, the analyses do not take into consideration biases that could exist in the process of discovery of these genes. For example, it is possible that larger genes were discovered more frequently because their size made them more accessible to any or all of the technologies used in the process of identifying the fusion gene. Likewise, evolutionarily conserved genes may be more fundamental to cellular function and thus may have been more readily identified and understood by the research community. Thus, it is possible that numerous efforts to identify small genes that are not evolutionarily conserved have failed because smaller genes were not as easily recoverable and identifiable by the available technology; or because genes that are not evolutionarily conserved were simply too poorly understood to permit experimental progress in resolving the fusion event.

However, the above analyses clearly indicate that there exists at least one subclass of large and evolutionarily conserved genes that participate in fusion events. And, it remains possible that all genes involved in fusion events are larger and are more evolutionarily conserved than their neighboring genes, particularly keeping in mind the following issues. First, a larger gene represents a larger target size. Repeat sequences, such as Alu repeats, are likely important in facilitating the recombination of chromosomes and chromosome segments leading to translocations (Chen S J, et al. (1989): Ph1+bcr– acute leukemias: implication of Alu sequences in a chromosomal translocation occurring in the new cluster region within the BCR gene. Oncogene 4:195-202; Papadopoulos P C, et al. (1990): Characterization of the translocation breakpoint sequences in Philadelphia-positive acute lymphoblastic leukemia. Genes Chromosomes. Cancer 1:233-239). A larger gene size is likely to represent a larger number of available repeats, or other recombination-stimulating DNA structures (Kurahashi H, et al. (2007): Molecular cloning of a translocation breakpoint hotspot in 22q11. Genome Res. 17:461-469; Babcock M, et al. (2007): AT-rich repeats associated with chromosome 22q11.2 rearrangement disorders shape human genome architecture on Yq12. Genome Res. 17:451-460), for facilitating the recombination. Second, evolutionarily conserved genes are likely to be genes that function earlier in development, consistent with the notion that ontogeny recapitulates phylogeny. And, cancer cells are generally considered to arise from stem cells having proliferative capacity, where, based on "ontogeny recapitulating phylogeny", it is reasonable to assume genes common to many mammals would be expressed. Evolutionarily conserved genes could thus be genes that are: (i) active and therefore exposed to recombination "accidents" during the stem cell stage; or (ii) specifically linked with stem-cell endowed proliferative capacity.

The evolutionary conservation peaks exploited for the statistical analyses in this study usually represented exons encoding 5' or 3' untranslated regions (UTRs). This is due to the fact that, in most cases, these are the largest exons in the genes that were analyzed. However, the evolutionarily conserved genes involved in fusion events were generally conserved throughout the coding regions and often showed conservation in proximal noncoding regions. To date, there has been no indication that fusion partners share transactivator or microRNA binding sites that might suggest equivalent regulation at equivalent points during stem cell development, despite some preliminary analyses. Furthermore, there is no data yet available that genes involved in fusion events have unusually large 5' or 3' UTRs.

Once DNA segments of limited size are known, polymerase chain reaction (PCR) tests may be developed to assay for the rearrangement, as is known in the art. The present invention provides a technique for isolating DNA segments within a chromosomal rearrangement observable by microscope. These tests can be useful in cancer diagnosis and treatment, to determine whether cancer cells with particular rearrangements are present, as well as useful in other diseases.

The data above indicate approaches for the development of an algorithm for the rapid and efficient identification of DNA segments involved in cancer related chromosomal translocations. Assays of genes that are among the five most evolutionarily conserved genes in the 2 million base pair region results in about a 3.6 fold enrichment over random chance in identifying the genes involved in the fusion event. Currently, there are no routine, systematic approaches to identifying cancer fusion genes, but there are two approaches in the literature that are being explored. However, these approaches require extensive and expensive laboratory techniques and facilities (Volik, S., et al. Decoding the fine-scale structure of a breast cancer genome and transcriptome. Genome Res. 2006 March; 16(3):394-404. Epub 2006 Feb. 3; Maher, C. A., et al. Transcriptome sequencing to detect gene fusions in cancer. Nature. 2009 Mar. 5; 458(7234):97-101. Epub 2009 Jan. 11). There are also certain microarray approaches that take advantage of the imbalance of sequence or SNP copy numbers to identify translocation breakpoints, but these approaches can only identify unbalanced translocation breakpoints and also involve expensive and sophisticated laboratory techniques (Volik, S., et al. Decoding the fine-scale structure of a breast cancer genome and transcriptome. Genome Res. 2006 March; 16(3):394-404. Epub 2006 Feb. 3; Maher, C. A., et al. Transcriptome sequencing to detect gene fusions in cancer. Nature. 2009 Mar. 5; 458(7234):97-101. Epub 2009 Jan. 11).

In contrast to the traditional approaches, the data presented with the associated algorithm require only PCR primer design, followed by RT-PCR for assays for candidate fused mRNAs. This far less labor-intensive approach should lead to the identification of cancer fusion genes a significant percentage of the time. The frequency of cancer fusion gene detection can be increased by selecting for large sized candidate, contributing gene partners. This approach permits routine identification of novel fusion genes in very modest laboratory settings, thus empowering individual public health workers around the world where local genetic polymorphisms may predispose to unique translocations but where expensive analyses facilities are unavailable and access to services by expensive biotech companies is not practical.

Six of the fusion gene partners in the original data set were from AML: (MLL, MYST3, ETV6, RUNX1T1, ERG, and FUS). All of these genes are among the top five largest genes in the 2 million base pair region studied, except for FUS, which is the second most evolutionarily conserved gene in the 2 million base pair region studied for this gene. Thus, the new AML fusion genes were not expected to be any different from other cancers with regard to the frequency of large and evolutionarily conserved genes.

Most if not all of the 32 novel translocations represent genome sizes larger than 2 million base pairs. The first ten translocations examined showed distinct translocations from Table 3 and evidence an average of 11.16 megabases for each chromosomal breakpoint, with a range of 1.9 to 27.8 megabases (re-listed as a subset, in Table 4). Thus, the number of PCR assays needed to cover the entirety of two translocation breakpoints averaging 11.16 megabases, given the gene density of 29 genes per 2 million base pairs, would be: $[(11.16/2) \times 29]^2$=equaling about 26,186 PCR assays. To test all ten translocations represented by Table 4, 10×26,186 PCR assays would need to be conducted. The algorithms permit low-cost accumulation of fusion genes, by many relatively modest oncology departments, without need to resort to expensive biotech or big pharmaceutical services to follow up on patient prognoses.

As one example, with results from Table 5 alone, which is the "worst case scenario" in terms of available data at the end of the project, 20 fusion gene partners constitute about [20× 162 genes]=about 3200 genes. If 40% of these fusion gene partners are among the largest 17%, the chi square test would indicate that large genes are favored, with a p-value of $5.4 \times 10^{-8}$; if 20% of the genes were among the largest 17%, the p-value would be 0.23, i.e., not significant. (These statistical tests were done using random number generators to obtain statistical "test data" for the expected versus observed categories.)

TABLE 5

Actual sizes and gene numbers for selected regions identified as being involved in chromosomal translocations.

| 1st ten unknown fusions from Fig. 42 from top to bottom | Paired breakpoints for translocations representing unknown fusion genes | Genome region size (megabases) | Average side for fused breakpoints (megabases) | Number of genes above 140 kb (mean fusion partner size) |
|---|---|---|---|---|
| 1 | 15q13 | 5.7 | 16.2 | 5 |
|   | 19q13 | 26.7 |  | 8 |
| 2 | 2p23 | 8.0 | 9.5 | 9 |
|   | 11q23 | 11.0 |  | 6 |
| 3 | 1p36 | 27.8 | 27.8 | 17 |
|   | 11q13 | 27.8 |  | 8 |
| 4 | 14q32 | 17.5 | 11.6 | 12 |
|   | 19p13.2 | 5.7 |  | 2 |
| 5 | 5q13 | 9.9 | 7.8 | 4 |
|   | 15q13 | 5.7 |  | 5 |
| 6 | 16q24 | 6.1 | 6.21 | 1 |
|   | 19q13.1 | 6.3 |  | 1 |
| 7 | 7q22 | 9.3 | 8.0 | 8 |
|   | 17q12 | 6.6 |  | 4 |
| 8 | 5p11 | 1.9 | 4.1 | 0 |
|   | 19q13.1 | 6.3 |  | 1 |
| 9 | 3q21 | 8.1 | 9.9 | 6 |
|   | 12q13 | 11.7 |  | 5 |
| 10 | 5q13 | 9.9 | 10.5 | 4 |
|   | 11q23 | 11.0 |  | 6 |

In addition to permitted efficient screening of cancers, the present data is useful in designing immune system-based tumor treatments, such as identifying tumor-specific antigens. Immune cells may be stimulated target cancer-specific stem cells or normal proliferation antigens. An example of vaccinating with fusion proteins is shown by Maslak, et al. (Maslak, P G, et al. "A pilot vaccination trial of synthetic analog peptides derived from the BCR-ABL breakpoints in CML patients with minimal disease." Leukemia. 2008 August; 22(8):1613-6. Epub 2008 Feb. 7).

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of a chromosome-based screening method, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

What is claimed is:

1. A method of identifying fusion genes, comprising the steps of:
   generating a chromosomal rearrangement assay algorithm, further comprising the steps:
      providing a set of DNA segments involved in fusion events by cytogenetic analysis of chromosomes;
      assessing the correlation of the DNA segments genomics characteristics to the fusion event, further comprising the steps of:
         calculating the probability the DNA segments are within the top conservation peaks of the DNA region;
         comparing the observed size of the DNA segments to the probability the DNA segments are within the top conservation peaks;
   selecting a DNA, generating cDNA from mRNA, or selecting a mRNA comprising a potential fusion gene;
   segmenting a region of the DNA, cDNA, or mRNA containing the possible fusion gene;
   subjecting the region of DNA to the assay algorithm, wherein the assay algorithm ranks the region of DNA based on size, evolutionary conservation within a predetermined group of animals, or based on size and evolutionary conservation within a predetermined group of animals;
   selecting the fusion genes having the largest size, the highest evolutionary conservation score, or the largest size and highest evolutionary conservation score;
   selecting PCR primers complementary to the most conserved genes or gene products for a first chromosome, the largest genes or gene products in a DNA segment for a first chromosome, or the genes or gene products having a combined largest size and highest evolutionary conservation score for a first chromosome;
   selecting PCR primers complementary to the most conserved genes or gene products, for a second chromosome, the largest genes or gene products in a DNA segment for a second chromosome, or the genes or gene products having a combined largest size and highest evolutionary conservation score for a second chromosome; and
   combining the PCR primers complementary to the selected genes or gene products for the first chromosome with the PCR primers complementary to the selected genes or gene products for the second chromosome;
   wherein the combined primers identify fusion genes.

2. The method of identifying fusion genes of claim 1, wherein the DNA selected is a DNA region that comprises a potential fusion gene and about 1 million base pairs on either side of the potential fusion gene.

3. The method of identifying fusion genes of claim 2, wherein the DNA region is further segmented into 42 segments.

4. The method of identifying fusion genes of claim 3, wherein the DNA segments are segregated into equal-sized segments.

5. The method of identifying fusion genes of claim 1, wherein the largest genes in the DNA segment are the largest 17% of genes.

6. The method of identifying fusion genes of claim 1, wherein the largest genes in the DNA segment are the 17% most conserved genes.

7. The method of identifying fusion genes of claim 1, wherein the evolutionary conservation is determined by assigning a value to the conservation of the DNA segment based on genetic difference from-the predetermined group of animals.

8. An assay for detecting and characterizing chromosomal rearrangements comprising:
   generating a chromosomal rearrangement assay algorithm, further comprising the steps:
      obtaining a set of DNA segments involved in fusion events by cytogenetic analysis of chromosomes;
      assessing the correlation of the DNA segments genomics characteristics to the fusion event, further comprising the steps of:
         calculating the probability the DNA segments are within the top conservation peaks of the DNA region;
         comparing the observed size of the DNA segments to the probability the DNA segments are within the top conservation peaks;
   selecting a DNA, generating cDNA from mRNA, or selecting a mRNA comprising a potential chromosomal rearrangement;
   segmenting a region of the DNA, cDNA, or mRNA containing a possible fusion gene;
   subjecting the region of DNA to the assay algorithm, wherein the assay algorithm ranks the region of DNA based on size, evolutionary conservation within a predetermined group of animals, or based on size and evolutionary conservation within a predetermined group of animals;
   selecting the fusion genes or gene products having the largest size, the highest evolutionary conservation score, or the largest size and highest evolutionary conservation score;
   generating a matrix of PCR primers from the selected genes or gene products having the largest size, the highest evolutionary conservation score, or the largest size and highest evolutionary conservation score; and
   performing a PCR or RT-PCR assay using the matrix of PCR primers;
   wherein the PCR or RT-PCR assay results identify fusion genes.

9. The assay of claim 8, wherein the DNA region selected comprises a potential chromosomal rearrangement and about 1 million base pairs on either side of the potential fusion gene.

10. The assay of claim 8, wherein the largest genes in the DNA segment are the largest 17% of genes.

11. The assay of claim 8, wherein the largest genes in the DNA segment are the 17% most conversed genes.

12. The assay of claim 8, wherein the evolutionary conservation is determined by assigning a value to the conservation of the DNA segment based on genetic difference from the predetermined group of animals.

13. The assay of claim 8, wherein the matrix of PCR primers uses one primer for each selected gene, where the one primer is complementary to a 5' of a selected gene or 3' of a selected gene.

14. The assay of claim 8, further comprising
   selecting PCR primers complementary to the five most conserved genes and largest genes in a DNA segment for a first chromosome;
   selecting PCR primers complementary to the five most conserved genes and largest genes in a DNA segment for a second chromosome;
   combining the PCR primers complementary to the selected genes for the first chromosome with the PCR primers complementary to the selected genes for the second chromosome.

15. The method of identifying fusion genes of claim 1, wherein the predetermined group of animals is primates, placental mammals, or vertebrates;
   wherein the primates group comprises chimp, rhesus, and bushbaby;
   wherein the placental mammals group comprises treeshrew, mouse, rat, guinea pig, rabbit, shrew, hedgehog, dog, cat, horse, cow, armadillo, elephant, and tenrec; and
   wherein the vertebrate group comprises opossum and platypus.

16. The method of identifying fusion genes of claim 1, further comprising:
   generating a matrix of PCR primers from the selected genes having the largest size and highest evolutionary conservation score;
   performing a PCR or RT-PCR assay using the matrix of PCR primers;
   wherein the PCR or RT-PCR assay results identify chromosomal rearrangements.

17. The method of identifying fusion genes of claim 16, wherein the matrix of PCR primers uses one primer for each selected gene, where the one primer is complementary to a 5' of a selected gene or 3' of a selected gene.

18. The assay of claim 8, wherein the predetermined group of animals is primates, placental mammals, or vertebrates;
   wherein the primates group comprises chimp, rhesus, and bushbaby;
   wherein the placental mammals group comprises treeshrew, mouse, rat, guinea pig, rabbit, shrew, hedgehog, dog, cat, horse, cow, armadillo, elephant, and tenrec; and
   wherein the vertebrate group comprises opossum and platypus.

* * * * *